(12) United States Patent
Johansson et al.

(10) Patent No.: US 8,642,734 B2
(45) Date of Patent: Feb. 4, 2014

(54) METHOD OF PRODUCING POLYMERS OF SPIDER SILK PROTEINS

(75) Inventors: Jan Johansson, Stockholm (SE); My Hedhammar, Stockholm (SE); Anna Rising, Uppsala (SE); Kerstin Nordling, Knivsta (SE)

(73) Assignee: Spiber Technologies AB, Uppsala (SE)

( * ) Notice: Subject to any disclaimer, the term of this patent is extended or adjusted under 35 U.S.C. 154(b) by 0 days.

(21) Appl. No.: 13/264,938

(22) PCT Filed: Apr. 21, 2010

(86) PCT No.: PCT/SE2010/050439
§ 371 (c)(1),
(2), (4) Date: Oct. 17, 2011

(87) PCT Pub. No.: WO2010/123450
PCT Pub. Date: Oct. 28, 2010

(65) Prior Publication Data
US 2012/0041177 A1 Feb. 16, 2012

(30) Foreign Application Priority Data

| Apr. 22, 2009 | (EP) | 09158445 |
| Mar. 18, 2010 | (EP) | 10156923 |
| Mar. 18, 2010 | (EP) | 10156927 |

(51) Int. Cl.
*A61K 38/17* (2006.01)
(52) U.S. Cl.
USPC .......................................... 530/353
(58) Field of Classification Search
None
See application file for complete search history.

(56) References Cited

FOREIGN PATENT DOCUMENTS

| WO | WO 03/057727 | 7/2003 | ........... C07K 14/435 |
| WO | WO 2007/078239 | 7/2007 | ........... C07K 14/435 |
| WO | WO 2008/113145 | 9/2008 | ............. C12N 15/10 |
| WO | WO 2008/154547 | 12/2008 | ........... C07K 14/435 |

OTHER PUBLICATIONS

Chen et al., The spinning processes for spider silk, Soft Matter, 2006, vol. 2, pp. 448-451.*
Ayoub, et al. (2007) "Blueprint for a high-performance biomaterial: full-length spider dragline silk genes" PLoS One, vol. 2, No. 6, pp. 1932-6203.
Bittencourt, et al., (2007) "Spidroins from the Brazilian spider *Nephilengys cruentata* (Araneae: nephilidae)" Comparative biochemistry and physiology, Apr, vol. 147, No. 4, pp. 597-606.
Database EMBL [Online] (2006) "*Euprosthenops australis* partial mRNA for major amullate spidrion 1 (MaSpl gene)" XP002547537—retrieved from EBI accession No. EMBL: AM259067.
Database UniProt [Online] (2006) "Subname: full=major ampullate spidroin 1; Flags: precursor; fragment" XP002547538—retrieved from EBI Database accession No. Q05H60 9ARAC.
Dicko, et al., (2004) "Spider silk protein refolding is controlled by changing pH" Biomacromolecules, June, vol. 5, No. 3, pp. 704-709.
Gaines, et al., (2008) "Identification and characterization of multiple spidroin 1 genes encoding major ampullate silk proteins in *Nephila clavipes*" Insect Molecular Biology, 17(5):465-474.
Grip, et al. (2008) "Recombinant production and determinants for fiber formation" Swedish University of Agricultural Sciences, Faculty of Veterinary Medicine and Animal Science Department of Biomedical Sciences and Veterinary Public Health and Department of Anatomy, Physiology and Biochemistry, Uppsala.
Hedhammar, et al. (2008) "Structural properties of recombinant nonrepetitive and repetitive parts of major ampullate spidroin 1 from *Euprosthenops australis*: implications for fiber formation" Biochemistry, Mar., vol. 47, No. 11, pp. 3407-3414.
Lewis, et al. (1996) "Expression and purification of a spider silk protein: a new strategy for producing repetitive proteins" Protein Expressions and Purification, 7:400-406.
Motriuk, et al. (2005) "Analysis of the conserved N-terminal domains in major ampullate spider silk proteins" Biomacromolecules, Dec, vol. 6, No. 6, pp. 3152-3159.
Pan HC, et al. (2007) "Cloning and prokaryotic expression of major ampullate spidroin gene of spider" 23(3):446-51 XP-002547539 (English Abstract).
Rising, et al, (2006) "N-terminal nonrepetitive domain common to dragline, flagelliform, and cylindriform spider silk proteins" Biomacromolecules, Nov, vol. 7, No. 11, pp. 3120-3124.
Rising, et al. (2007) "Spider dragline silk molecular properties and recombinant expression" Swedish University of Agricultural Sciences, Faculty of Veterinary Medicine and Animal Science Department of Biomedical Sciences and Veterinary Public Health and Department of Anatomy, Physiology and Biochemistry, Uppsala.
Stark, et al. (2007) "Macroscopic fibers self-assembled from recombinant miniature spider silk proteins" Biomacromolecules, 8:1695-1701.
European Search Report for EP 09 15 8445 dated Oct. 15, 2009.
International Search Report for PCT/SE2010/050439 dated Jun. 30, 2010.
International Preliminary Report on Patentability dated Nov. 3, 2011.

* cited by examiner

*Primary Examiner* — Suzanne M Noakes
(74) *Attorney, Agent, or Firm* — Harness, Dickey & Pierce, P.L.C.

(57) ABSTRACT

A method of producing polymers of an isolated spider silk protein involves providing a solution of said spider silk protein in a liquid medium at pH 6.4 or higher and/or an ion composition that prevents polymerization of the spider silk protein. The properties of the liquid medium are adjusted to a pH of 6.3 or lower and an ion composition that allows polymerization of the spider silk protein. The spider silk protein is allowed to form polymers in the liquid medium, and the resulting spider silk protein polymers are isolated from the liquid medium. The resulting polymers are useful as fibers, films, foams, nets or meshes.

18 Claims, 9 Drawing Sheets

```
Ea  MaSp1   SHTTPWTNPGLAENFMNSFMQGLSSMPGFTASQLDDMSTIAQSMVQSIQSLAAQGRTSPNKLQALNMAFA
Lg  MaSp1   QANTPWSSKANADAFINSFISSAQNTGSFSQDQMDDMSLIGNTLMTAMDNMG--GRITPSKLQALDMAFA
Lh  MaSp1   QANTPWSSKANADAFINSFISAASNTGSFSQDQMEDMSLIGNTLMAAMDNMG--GRITPSKLQALDMAFA
Nc  MaSp1   -QNTPWSSTELADAFINAFMNEAGRTGAFTADQLDDMSTIGDTIKTAMDKMARSNKSSKGKLQALNMAFA
At  MaSp2   QGATPWENSQLAESFISRFLRFIGQSGAFSPNQLDDMSSIGDTLKTAIEKMAQSRKSSKSKLQALNMAFA
Lg  MaSp2   ---LRWSSKDNADRFINAFLQAASNSGAFSSDQVDDMSVIGNTLMTAMDNMG--GRITPSKLQALDMAFA
Lh  MaSp2   QANTPWSSKENADAFIGAFMNAASQSGAFSSDQIDDMSVISNTLMAAMDNMG--GRITQSKLQALDMAFA
Nim MaSp2   QANTPWSDTATADAFIQNFLGAVSGSGAFTPDQLDDMSTVGDTIMSAMDKMARSNKSSKSKLQALNMAFA
Nc  MaSp2   QARSPWSDTATADAFIQNFLAAVSGSGAFTSDQLDDMSTIGDTIMSAMDKMARSNKSSQHKLQALNMAFA
Ab  CySp1   AVPSVFSSPNLASGFLQCLTFGIGNSPAFTQEQQLDALAQVILNAVSSNTGATASAR--AQALSTALA
Ncl CySp1   PVPSVFSSPSLASGFLGCLTTGIGLSPAFFQEQQDLDDLAKVILSAVTSNTDTSKSAR--AQALSTALA
Lh  TuSp1   ASVNIFNSPNAATSFLNCLRSNIESSPAFPFQEQADLDSIAEVILSDVSS-VNTASSAT--SLALSTALA
Nc  flag    IANSPFSNPNTAEAFARSFVSNIVSSGEFGAQGAEDFDDIIQSLIQAQ-SMGKGRHDTKAKAKAMQVALA
Nlm flag   IVNSPFSNPNTAEAFARSFVSNVVSSGEFGAQGAEDFDDIIQSLIQAQ-SMGKGRHDTKAKAKAMQVALA Ea  MaSp1   SSMAEIAASEEGGGSLSTKTSSIASAMSNAFLQTTGVVNQPFINEITQLVSMFAQAGMNDV
Lg  MaSp1   SSVAEIAASEG--GDLGVTTNAIADALTSAFYQTTGVVNRFISEIRSLISMFAQASANDV
Lh  MaSp1   SSVAEIAASEG--GDLGVTTNAIADALTSAFYQTTGVVNSRFISEIRSLIGMFAQASANDV
Nc  MaSp1   SSMAEIAAVEQGGLSVDAKTNAIADSLNSAFYQTTGAANPQFVNEIRSLINMFAQSSANEV
At  MaSp2   SSMAEIAVAEQGGLSLEAKTNAIASALSAAFLETTGYVNQQFVNEIKTLIFMIAQASSNEI
Lg  MaSp2   SSVAEIAVADG--QNVGGATNAISNALRSAFYQTTGVVNNQFISEISNLINMFAQVSANEV
Lh  MaSp2   SSVAEIAVADG--QNVGAATNAISDALRSAFYQTTGVVNNQFITGISSLIGMFAQVSGNEV
Nim MaSp2   SSMAEIAAVEQGGQSMDVKTNAIANALDSAFYMTTGSTNQQFVNEMRSLINMLSAAAVNEV
Nc  MaSp2   SSMAEIAAVEQGGMSMAVKTNAIVDGLNSAFYMTTGAANPQFVNEMRSLISMISAASANEV
Ab  CySp1   SSLTDLLIAESAESNYSNQLSELTGILSDCFIQTTGSDNPAFVSRIQSLISVLSQNADTNI
Ncl CySp1   SSLADLLISESSGSSYQTISALTNILSDCFVTTTGSNNPAFVSRVQTLIGVLSQSSSSNAI
Lh  TuSp1   SSLAELLVTESAEEIDNQVVALSTILSQCFVETTGSPNPAFVASVKSLLGVLSQSASNYE
Nc  flag    SSIAELVIAESSGGDVQRKTNVISNALRNALMSTTGSPNEEFVHEVQDLIQMLSQEQINEV
Nlm flag   SSIAELVIAESSGGDVQRKTNVISNALRNALMSTTGSPNEEFVHEVQDLIQMLSQEQINEV
```

Fig 1

| | |
|---|---|
| CThyb_Esp | SRLSSPEASS RVSSAVSNLV SSG-PTNSAA LSSTISNVVS QIGASNPGLS |
| CTnat_Eau | SRLSSPSAVS RVSSAVSSLV SNG-QVNMAA LPNIISNISS SVSASAPGAS |
| AF350266_At1 | SRLSSPGAAS RVSSAVTSLV SSGGPTNSAA LSNTISNVVS QISSSNPGLS |
| AY666062_Cm1 | SHLSSPEASS RVSSAVSNLV SSG-STNSAA LPNTISNVVS QISSSNPGLS |
| AF350273_Lg1 | SALAAPATSA RISSHASTLL SNG-PTNPAS ISNVISNAVS QISSSNPGAS |
| AY953074_Lh1 | SALSAPATSA RISSHASALL SSG-PTNPAS ISNVISNAVS QISSSNPGAS |
| AY666068_Mh1 | SHLSSPEASS RVSSAVSNLV SGG-STNSAA LPNTISNVVS QISSSNPGLS |
| U20329_Nc1 | SRLSSPQASS RVSSAVSNLV ASG-PTNSAA LSSTISNVVS QIGASNPGLS |
| AY666076_Np1 | SRLSSPEASS RVSSAVSNLV SSG-PTNSAA LSNTISNVVS QISSSNPGLS |
| AF350277_Nm1 | SRLSSPQASS RVSSAVSNLV ASG-PTNSAA LSSTISNAVS QIGASNPGLS |
| AF350279_Ns1 | SRLSSPEASS RVSSAVSNLV SSG-PTNSAA LSSTISNVVS QIGASNPGLS |
| AY666057_Ov1 | SRLSSPEASS RVSSAVSNLV SSG-PTNSAA LSNTISNVVS QISSSNPGLS |
| AY666064_Ps1 | SRLSSPEASS RVSSAVSNLV SSG-PTNSAA LPNTISNVVS QISSSNPGLS |
| AF350285_Tk1 | SLLSSPASNA RISSAVSALA SGA-ASGPGY LSSVISNVVS QVSSNSGGLV |
| AF350286_Tv1 | SRLSSPASNA RISSAVSALA SGG-ASSPGY LSSIISNVVS QVSSNDGLS |
| ABU20328_Ab2 | SRLSSSAASS RVSSAVSSLV SSG-PTTPAA LSNTISSAVS QISASNPGLS |
| AY365016_Aam2 | -RLSSPQASS RVSSAVSTLV SSG-PTNPAS LSNAIGSVVS QVSASNPGLP |
| AF350263_Aau2 | SRLSSPQASS RVSSAVSTLV SSG-PTNPAA LSNAISSVVS QVSASNPGLS |
| AF350267_At2 | SRLSSPQASS RVSSAVSTLV SSG-PTNPAS LSNAISSVVS QVSSSNPGLS |
| AF350272_Gm2 | SRLSSPQAGA RVSSAVSALV ASG-PTSPAA VSSAISNVAS QISASNPGLS |
| AF350275_Lg2 | SALSSPTTHA RISSHASTLL SSG-PTNSAA ISNVISNAVS QVSASNPGSS |
| AY953075_Lh2 | SALSSPTTHA RISSHASTLL SSG-PTNAAA LSNVISNAVS QVSASNPGSS |
| AY654293_Nc2 | SRLASPDSGA RVASAVSNLV SSG-PTSSAA LSSVISNAVS QIGASNPGLS |
| AF350278_Nm2 | SRLASPDSGA RVASAVSNLV SSG-PTSSAA LSSVISNAVS QIGASNPGLS |
| AF350280_Ns2 | SRLASPDSGA RVASAVSNLV SSG-PTSSAA LSSVIXNAVS QIGASNPGLS |
| AF350269_DtFb1 | SRLSSPEAAS RVSSAVSSLV SNG-QVNVDA LPSIISNLSS SISASATTAS |
| AF350270_DtFb2 | SRLSSPQAAS RVSSAVSSLV SNG-QVNVAA LPSIISSLSS SISASSTAAS |
| U47853_ADF1 | NRLSSAGAAS RVSSNVAAIA SAG----AAA LPNVISNIYS GVLSS--GVS |
| U47854_ADF2 | SRLSSPSAAA RVSSAVS-LV SNGGPTSPAA LSSSISNVVS QISASNPGLS |
| U47855_ADF3 | SRLSSPAASS RVSSAVSSLV SSG-PTKHAA LSNTISSVVS QVSASNPGLS |
| U47856_ADF4 | SVYLRLQPRL EVSSAVSSLV SSG-PTNGAA VSGALNSLVS QISASNPGLS |
| | |
| Consensus | SRLSSPQASS RVSSAVSNLV SSG-PTNSAA LSNTISNVVS QISASNPGLS |

Fig 2

| | |
|---|---|
| CThyb_Esp | GCDVLVQALL EVVSALIHIL GSSSIGQVNY GSAGQATQLV GQSVYQALGE F |
| CTnat_Eau | GCEVIVQALL EVITALVQIV SSSSVGYINP SAVNQITNVV ANAMAQVMG- - |
| AF350266_At1 | GCDVLVQALL EIVSALVHIL GSANIGQVNS SGVGRSASIV GQSINQAFS- - |
| AY666062_Cm1 | GCDVLVQALL EVVSALIHIL GSSSIGQVNY GSAGQATQIV ---------- - |
| AF350273_Lg1 | SCDVLVQALL ELVTALLTII GSSNVGNVNY DSSGQYAQVV SQSVQNAFV- - |
| AY953074_Lh1 | ACDVLVQALL ELVTALLTII GSSNIGSVNY DSSGQYAQVV TQSVQNVFG- - |
| AY666068_Mh1 | GCDVLVQALL EVVSALIHIL GSSSIGQVDY GSAGQATQIV GQSA------ - |
| U20329_Nc1 | GCDVLIQALL EVVSALIQIL GSSSIGQVNY GSAGQATQIV GQSVYQALG- - |
| AY666076_Np1 | GCDVLVQALL EVVSALIHIL GSSSIGQVNY GSAGQATQIV ---------- - |
| AF350277_Nm1 | GCDVLIQALL EVVSALIHIL GSSSIGQVNY GSAGQATQ-- ---------- - |
| AF350279_Ns1 | GCDVLIQALL EVVSALVHIL GSSSIGQVNY GSAGQATQ-- ---------- - |
| AY666057_Ov1 | GCDVLVQALL EVVSAPIHIL GSSSIGQVNY GSAGQATQIV ---------- - |
| AY666064_Ps1 | GCDVLVQALL EVVSALIHIL GSSSIGQVNY GSAGQATQIV ---------- - |
| AF350285_Tk1 | GCDTLVQALL EAAAALVHVL ASSSGGQVNL NTAGYTSQL- ---------- - |
| AF350286_Tv1 | GCDTVVQALL EVAAALVHVL ASSNIGQVNL NTAGYTSQL- ---------- - |
| ABU20328_Ab2 | GCDVLVQALL EVVSALVHIL GSSSVGQINY GASAQYAQMV ---------- - |
| AY365016_Aam2 | SCDVLVQALL EIVSALVHIL GSSSIGQINY SASSQYARLV GQSIAQALG- - |
| AF350263_Aau2 | GCDVLVQALL ELVSALVHIL GSSSIGQINY AAS------- ---------- - |
| AF350267_At2 | GCDVLVQALL EIVSALVHIL GSSSIGQINY AASSQYAQLV GQSLTQALG- - |
| AF350272_Gm2 | GCDVLVQALL EVSALVSIL SSASIGQINY GASGQYAAMI ---------- - |
| AF350275_Lg2 | SCDVLVQALL ELITALISIV DSSNIGQVNY GSSGQYAQMV G--------- - |
| AY953075_Lh2 | SCDVLVQALL EIITALISIL DSSVGQVNY GSSGQYAQIV GQSMQQAMG- - |
| AY654293_Nc2 | GCDVLIQALL EIVSACVTIL SSSSIGQVNY GAASQFAQVV GQSVLSAF-- - |
| AF350278_Nm2 | GCDVLIQALL EIVSACVTIL SSSSIGQVNY GAA------- ---------- - |
| AF350280_Ns2 | GCDVLIXALL EIVSACVTIL SSSSIGQVNY GAA------- ---------- - |
| AF350269_DtFb1 | DCEVLVQVLL EVVSALVQIV CS-------- ---------- ---------- - |
| AF350270_DtFb2 | DCEVLVQVLL EIVSALVQIV SSANVGYINP EASGSLN-AV GSALAAAMG- - |
| U47853_ADF1 | SSEALIQALL EVISALIHVL GSASIGNVSS VGVNSALNAV QNAVGAYAG- - |
| U47854_ADF2 | GCDILVQALL EIISALVHIL GSANIGPVNS SSAGQSASIV GQSVYRALS- - |
| U47855_ADF3 | GCDVLVQALL EVVSALVSIL GSSSIGQINY GASAQYTQMV GQSVAQALA- - |
| U47856_ADF4 | GCDALVQALL ELVSALVAIL SSASIGQVNV SSVSQSTQMI SQALS----- - |
| Consensus | GCDVLVQALL EVVSALVHIL GSSSIGQVNY GSAGQATQIV GQSVAQALGE F |

Fig 2 (continued)

METHOD OF PRODUCING POLYMERS OF SPIDER SILK PROTEINS

CROSS-REFERENCE TO RELATED APPLICATIONS

This application is a National Phase entry of International Application No. PCT/SE2010/050439 filed on 21 Apr. 2011, which claims priority under 35 U.S.C. §§119(a) and 365(b) to EPC Application No. 09158445.8 filed on 22 Apr. 2009, and EPC Application No. 10156923.4 filed on 18 Mar. 2010, and EPC Application No. 10156927.5 filed on 18 Mar. 2010. The above three recited patent applications are incorporated herein by reference in their entirety.

The material in the ASCII text file entitled "1907165_1.txt" is hereby incorporated by reference in its entirety. The ASCII text file entitled "1907165_1.txt" was created on 13 Sep. 2013 and the size is 130 KB.

TECHNICAL FIELD OF THE INVENTION

The present invention relates to the field of recombinant production of proteins, and more specifically to recombinant production of spider silk proteins (spidroins). The present invention provides a method of producing polymers of an isolated spider silk protein. There is also provided novel spider silk proteins and methods and polynucleic acid molecules for producing such proteins and polymers thereof.

BACKGROUND TO THE INVENTION

Spider silks are nature's high-performance polymers, obtaining extraordinary toughness and extensibility due to a combination of strength and elasticity. Spiders have up to seven different glands which produce a variety of silk types with different mechanical properties and functions. Dragline silk, produced by the major ampullate gland, is the toughest fiber, and on a weight basis it outperforms man-made materials, such as tensile steel. The properties of dragline silk are attractive in development of new materials for medical or technical purposes.

Dragline silk consists of two main polypeptides, mostly referred to as major ampullate spidroin (MaSp) 1 and 2, but e.g. as ADF-3 and ADF-4 in *Araneus diadematus*. These proteins have molecular masses in the range of 200-720 kDa. The genes coding for dragline proteins of *Latrodectus hesperus* are the only ones that have been completely characterised, and the MaSp1 and MaSp2 genes encode 3129 and 3779 amino acids, respectively (Ayoub N A et al. PLoS ONE 2(6): e514, 2007). The properties of dragline silk polypeptides are discussed in Huemmerich, D. et al. Curr. Biol. 14, 2070-2074 (2004).

Spider dragline silk proteins, or MaSps, have a tripartite composition; a non-repetitive N-terminal domain, a central repetitive region comprised of many iterated poly-Ala/Gly segments, and a non-repetitive C-terminal domain. It is generally believed that the repetitive region forms intermolecular contacts in the silk fibers, while the precise functions of the terminal domains are less clear. It is also believed that in association with fiber formation, the repetitive region undergoes a structural conversion from random coil and α-helical conformation to β-sheet structure. The C-terminal region of spidroins is generally conserved between spider species and silk types. The N-terminal domain of spider silks is the most conserved region, but its function is not understood. Rising, A. et al. Biomacromolecules 7, 3120-3124 (2006) characterizes the 5' end of the *Euprosthenops australis* MaSp1 gene and deduces the corresponding amino acid sequence. The N-terminal domain of the MaSp1 protein is recombinantly expressed.

Spider silk proteins and fragments thereof are difficult to produce recombinantly in soluble form. Most previous attempts to produce artificial spider silk fibers have included solubilization steps in non-physiological solvents. Several factors complicate the expression of dragline silk proteins. Due to the highly repetitive nature of the genes, and the concomitant restricted amino acid composition of the proteins, transcription and translation errors occur. Depletion of tRNA pools in microbial expression systems, with subsequent discontinuous translation, leading to premature termination of protein synthesis might be another reason. Other reasons discussed for truncation of protein synthesis are secondary structure formation of the mRNA, and recombination of the genes. Native MaSp genes larger than 2.5 kb have been shown to be instable in bacterial hosts. Additionally, there are difficulties in maintaining the recombinant silk proteins in soluble form, since both natural-derived dragline silk fragments and designed block co-polymers, especially MaSp1/ADF-4-derived proteins, easily self-assemble into amorphous aggregates, causing precipitation and loss of protein. See Huemmerich, D. et al. Biochemistry 43, 13604-13612 (2004) and Lazaris, A. et al. Science 295, 472-476 (2002).

Attempts to produce artificial spider silks have employed natural or synthetic gene fragments encoding dragline silk proteins. Recombinant dragline silk proteins have been expressed in various systems including bacteria, yeast, mammalian cells, plants, insect cells, transgenic silkworms and transgenic goats. See e.g. Lewis, R. V. et al. Protein Expr. Purif. 7, 400-406 (1996); Fahnestock, S. R. & Irwin, S. L. Appl. Microbiol. Biotechnol. 47, 23-32 (1997); Arcidiacono, S. et al. Appl. Microbiol. Biotechnol. 49, 31-38 (1998); Fahnestock, S. R. & Bedzyk, L. A. Appl. Microbiol. Biotechnol. 47, 33-39 (1997); and Lazaris, A. et al. Science 295, 472-476 (2002).

Huemmerich, D. et al. Biochemistry 43, 13604-13612 (2004) discloses a synthetic gene, "$(AQ)_{12}NR_3$", coding for repetitive Ala-rich and Gly/Gln-rich fragments and a non-repetitive fragment, all derived from ADF3 from Araneus. The gene is expressed into a soluble protein which aggregates but does not form polymers or fibers.

WO 03/057727 discloses expression of soluble recombinant silk polypeptides in mammalian cell lines and animals. The obtained silk polypeptides exhibit poor solubility in aqueous media and/or form precipitates. Since the obtained silk polypeptides do not polymerise spontaneously, spinning is required to obtain polymers or fibers. Expressed silk polypeptides contain a plurality of repetitive units and a non-repetitive unit derived from the carboxyl-terminal region of spider silk proteins.

WO 07/078,239 and Stark, M. et al. Biomacromolecules 8, 1695-1701, (2007) disclose a miniature spider silk protein consisting of a repetitive fragment with a high content of Ala and Gly and a C-terminal fragment of a protein, as well as soluble fusion proteins comprising the spider silk protein. Fibers of the spider silk protein are obtained spontaneously upon liberation of the spider silk protein from its fusion partner. The small fusion unit is sufficient and necessary for the fiber formation.

Hedhammar, M. et al. Biochemistry 47, 3407-3417, (2008) studies the thermal, pH and salt effects on the structure and aggregation and/or polymerisation of recombinant N- and C-terminal spidroin domains and a repetitive spidroin domain containing four poly-Ala and Gly rich co-blocks. It is disclosed that the secondary and tertiary structure of the N-terminal domain remains unaltered regardless of pH, and the only detected stable assemblies that are formed by the N-terminal domain are dimers. Instead, the C-terminal domain is suggested to have a major role in the assembly of spider silk proteins.

SUMMARY OF THE INVENTION

It is an object of the present invention to provide a method of producing polymers of spider silk proteins, wherein spider silk protein solubility and polymerisation is controlled.

It is also an object of the present invention to provide a method of producing fibers of spider silk proteins, wherein spider silk protein solubility and fiber formation is controlled.

It is another object of the present invention to provide a novel spider silk protein, which can provide spider silk fibers, films, foams, nets and meshes.

It is one object of the present invention to provide a water-soluble spider silk protein, which can readily be manipulated to polymerise into fibers at wish. This property allows for all the following steps to be undertaken under physiological conditions, which decreases the risk for toxicity and protein denaturation.

It is yet another object of the present invention to provide fibers of a novel spider silk protein.

It is one object of the present invention to provide spider silk proteins in large scale, which can readily be manipulated to polymerise into fibers at wish.

It is also an object of the invention to provide methods of producing spider silk proteins and fibers of spider silk proteins.

For these and other objects that will be evident from the following disclosure, the present invention provides according to a first aspect a method of producing polymers of an isolated spider silk protein, comprising the steps of:
(i) providing a spider silk protein consisting of from 170 to 760 amino acid residues and comprising:
  an N-terminal fragment consisting of at least one fragment of from 100 to 160 amino acid residues derived from the N-terminal fragment of a spider silk protein; and
  a repetitive fragment of from 70 to 300 amino acid residues derived from the repetitive fragment of a spider silk protein; and optionally
  a C-terminal fragment of from 70 to 120 amino acid residues, which fragment is derived from the C-terminal fragment of a spider silk protein;
(ii) providing a solution of said spider silk protein in a liquid medium at pH 6.4 or higher and/or an ion composition that prevents polymerisation of said spider silk protein, optionally involving removal of lipopolysaccharides and other pyrogens;
(iii) adjusting the properties of said liquid medium to a pH of 6.3 or lower and an ion composition that allows polymerisation of said spider silk protein;
(iv) allowing the spider silk protein to form polymers, preferably solid polymers, in the liquid medium, said liquid medium having a pH of 6.3 or lower and an ion composition that allows polymerisation of said spider silk protein; and
(v) isolating the spider silk protein polymers from said liquid medium.

In one embodiment, the pH of the liquid medium of steps (iii) and (iv) is 6.2 or lower, such as 6.0 or lower. In one embodiment, the pH of the liquid medium of steps (iii) and (iv) is 3 or higher, such as 4.2 or higher. In certain embodiments, the ionic strength of the liquid medium of steps (iii) and (iv) is in the range of 1-250 mM.

In an embodiment, the pH of the liquid medium of step (ii) is 6.7 or higher, such as 7.0 or higher. In one embodiment, the pH of the liquid medium of step (ii) is in the range of 6.4-6.8.

According to another aspect, the present invention provides a polymer of a spider silk protein, said protein consisting of from 170 to 760 amino acid residues and comprising:
  an N-terminal fragment consisting of at least one fragment of from 100 to 160 amino acid residues derived from the N-terminal fragment of a spider silk protein; and
  a repetitive fragment of from 70 to 300 amino acid residues derived from the repetitive fragment of a spider silk protein; and optionally
  a C-terminal fragment of from 70 to 120 amino acid residues, which fragment is derived from the C-terminal fragment of a spider silk protein.

In certain embodiments of these two aspects, the spider silk protein is consisting of from 170 to 600 amino acid residues and comprising a single N-terminal fragment of from 100 to 160 amino acid residues derived from the N-terminal fragment of a spider silk protein. In certain other embodiments of these two aspects, the N-terminal fragment of the spider silk protein is comprising at least two fragments of from 100 to 160 amino acid residues derived from the N-terminal fragment of a spider silk protein.

In preferred embodiments of these two aspects, the protein is selected from the group of proteins defined by the formulas $NT_2$-REP-CT, NT-REP-CT, $NT_2$-REP and NT-REP, wherein NT is a protein fragment having from 100 to 160 amino acid residues, which fragment is a N-terminal fragment derived from a spider silk protein.

REP is a protein fragment having from 70 to 300 amino acid residues, wherein said fragment is selected from the group of $L(AG)_nL$, $L(AG)_nAL$, $L(GA)_nL$, $L(GA)_nGL$, wherein n is an integer from 2 to 10;
each individual A segment is an amino acid sequence of from 8 to 18 amino acid residues, wherein from 0 to 3 of the amino acid residues are not Ala, and the remaining amino acid residues are Ala;
each individual G segment is an amino acid sequence of from 12 to 30 amino acid residues, wherein at least 40% of the amino acid residues are Gly; and
each individual L segment is a linker amino acid sequence of from 0 to 20 amino acid residues; and CT is a protein fragment having from 70 to 120 amino acid residues, which fragment is a C-terminal fragment derived from a spider silk protein.

In an embodiment, the polymer consists of polymerised dimers of the spider silk protein.

In preferred embodiments, the content of lipopolysaccharides and other pyrogens is 1 EU/mg of isolated protein or lower.

In one embodiment, the polymer is a fiber, film, foam, net or mesh. In a preferred embodiment, the polymer is a fiber having a diameter of more than 0.1 µm and a length of more than 5 mm.

According to one aspect, the present invention provides a method of producing dimers of an isolated spider silk protein, comprising the steps of:
(i) providing a spider silk protein of from 170 to 760 amino acid residues, said protein comprising:
  an N-terminal fragment consisting of at least one fragment of from 100 to 160 amino acid residues derived from the N-terminal fragment of a spider silk protein; and
  a repetitive fragment of from 70 to 300 amino acid residues derived from the repetitive fragment of a spider silk protein; and optionally a C-terminal fragment of from 70 to 120 amino acid residues, which fragment is derived from the C-terminal fragment of a spider silk protein;

(ii) providing a solution of dimers of the spider silk protein in a liquid medium at a pH of 6.4 or higher and/or an ion composition that prevents polymerisation of said spider silk protein; and (iii) isolating the dimers obtained in step (ii), optionally involving removal of lipopolysaccharides and other pyrogens.

In an embodiment, the pH of the liquid medium of step (ii) is 6.7 or higher, such as 7.0 or higher. In one embodiment, the pH of the liquid medium of step (ii) is in the range of 6.4-6.8.

In one embodiment, step (i) of providing said spider silk protein is comprising the sub-steps of:
(a) expressing a polynucleic acid molecule which encodes said spider silk protein in a suitable host; and
(b) isolating the protein obtained in sub-step (a), optionally involving removal of lipopolysaccharides and other pyrogens.

According to an aspect, the present invention provides a dimer of a spider silk protein, said protein consisting of from 170 to 760 amino acid residues and comprising:
an N-terminal fragment consisting of at least one fragment of from 100 to 160 amino acid residues derived from the N-terminal fragment of a spider silk protein; and
a repetitive fragment of from 70 to 300 amino acid residues derived from the repetitive fragment of a spider silk protein; and optionally
a C-terminal fragment of from 70 to 120 amino acid residues, which fragment is derived from the C-terminal fragment of a spider silk protein.

In certain embodiments of these two aspects, the spider silk protein is consisting of from 170 to 600 amino acid residues and comprising a single N-terminal fragment of from 100 to 160 amino acid residues derived from the N-terminal fragment of a spider silk protein. In certain other embodiments of these two aspects, the N-terminal fragment of the spider silk protein is comprising at least two fragments of from 100 to 160 amino acid residues derived from the N-terminal fragment of a spider silk protein.

According to another aspect, the present invention provides an isolated spider silk protein, which consists of from 170 to 760 amino acid residues and is selected from the group of proteins defined by the formulas $NT_2$-REP-CT, NT-REP-CT, $NT_2$-REP and NT-REP, wherein
NT is a protein fragment having from 100 to 160 amino acid residues, which fragment is a N-terminal fragment derived from a spider silk protein.
REP is a protein fragment having from 70 to 300 amino acid residues, wherein said fragment is selected from the group of $L(AG)_nL$, $L(AG)_nAL$, $L(GA)_nL$, $L(GA)_nGL$, wherein
n is an integer from 2 to 10;
each individual A segment is an amino acid sequence of from 8 to 18 amino acid residues, wherein from 0 to 3 of the amino acid residues are not Ala, and the remaining amino acid residues are Ala;
each individual G segment is an amino acid sequence of from 12 to 30 amino acid residues, wherein at least 40% of the amino acid residues are Gly; and each individual L segment is a linker amino acid sequence of from 0 to 20 amino acid residues; and
CT is a protein fragment having from 70 to 120 amino acid residues, which fragment is a C-terminal fragment derived from a spider silk protein.

In one embodiment, the spider silk protein is consisting of from 170 to 600 amino acid residues and is selected from the group of proteins defined by the formulas NT-REP-CT and NT-REP.

In certain embodiments, the spider silk protein is selected from the group consisting of SEQ ID NO: 3-5, 17, 19-23, 25 and 31.

According to an aspect, the present invention provides use of the spider silk proteins of the inventions for producing dimers of the spider silk protein.

According to one aspect, the present invention provides use of the spider silk proteins of the inventions for producing polymers of the spider silk protein.

According to an aspect, the present invention provides use of a dimer of a spider silk protein according to the invention for producing polymers of the isolated spider silk protein.

In preferred embodiments of these aspects, said polymers are produced in a liquid medium having a pH of 6.3 or lower and an ion composition that allows polymerisation of said spider silk protein.

According to one aspect, the present invention provides a composition comprising an isolated spider silk protein according to the invention dissolved in a liquid medium having a pH of 6.4 or higher and/or an ion composition that prevents polymerisation of said spider silk protein.

In an embodiment, the pH of the liquid medium is 7.0 or higher. In one embodiment, the pH of the liquid medium is in the range of 6.4-6.8.

In certain embodiments, the content of lipopolysaccharides and other pyrogens in the composition is 1 EU/mg of isolated protein or lower.

According to another aspect, the present invention provides an isolated polynucleic acid molecule comprising a nucleic acid sequence selected from the group consisting of SEQ ID NO: 14-16, 18 and 24; nucleic acid sequences encoding SEQ ID NO: 3-5, 17, 19-23, 25 and 31; nucleic acid sequences which encodes a spider silk protein according to the invention; and their complementary nucleic acid sequences.

According to yet another aspect, the present invention provides a method of producing a spider silk protein according to the invention, comprising the steps of:
(i) expressing a polynucleic acid molecule which encodes said spider silk protein in a suitable host; and
(ii) isolating the protein obtained in step (i), optionally involving removal of lipopolysaccharides and other pyrogens.

Furthermore, there is provided a method of reversibly assembling a polymer or oligomer of one type of molecule or several different types of molecules, comprising the steps of:
(i) providing said molecules, each molecule comprising
(a) at least one first binding moiety of from 100 to 160 amino acid residues which is derived from the N-terminal fragment of a spider silk protein, and
(b) a second moiety which is individually selected from proteins, nucleic acids, carbohydrates and lipids;
(ii) providing a solution of said molecules in a liquid medium at pH 6.4 or higher and/or an ion composition that prevents polymerisation or oligomerisation of said molecule(s) via said binding moieties;
(iii) adjusting the properties of said liquid medium to a pH of 6.3 or lower and an ion composition that allows polymerisation or oligomerisation of said molecules via said binding moieties;
(iv) allowing said molecules to assemble into a polymer or oligomer via said binding moieties in the liquid medium, said liquid medium having a pH of 6.3 or lower and an ion composition that allows polymerisation or oligomerisation of said molecules via said binding moieties.

In an embodiment, said molecules of step (i) are identical, and said polymer or oligomer of step (iv) is a homopolymer or a homooligomer. In another embodiment, said molecules of step (i) are not identical, and said polymer or oligomer of step (iv) is a heteropolymer or heterooligomer.

In preferred embodiments, said polymer or oligomer of step (iv) is dissolved in said liquid medium having a pH of 6.3 or lower and an ion composition that allows polymerisation or oligomerisation of said molecules.

In one embodiment, the pH of the liquid medium of steps (iii) and (iv) is 6.2 or lower, such as 6.0 or lower, and/or the pH of the liquid medium of steps (iii) and (iv) is 3 or higher, such as 4.2 or higher.

In certain embodiments, the ionic strength of the liquid medium of step (iv) is in the range of 1-250 mM.

In an embodiment, the pH of the liquid medium of step (ii) is 6.7 or higher, such as 7.0 or higher. In one embodiment, the pH of the liquid medium of step (ii) is in the range of 6.4-6.8.

In a preferred embodiment, said second moiety is a protein.

In one embodiment, the method is further comprising the step of: (v) adjusting the properties of said liquid medium to a pH of 6.4 or higher and/or an ion composition that prevents polymerisation or oligomerisation of said molecules to disassemble said polymer or oligomer.

In an embodiment, the pH of the liquid medium of step (ii) and/or step (v) is 6.7 or higher, such as 7.0 or higher. In one embodiment, the pH of the liquid medium of step (ii) and/or step (v) is in the range of 6.4-6.8.

In a preferred embodiment, the polymer or oligomer of step (iv) is used in interaction studies, separation, inducing activity of enzyme complexes or FRET analysis.

In one embodiment, at least one molecule type of step (i) is immobilised to a solid support or to the matrix of an affinity medium.

There is also provided a method of detecting binding interactions between a subset of molecules comprised in a set of molecules, comprising the steps of:
(i) providing said set of molecules, each molecule comprising
   (a) at least one first binding moiety of from 100 to 160 amino acid residues which is derived from the N-terminal fragment of a spider silk protein, and
   (b) a second moiety which is individually selected from proteins, nucleic acids, carbohydrates and lipids;
(ii) providing a solution of said set of molecules in a liquid medium at pH 6.4 or higher and/or an ion composition that prevents polymerisation or oligomerisation of said molecules;
(iii) adjusting the properties of said liquid medium to a pH of 6.3 or lower and an ion composition that allows polymerisation or oligomerisation of said molecules;
(iv) allowing said molecules to assemble into a polymer or oligomer via said binding moieties in the liquid medium, said liquid medium having a pH of 6.3 or lower and an ion composition that allows polymerisation or oligomerisation of said molecules;
(v) adjusting the properties of said liquid medium to a pH of 6.4 or higher and/or an ion composition that prevents polymerisation or oligomerisation of said molecules to disassemble said polymer or oligomer; and
(vi) determining the presence of binding interactions which are not mediated via said binding moieties between two or more different molecules, which form said subset of molecules.

There is also provided a novel use of one or more molecules, each comprising
   (a) at least one first binding moiety of from 100 to 160 amino acid residues which is derived from the N-terminal fragment of a spider silk protein, and
   (b) a second moiety which is individually selected from proteins, nucleic acids, carbohydrates and lipids;
for reversibly assembling a polymer or oligomer of said molecules via said binding moieties in a solution at a pH of 6.3 or lower and an ion composition that allows polymerisation or oligomerisation of said molecules.

In a preferred embodiment, the polymer or oligomer is used in interaction studies, separation, inducing activity of enzyme complexes or FRET analysis.

In another aspect, the present invention provides an affinity medium comprising a matrix and a ligand for affinity interactions coupled to said matrix, which ligand is comprising at least one fragment of from 100 to 160 amino acid residues which is derived from the N-terminal fragment of a spider silk protein.

In a preferred embodiment, the matrix is selected from the group consisting of particles and filters.

Other aspects and embodiments of the invention will be evident from the description.

BRIEF DESCRIPTION OF THE DRAWINGS

FIG. 1 shows a sequence alignment of the following spidroin N-terminal fragments: (1) Ea MaSpI (SEQ ID NO:33); (2) Lg MaSpI (SEQ ID NO:34); (3) Lh MaSpI (SEQ ID NO:35); (4) Nc MaSpI (SEQ ID NO:36); (5) At MaSp2 (SEQ ID NO:37); (6) Lg MaSp2 (SEQ ID NO:38); (7) Lh MaSp2 (SEQ ID NO:39); (8) Nim MaSp2 (SEQ ID NO:40); (9) Nc MaSp2 (SEQ ID NO:41); (10) Ab CySpI (SEQ ID NO:42); (11) NcI CySpI (SEQ ID NO:43); (12) Lh TuSpI (SEQ ID NO:44); (13) Nc Flag (SEQ ID NO:45); and (14) Nim Flag (SEQ ID NO:46).

FIG. 2 shows a sequence alignment of the following spidroin C-terminal fragments: (1) Cthyb Esp (SEQ ID NO:51); (2) CTnat Eau (SEQ ID NO:52); (3) AF350266 At1 (SEQ ID NO:53); (4) AY666062 Cm1 (SEQ ID NO:54); (5) AF350273 Lg1 (SEQ ID NO:55); (6) AY953074 Lh1 (SEQ ID NO:56); (7) AY666068 Mh1 (SEQ ID NO:57); (8) U20329 Nc1 (SEQ ID NO:58); (9) AY666076 Np1 (SEQ ID NO:59); (10) AF350277 Nm1 (SEQ ID NO:60); (11) AF350279 Ns1 (SEQ ID NO:61); (12) AY666057 Ov1 (SEQ ID NO:62); (13) AY666064 Ps1 (SEQ ID NO:63); (14) AF350285 Tk1 (SEQ ID NO:64); (15) AF350286 Tv1 (SEQ ID NO:65); (16) ABU20328 Ab2 (SEQ ID NO:66); (17) AY365016 Aam2 (SEQ ID NO:67); (18) AF350263 Aau2 (SEQ ID NO:68); (19) AF350267 At2 (SEQ ID NO:69); (20) AF350272 Gm2 (SEQ ID NO:70); (21) AF350275 Lg2 (SEQ ID NO:71); (22) AY953075 Lh2 (SEQ ID NO:72); (23) AY654293 Nc2 (SEQ ID NO:73); (24) AF350278 Nm2 (SEQ ID NO:74); (25) AF350280 Ns2 (SEQ ID NO:75); (26) AF350269 DtFb1 (SEQ ID NO:76); (27) AF350270 DtFb2 (SEQ ID NO:77); (28) U47853 ADF1 (SEQ ID NO:78); (29) U47854 ADF2 (SEQ ID NO:79); (30) U47855 ADF3 (SEQ ID NO:80); and (31) U47856 ADF4 (SEQ ID NO:81).

LIST OF APPENDED SEQUENCES

Figure 3:
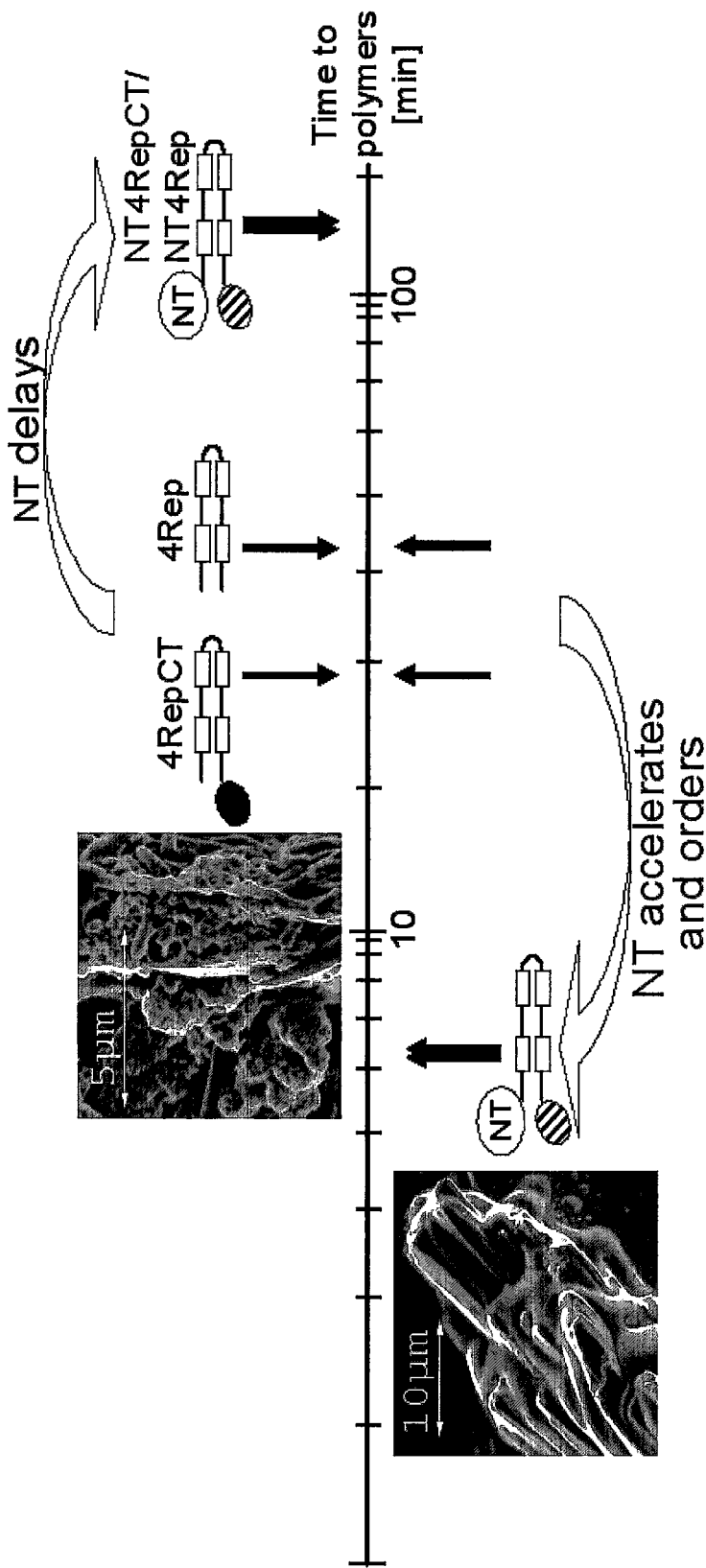
FIG. 3 illustrates the pH-induced and salt-dependent polymerisation of NT4Rep, NT4RepCT, 4Rep, and 4RepCT.

SEQ ID NO 1 4Rep
2 4RepCT
3 NT4Rep
4 NT5Rep
5 NT4RepCTHis
6 NT
7 CT
8 consensus NT sequence
9 consensus CT sequence
10 repetitive sequence from *Euprosthenops australis* MaSp1
11 consensus G segment sequence 1
12 Consensus G segment sequence 2
13 consensus G segment sequence 3
14 NT4Rep (DNA)
15 NT4RepCT (DNA)
16 NT5Rep (DNA)
17 NT4RepCTHis 2
18 NT4RepCTHis 2 (DNA)
19 ZbasicNT4RepCT
20 NT4RepCT
21 HisTrxHisThrNT4RepCT
22 NT4RepCT 2
23 HisNTNT4RepCT
24 HisNTNT4RepCT (DNA)
25 NT8RepCT
26 HisNTMetSP-C33Leu
27 HisNTMetSP-C33Leu (DNA)
28 HisNTNTMetSP-C33Leu
29 HisNTNTMetSP-C33Leu (DNA)
30 NTHis
31 NTNT8RepCT
32 NTNTBrichos
33 NT *Euprosthenops australis* MaSp1
34 NT *Latrodectus qeometricus* MaSp1
35 NT *Latrodectus hesperus* MaSp1
36 NT *Nephila clavipes* MaSp1
37 NT *Arqiope trifasciata* MaSp2
38 NT *Latrodectus qeometricus* MaSp2
39 NT *Latrodectus hesperus* MaSp2
40 NT *Nephila inaurata madaqascariensis* MaSp2
41 NT *Nephila clavipes* MaSp2
42 NT *Arqiope bruennichi* cylindriform spidroin 1
43 NT *Nephila clavata* cylindriform spidroin 1
44 NT *Latrodectus hesperus* tubuliform spidroin
45 NT *Nephila clavipes* flagelliform silk protein
46 NT *Nephila inaurata madaqascariensis* flagelliform silk
47 Linker peptide 1
48 Linker peptide 2
49 Linker peptide 3
50 Linker peptide 4
51 CT *Euprosthenops* sp MaSp1
52 CT *Euprosthenops australis* MaSp1
53 CT *Arqiope trifasciata* MaSp1
54 CT *Curtophora moluccensis* Sp1
55 CT *Latrodectus qeometricus* MaSp1
56 CT *Latrodectus hesperus* MaSp1
57 CT *Macrothele holsti* Sp1
58 CT *Nephila clavipes* MaSp1
59 CT *Nephila pilipes* MaSp1
60 CT *Nephila madaqascariensis* MaSp1
61 CT *Nephila senegalensis* MaSp1
62 CT *Octonoba varians* Sp1
63 CT *Psechrus sinensis* Sp1
64 CT *Tetracmatha kauaiensis* MaSp1
65 CT *Tetracmatha versicolor* MaSp1
66 CT *Araneus bicentenarius* Sp2
67 CT *Arqiope amoena* MaSp2
68 CT *Arqiope aurantia* MaSp2
69 CT *Arqiope trifasciata* MaSp2
70 CT *Gasteracantha mammosa* MaSp2
71 CT *Latrodectus qeometricus* MaSp2
72 CT *Latrodectus hesperus* MaSp2
73 CT *Nephila clavipes* MaSp2
74 CT *Nephila madaqascariensis* MaSp2
75 CT *Nephila senegalensis* MaSp2
76 CT *Dolomedes tenebrosus* Fb1
77 CT *Dolomedes tenebrosus* Fb2
78 CT *Araneus diadematus* ADF-1
79 CT *Araneus diadematus* ADF-2
80 CT *Araneus diadematus* ADF-3
81 CT *Araneus diadematus* ADF-4

DETAILED DESCRIPTION OF THE INVENTION

The present invention is generally based on the inventive insight that the previously poorly understood N-terminal non-repetitive fragment of spider silk proteins is involved in polymerisation of these proteins, and in particular that the formation of polymers involving this fragment can be tightly controlled by varying certain parameters. This insight has been developed into a novel method of producing polymers of an isolated spider silk protein. Although the examples by necessity relate to specific proteins, in this case proteins derived from major spidroin 1 (MaSp1) from *Euprosthenops australis*, it is considered that the method disclosed herein is applicable to any similar protein for the purpose of producing polymers.

This insight has also led to the identification of a novel spider silk protein motif, which is sufficient for recombinant production of spider silk fibers. It follows that the new spider silk protein motif is useful as a starting point for construction of novel spider silk proteins and genes, such as those reported herein. The polymers which are formed from the proteins resulting from the novel spidroins are useful for their physical properties, especially the useful combination of high strength, elasticity and light weight. They are also useful for their ability to support cell adherence and growth. The properties of dragline silk are attractive in development of new materials for medical or technical purposes. In particular, spider silks according to the invention are useful in medical devices, such as implants and medical products, such as wound closure systems, band-aids, sutures, wound dressings, and scaffolds for tissue engineering and guided cell regeneration. Spider silks according to the invention are also particularly useful for use as textile or fabric, such as in parachutes, bulletproof clothing, seat belts, etc. Using this method, it is no longer required to introduce a cleavable fusion partner that is cleaved off using cleavage agents during the process when polymerisation is desired, This facilitates the production and yield of spider silk proteins and polymers thereof, and provides an advantage in an industrial production process.

The term "fiber" as used herein relates to polymers having a thickness of at least 0.1 µm, preferably macroscopic polymers that are visible to the human eye, i.e. having a thickness of at least 1 µm, and have a considerable extension in length compared to its thickness, preferably above 5 mm. The term "fiber" does not encompass unstructured aggregates or precipitates.

The terms "spidroins" and "spider silk proteins" are used interchangeably throughout the description and encompass all known spider silk proteins, including major ampullate spider silk proteins which typically are abbreviated "MaSp", or "ADF" in the case of *Araneus diadematus*. These major ampullate spider silk proteins are generally of two types, 1 and 2. These terms furthermore include the new proteins according to the invention, as defined in the appended claims and itemized embodiments, and other non-natural proteins with a high degree of identity and/or similarity to the known spider silk proteins.

The present invention thus provides a method of producing polymers of an isolated spider silk protein. In the first step, a recombinant spider silk protein is provided. The spider silk protein typically consists of from 170 to 760 amino acid residues, such as from 170 to 600 amino acid residues, preferably from 280 to 600 amino acid residues, such as from 300 to 400 amino acid residues, more preferably from 340 to 380 amino acid residues. The small size is advantageous because longer spider silk proteins tend to form amorphous aggregates, which require use of harsh solvents for solubilisation and polymerisation. The recombinant spider silk protein may contain more than 760 residues, in particular in cases where the spider silk protein contains more than two fragments derived from the N-terminal part of a spider silk protein. The spider silk protein comprises an N-terminal fragment consisting of at least one fragment (NT) derived from the corresponding part of a spider silk protein, and a repetitive fragment (REP) derived from the corresponding internal fragment of a spider silk protein. Optionally, the spider silk protein comprises a C-terminal fragment (CT) derived from the corresponding fragment of a spider silk protein. The spider silk protein comprises typically a single fragment (NT) derived from the N-terminal part of a spider silk protein, but in preferred embodiments, the N-terminal fragment include at least two, such as two fragments (NT) derived from the N-terminal part of a spider silk protein. Thus, the spidroin can schematically be represented by the formula $NT_m$-REP, and alternatively $NT_m$-REP-CT, where m is an integer that is 1 or higher, such as 2 or higher, preferably in the ranges of 1-2, 1-4, 1-6, 2-4 or 2-6. Preferred spidroins can schematically be represented by the formulas $NT_2$-REP or NT-REP, and alternatively $NT_2$-REP-CT or NT-REP-CT. The protein fragments are covalently coupled, typically via a peptide bond. In one embodiment, the spider silk protein consists of the NT fragment(s) coupled to the REP fragment, which REP fragment is optionally coupled to the CT fragment.

The NT fragment has a high degree of similarity to the N-terminal amino acid sequence of spider silk proteins. As shown in FIG. 1, this amino acid sequence is well conserved among various species and spider silk proteins, including MaSp1 and MaSp2. In FIG. 1, the following spidroin NT fragments are aligned, denoted with GenBank accession entries where applicable:

TABLE 1

Spidroin NT fragments

| Code | Species and spidroin protein | GenBank acc. no. |
|---|---|---|
| Ea MaSp1 | *Euprosthenops australis* MaSp 1 | AM259067 |
| Lg MaSp1 | *Latrodectus geometricus* MaSp 1 | ABY67420 |

TABLE 1-continued

Spidroin NT fragments

| Code | Species and spidroin protein | GenBank acc. no. |
|---|---|---|
| Lh MaSp1 | *Latrodectus hesperus* MaSp 1 | ABY67414 |
| Nc MaSp1 | *Nephila clavipes* MaSp 1 | ACF19411 |
| At MaSp2 | *Argiope trifasciata* MaSp 2 | AAZ15371 |
| Lg MaSp2 | *Latrodectus geometricus* MaSp 2 | ABY67417 |
| Lh MaSp2 | *Latrodectus hesperus* MaSp 2 | ABR68855 |
| Nim MaSp2 | *Nephila inaurata madagascariensis* MaSp 2 | AAZ15322 |
| Nc MaSp2 | *Nephila clavipes* MaSp 2 | ACF19413 |
| Ab CySp1 | *Argiope bruennichi* cylindriform spidroin 1 | BAE86855 |
| Ncl CySp1 | *Nephila clavata* cylindriform spidroin 1 | BAE54451 |
| Lh TuSp1 | *Latrodectus hesperus* tubuliform spidroin | ABD24296 |
| Nc Flag | *Nephila clavipes* flagelliform silk protein | AF027972 |
| Nim Flag | *Nephila inaurata madagascariensis* flagelliform silk protein | AF218623 (translated) |

Only the part corresponding to the N-terminal fragment is shown for each sequence, omitting the signal peptide. Nc flag and Nlm flag are translated and edited according to Rising A. et al. Biomacromolecules 7, 3120-3124 (2006)).

It is observed that NT has a clear dipole moment as acidic and basic residues are localized in clusters at opposite poles. Without desiring to be limited thereto, it is contemplated that the observed polymerisation of NT may involve the formation of linear arrays of NT dimers, stacked pole-to-pole with the negative surface of one subunit facing the positive surface of the neighbouring subunit in the next dimer in the array.

It is not critical which specific NT fragment is present in spider silk proteins according to the invention, as long as the NT fragment is not entirely missing. Thus, the NT fragment according to the invention can be selected from any of the amino acid sequences shown in FIG. 1 or sequences with a high degree of similarity. A wide variety of N-terminal sequences can be used in the spider silk protein according to the invention. Based on the homologous sequences of FIG. 1, the following sequence constitutes a consensus NT amino acid sequence:

(SEQ ID NO: 8)
QANTPWSSPNLADAFINSF(M/L)SA(A/I)SSSGAFSADQLDDMSTIG (D/N/Q)TLMSAMD(N/S/K)MGRSG(K/R)STKSKLQALNMAFASSMA

EIAAAESGG(G/Q)SVGVKTNAISDALSSAFYQTTGSVNPQFV(N/S)E

IRSLI(G/N)M(F/L)(A/S)QASANEV.

The sequence of the NT fragment according to the invention has at least 50% identity, preferably at least 60% identity, to the consensus amino acid sequence SEQ ID NO: 8, which is based on the amino acid sequences of FIG. 1. In a preferred embodiment, the sequence of the NT fragment according to the invention has at least 65% identity, preferably at least 70% identity, to the consensus amino acid sequence SEQ ID NO: 8. In preferred embodiments, the NT fragment according to the invention has furthermore 70%, preferably 80%, similarity to the consensus amino acid sequence SEQ ID NO: 8.

A representative NT fragment according to the invention is the *Euprosthenops australis* sequence SEQ ID NO: 6. According to a preferred embodiment of the invention, the NT fragment has at least 80% identity to SEQ ID NO: 6 or any individual amino acid sequence in FIG. 1. In preferred embodiments of the invention, the NT fragment has at least 90%, such as at least 95% identity, to SEQ ID NO: 6 or any individual amino acid sequence in FIG. 1. In preferred embodiments of the invention, the NT fragment is identical to SEQ ID NO: 6 or any individual amino acid sequence in FIG. 1, in particular to Ea MaSp1.

The NT fragment contains from 100 to 160 amino acid residues. It is preferred that the NT fragment contains at least 100, or more than 110, preferably more than 120, amino acid residues. It is also preferred that the NT fragment contains at most 160, or less than 140 amino acid residues. A typical NT fragment contains approximately 130-140 amino acid residues.

When the N-terminal fragment of the spider silk protein contains two or more fragments (NT) derived from the N-terminal fragment of a spider silk protein, it may also contain one or more linker peptides. The linker peptide(s) may be arranged between two NT fragments and provide a spacer.

The protein fragment REP has a repetitive character, alternating between alanine-rich stretches and glycine-rich stretches. The REP fragment generally contains more than 70, such as more than 140, and less than 300, preferably less than 240, such as less than 200, amino acid residues, and can itself be divided into several L (linker) segments, A (alanine-rich) segments and G (glycine-rich) segments, as will be explained in more detail below. Typically, said linker segments, which are optional, are located at the REP fragment terminals, while the remaining segments are in turn alanine-rich and glycine-rich. Thus, the REP fragment can generally have either of the following structures, wherein n is an integer:
$L(AG)_nL$, such as $LA_1G_1A_2G_2A_3G_3A_4G_4A_5G_5L$;
$L(AG)_nAL$, such as $LA_1G_1A_2G_2A_3G_3A_4G_4A_5G_5A_6L$;
$L(GA)_nL$, such as $LG_1A_1G_2A_2G_3A_3G_4A_4G_5A_5L$; or
$L(GA)_nGL$, such as $LG_1A_1G_2A_2G_3A_3G_4A_4G_5A_5G_6L$.

It follows that it is not critical whether an alanine-rich or a glycine-rich segment is adjacent to the N-terminal or C-terminal linker segments. It is preferred that n is an integer from 2 to 10, preferably from 2 to 8, preferably from 4 to 8, more preferred from 4 to 6, i.e. n=4, n=5 or n=6.

In preferred embodiments, the alanine content of the REP fragment according to the invention is above 20%, preferably above 25%, more preferably above 30%, and below 50%, preferably below 40%, more preferably below 35%. This is advantageous, since it is contemplated that a higher alanine content provides a stiffer and/or stronger and/or less extendible fiber.

In certain embodiments, the REP fragment is void of proline residues, i.e. there are no Pro residues in the REP fragment.

Now turning to the segments that constitute the REP fragment according to the invention, it shall be emphasized that each segment is individual, i.e. any two A segments, any two G segments or any two L segments of a specific REP fragment may be identical or may not be identical. Thus, it is not a general feature of the invention that each type of segment is identical within a specific REP fragment. Rather, the following disclosure provides the skilled person with guidelines how to design individual segments and gather them into a REP fragment, which is a part of a functional spider silk protein according to the invention.

Each individual A segment is an amino acid sequence having from 8 to 18 amino acid residues. It is preferred that each individual A segment contains from 13 to 15 amino acid residues. It is also possible that a majority, or more than two, of the A segments contain from 13 to 15 amino acid residues, and that a minority, such as one or two, of the A segments contain from 8 to 18 amino acid residues, such as 8-12 or 16-18 amino acid residues. A vast majority of these amino acid residues are alanine residues. More specifically, from 0 to 3 of the amino acid residues are not alanine residues, and the remaining amino acid residues are alanine residues. Thus, all amino acid residues in each individual A segment are alanine residues, with no exception or the exception of one, two or three amino acid residues, which can be any amino acid. It is preferred that the alanine-replacing amino acid(s) is (are) natural amino acids, preferably individually selected from the group of serine, glutamic acid, cysteine and glycine, more preferably serine. Of course, it is possible that one or more of the A segments are all-alanine segments, while the remaining A segments contain 1-3 non-alanine residues, such as serine, glutamic acid, cysteine or glycine.

In a preferred embodiment, each A segment contains 13-15 amino acid residues, including 10-15 alanine residues and 0-3 non-alanine residues as described above. In a more preferred embodiment, each A segment contains 13-15 amino acid residues, including 12-15 alanine residues and 0-1 non-alanine residues as described above.

It is preferred that each individual A segment has at least 80%, preferably at least 90%, more preferably 95%, most preferably 100% identity to an amino acid sequence selected from the group of amino acid residues 7-19, 43-56, 71-83, 107-120, 135-147, 171-183, 198-211, 235-248, 266-279, 294-306, 330-342, 357-370, 394-406, 421-434, 458-470, 489-502, 517-529, 553-566, 581-594, 618-630, 648-661, 676-688, 712-725, 740-752, 776-789, 804-816, 840-853, 868-880, 904-917, 932-945, 969-981, 999-1013, 1028-1042 and 1060-1073 of SEQ ID NO: 10. Each sequence of this group corresponds to a segment of the naturally occurring sequence of *Euprosthenops australis* MaSp1 protein, which is deduced from cloning of the corresponding cDNA, see WO 2007/078239. Alternatively, each individual A segment has at least 80%, preferably at least 90%, more preferably 95%, most preferably 100% identity to an amino acid sequence selected from the group of amino acid residues 143-152, 174-186, 204-218, 233-247 and 265-278 of SEQ ID NO: 3. Each sequence of this group corresponds to a segment of expressed, non-natural spider silk proteins according to the invention, which proteins have capacity to form silk fibers under appropriate conditions (see Example 2). Thus, in certain embodiments according to the invention, each individual A segment is identical to an amino acid sequence selected from the above-mentioned amino acid segments. Without wishing to be bound by any particular theory, it is envisaged that A segments according to the invention form helical structures or beta sheets.

The term "% identity", as used throughout the specification and the appended claims, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). A comparison is made over the window corresponding to the shortest of the aligned sequences. The amino acid residues at each position are compared, and the percentage of positions in the query sequence that have identical correspondences in the target sequence is reported as % identity.

The term "% similarity", as used throughout the specification and the appended claims, is calculated as described for "% identity", with the exception that the hydrophobic residues Ala, Val, Phe, Pro, Leu, Ile, Trp, Met and Cys are similar; the basic residues Lys, Arg and His are similar; the acidic residues Glu and Asp are similar; and the hydrophilic, uncharged residues Gln, Asn, Ser, Thr and Tyr are similar. The remaining natural amino acid Gly is not similar to any other amino acid in this context.

Throughout this description, alternative embodiments according to the invention fulfill, instead of the specified percentage of identity, the corresponding percentage of similarity. Other alternative embodiments fulfill the specified percentage of identity as well as another, higher percentage of similarity, selected from the group of preferred percentages of identity for each sequence. For example, a sequence may be 70% similar to another sequence; or it may be 70% identical to another sequence; or it may be 70% identical and 90% similar to another sequence.

Furthermore, it has been concluded from experimental data that each individual G segment is an amino acid sequence of from 12 to 30 amino acid residues. It is preferred that each individual G segment consists of from 14 to 23 amino acid residues. At least 40% of the amino acid residues of each G segment are glycine residues. Typically the glycine content of each individual G segment is in the range of 40-60%.

It is preferred that each individual G segment has at least 80%, preferably at least 90%, more preferably 95%, most preferably 100% identity to an amino acid sequence selected from the group of amino acid residues 20-42, 57-70, 84-106, 121-134, 148-170, 184-197, 212-234, 249-265, 280-293, 307-329, 343-356, 371-393, 407-420, 435-457, 471-488, 503-516, 530-552, 567-580, 595-617, 631-647, 662-675, 689-711, 726-739, 753-775, 790-803, 817-839, 854-867, 881-903, 918-931, 946-968, 982-998, 1014-1027, 1043-1059 and 1074-1092 of SEQ ID NO: 10. Each sequence of this group corresponds to a segment of the naturally occurring sequence of *Euprosthenops australis* MaSp1 protein, which is deduced from cloning of the corresponding cDNA, see WO 2007/078239. Alternatively, each individual G segment has at least 80%, preferably at least 90%, more preferably 95%, most preferably 100% identity to an amino acid sequence selected from the group of amino acid residues 153-173, 187-203, 219-232, 248-264 and 279-296 of SEQ ID NO: 3. Each sequence of this group corresponds to a segment of expressed, non-natural spider silk proteins according to the invention, which proteins have capacity to form silk fibers under appropriate conditions (see Example 2). Thus, in certain embodiments according to the invention, each individual G segment is identical to an amino acid sequence selected from the above-mentioned amino acid segments.

In certain embodiments, the first two amino acid residues of each G segment according to the invention are not -Gln-Gln-.

There are the three subtypes of the G segment according to the invention. This classification is based upon careful analysis of the *Euprosthenops australis* MaSp1 protein sequence (WO 2007/078239), and the information has been employed and verified in the construction of novel, non-natural spider silk proteins.

The first subtype of the G segment according to the invention is represented by the amino acid one letter consensus sequence GQG(G/S)QGG(Q/Y)GG (L/Q)GQGGYGQGA GSS (SEQ ID NO: 11). This first, and generally the longest, G segment subtype typically contains 23 amino acid residues, but may contain as little as 17 amino acid residues, and lacks charged residues or contain one charged residue. Thus, it is preferred that this first G segment subtype contains 17-23 amino acid residues, but it is contemplated that it may contain as few as 12 or as many as 30 amino acid residues. Without wishing to be bound by any particular theory, it is envisaged that this subtype forms coil structures or $3_1$-helix structures. Representative G segments of this first subtype are amino acid residues 20-42, 84-106, 148-170, 212-234, 307-329, 371-393, 435-457, 530-552, 595-617, 689-711, 753-775, 817-839, 881-903, 946-968, 1043-1059 and 1074-1092 of SEQ ID NO: 10. In certain embodiments, the first two amino acid residues of each G segment of this first subtype according to the invention are not -Gln-Gln-.

The second subtype of the G segment according to the invention is represented by the amino acid one letter consensus sequence GQGGQGQG(G/R)Y GQG(A/S)G(S/G)S (SEQ ID NO: 12). This second, generally mid-sized, G segment subtype typically contains 17 amino acid residues and lacks charged residues or contain one charged residue. It is preferred that this second G segment subtype contains 14-20 amino acid residues, but it is contemplated that it may contain as few as 12 or as many as 30 amino acid residues. Without wishing to be bound by any particular theory, it is envisaged that this subtype forms coil structures. Representative G segments of this second subtype are amino acid residues 249-265, 471-488, 631-647 and 982-998 of SEQ ID NO: 10; and amino acid residues 187-203 of SEQ ID NO: 3.

The third subtype of the G segment according to the invention is represented by the amino acid one letter consensus sequence G(R/Q)GQG(G/R)YGQG (A/S/V)GGN (SEQ ID NO: 13). This third G segment subtype typically contains 14 amino acid residues, and is generally the shortest of the G segment subtypes according to the invention. It is preferred that this third G segment subtype contains 12-17 amino acid residues, but it is contemplated that it may contain as many as 23 amino acid residues. Without wishing to be bound by any particular theory, it is envisaged that this subtype forms turn structures. Representative G segments of this third subtype are amino acid residues 57-70, 121-134, 184-197, 280-293, 343-356, 407-420, 503-516, 567-580, 662-675, 726-739, 790-803, 854-867, 918-931, 1014-1027 of SEQ ID NO: 10; and amino acid residues 219-232 of SEQ ID NO: 3.

Thus, in preferred embodiments, each individual G segment has at least 80%, preferably 90%, more preferably 95%, identity to an amino acid sequence selected from SEQ ID NO: 11, SEQ ID NO: 12 and SEQ ID NO: 13.

In a preferred embodiment of the alternating sequence of A and G segments of the REP fragment, every second G segment is of the first subtype, while the remaining G segments are of the third subtype, e.g. . . . $A_1G_{short}A_2G_{long}A_3G_{short}A_4G_{long}A_5G_{short}$ . . . . In another preferred embodiment of the REP fragment, one G segment of the second subtype interrupts the G segment regularity via an insertion, e.g. . . . $A_1G_{short}A_2G_{long}A_3G_{mid}A_4G_{short}A_5G_{long}$ . . . .

Each individual L segment represents an optional linker amino acid sequence, which may contain from 0 to 20 amino acid residues, such as from 0 to 10 amino acid residues. While this segment is optional and not functionally critical for the spider silk protein, its presence still allows for fully functional spider silk proteins, forming spider silk fibers according to the invention. There are also linker amino acid sequences present in the repetitive part (SEQ ID NO: 10) of the deduced amino acid sequence of the MaSp1 protein from *Euprosthenops australis*. In particular, the amino acid sequence of a linker segment may resemble any of the described A or G segments, but usually not sufficiently to meet their criteria as defined herein.

As shown in WO 2007/078239, a linker segment arranged at the C-terminal part of the REP fragment can be represented by the amino acid one letter consensus sequences ASASAAASAA STVANSVS (SEQ ID NO:47) and ASAASAAA (SEQ ID NO:48), which are rich in alanine. In fact, the second sequence can be considered to be an A segment according to the invention, while the first sequence has a high degree of similarity to A segments according to the invention. Another example of a linker segment according the invention has the one letter amino acid sequence GSAMGQGS (SEQ ID NO:49), which is rich in glycine and has a high degree of similarity to G segments according to the invention. Another example of a linker segment is SASAG (SEQ ID NO:50).

Representative L segments are amino acid residues 1-6 and 1093-1110 of SEQ ID NO: 10; and amino acid residues 138-142 of SEQ ID NO: 3, but the skilled person in the art will readily recognize that there are many suitable alternative amino acid sequences for these segments. In one embodiment of the REP fragment according to the invention, one of the L segments contains 0 amino acids, i.e. one of the L segments is void. In another embodiment of the REP fragment according to the invention, both L segments contain 0 amino acids, i.e. both L segments are void. Thus, these embodiments of the REP fragments according to the invention may be schematically represented as follows: $(AG)_nL$, $(AG)_nAL$, $(GA)_nL$, $(GA)_nGL$; $L(AG)_n$, $L(AG)_nA$, $L(GA)_n$, $L(GA)_nG$; and $(AG)_n$, $(AG)_nA$, $(GA)_n$, $(GA)_nG$. Any of these REP fragments are suitable for use with any CT fragment as defined below.

The optional CT fragment of the spider silk protein according to the invention has a high degree of similarity to the C-terminal amino acid sequence of spider silk proteins. As shown in WO 2007/078239, this amino acid sequence is well conserved among various species and spider silk proteins, including MaSp1 and MaSp2. A consensus sequence of the C-terminal regions of MaSp1 and MaSp2 is provided as SEQ ID NO: 9. In FIG. 2, the following MaSp proteins are aligned, denoted with GenBank accession entries where applicable:

TABLE 2

Spidroin CT fragments

| Species and spidroin protein | Entry |
|---|---|
| *Euprosthenops* sp MaSp1 (Pouchkina-Stantcheva, NN & McQueen-Mason, SJ, ibid) | Cthyb_Esp |
| *Euprosthenops australis* MaSp1 | CTnat_Eau |
| *Argiope trifasciata* MaSp1 | AF350266_At1 |
| *Cyrtophora moluccensis* Sp1 | AY666062_Cm1 |
| *Latrodectus geometricus* MaSp1 | AF350273_Lg1 |
| *Latrodectus hesperus* MaSp1 | AY953074_Lh1 |
| *Macrothele holsti* Sp1 | AY666068_Mh1 |
| *Nephila clavipes* MaSp1 | U20329_Nc1 |
| *Nephila pilipes* MaSp1 | AY666076_Np1 |
| *Nephila madagascariensis* MaSp1 | AF350277_Nm1 |
| *Nephila senegalensis* MaSp1 | AF350279_Ns1 |
| *Octonoba varians* Sp1 | AY666057_Ov1 |
| *Psechrus sinensis* Sp1 | AY666064_Ps1 |
| *Tetragnatha kauaiensis* MaSp1 | AF350285_Tk1 |
| *Tetragnatha versicolor* MaSp1 | AF350286_Tv1 |
| *Araneus bicentenarius* Sp2 | ABU20328_Ab2 |
| *Argiope amoena* MaSp2 | AY365016_Aam2 |
| *Argiope aurantia* MaSp2 | AF350263_Aau2 |
| *Argiope trifasciata* MaSp2 | AF350267_At2 |
| *Gasteracantha mammosa* MaSp2 | AF350272_Gm2 |
| *Latrodectus geometricus* MaSp2 | AF350275_Lg2 |
| *Latrodectus hesperus* MaSp2 | AY953075_Lh2 |
| *Nephila clavipes* MaSp2 | AY654293_Nc2 |
| *Nephila madagascariensis* MaSp2 | AF350278_Nm2 |
| *Nephila senegalensis* MaSp2 | AF350280_Ns2 |
| *Dolomedes tenebrosus* Fb1 | AF350269_DtFb1 |
| *Dolomedes tenebrosus* Fb2 | AF350270_DtFb2 |
| *Araneus diadematus* ADF-1 | U47853_ADF1 |
| *Araneus diadematus* ADF-2 | U47854_ADF2 |
| *Araneus diadematus* ADF-3 | U47855_ADF3 |
| *Araneus diadematus* ADF-4 | U47856_ADF4 |

It is not critical which specific CT fragment, if any, is present in spider silk proteins according to the invention. Thus, the CT fragment according to the invention can be selected from any of the amino acid sequences shown in FIG. 2 and Table 2 or sequences with a high degree of similarity. A wide variety of C-terminal sequences can be used in the spider silk protein according to the invention.

The sequence of the CT fragment according to the invention has at least 50% identity, preferably at least 60%, more preferably at least 65% identity, or even at least 70% identity, to the consensus amino acid sequence SEQ ID NO: 9, which is based on the amino acid sequences of FIG. 2.

A representative CT fragment according to the invention is the *Euprosthenops australis* sequence SEQ ID NO: 7, Thus, according to a preferred aspect of the invention, the CT fragment has at least 80%, preferably at least 90%, such as at least 95%, identity to SEQ ID NO: 7 or any individual amino acid sequence of FIG. 2 and Table 2. In preferred aspects of the invention, the CT fragment is identical to SEQ ID NO: 7 or any individual amino acid sequence of FIG. 2 and Table 2.

The CT fragment typically consists of from 70 to 120 amino acid residues. It is preferred that the CT fragment contains at least 70, or more than 80, preferably more than 90, amino acid residues. It is also preferred that the CT fragment contains at most 120, or less than 110 amino acid residues. A typical CT fragment contains approximately 100 amino acid residues.

In one embodiment, the first step of the method of producing polymers of an isolated spider silk protein involves expression of a polynucleic acid molecule which encodes the spider silk protein in a suitable host, such as *Escherichia coli*. The thus obtained protein is isolated using standard procedures. Optionally, lipopolysaccharides and other pyrogens are actively removed at this stage.

In the second step of the method of producing polymers of an isolated spider silk protein, a solution of the spider silk protein in a liquid medium is provided. By the terms "soluble" and "in solution" is meant that the protein is not visibly aggregated and does not precipitate from the solvent at 60 000×g. The liquid medium can be any suitable medium, such as an aqueous medium, preferably a physiological medium, typically a buffered aqueous medium, such as a 10-50 mM Tris-HCl buffer or phosphate buffer. The liquid medium has a pH of 6.4 or higher and/or an ion composition that prevents polymerisation of the spider silk protein. That is, the liquid medium has either a pH of 6.4 or higher or an ion composition that prevents polymerisation of the spider silk protein, or both.

Ion compositions that prevent polymerisation of the spider silk protein can readily be prepared by the skilled person utilizing the methods disclosed herein. A preferred ion composition that prevents polymerisation of the spider silk protein has an ionic strength of more than 300 mM. Specific examples of ion compositions that prevent polymerisation of the spider silk protein include above 300 mM NaCl, 100 mM phosphate and combinations of these ions having desired preventive effect on the polymerisation of the spider silk protein, e.g. a combination of 10 mM phosphate and 300 mM NaCl.

It has been surprisingly been found that the presence of an NT fragment improves the stability of the solution and prevents polymer formation under these conditions. This can be advantageous when immediate polymerisation may be undesirable, e.g. during protein purification, in preparation of large batches, or when other conditions need to be optimized. It is preferred that the pH of the liquid medium is adjusted to 6.7 or higher, such as 7.0 or higher, or even 8.0 or higher, such as up to 10.5, to achieve high solubility of the spider silk protein. It can also be advantageous that the pH of the liquid medium is adjusted to the range of 6.4-6.8, which provides sufficient solubility of the spider silk protein but facilitates subsequent pH adjustment to 6.3 or lower.

In the third step, the properties of the liquid medium are adjusted to a pH of 6.3 or lower and ion composition that allows polymerisation. That is, if the liquid medium wherein the spider silk protein is dissolved has a pH of 6.4 or higher, the pH is decreased to 6.3 or lower. The skilled person is well aware of various ways of achieving this, typically involving addition of a strong or weak acid. If the liquid medium wherein the spider silk protein is dissolved has an ion composition that prevents polymerisation, the ion composition is changed so as to allow polymerisation. The skilled person is well aware of various ways of achieving this, e.g. dilution, dialysis or gel filtration. If required, this step involves both decreasing the pH of the liquid medium to 6.3 or lower and changing the ion composition so as to allow polymerisation. It is preferred that the pH of the liquid medium is adjusted to 6.2 or lower, such as 6.0 or lower. In particular, it may be advantageous from a practical point of view to limit the pH drop from 6.4 or 6.4-6.8 in the preceding step to 6.3 or 6.0-6.3, e.g. 6.2 in this step. In a preferred embodiment, the pH of the liquid medium of this step is 3 or higher, such as 4.2 or higher. The resulting pH range, e.g. 4.2-6.3 promotes rapid polymerisation, In the fourth step, the spider silk protein is allowed to polymerise in the liquid medium having pH of 6.3 or lower and an ion composition that allows polymerisation of the spider silk protein. It has surprisingly been found that although the presence of the NT fragment improves solubility of the spider silk protein at a pH of 6.4 or higher and/or an ion composition that prevents polymerisation of the spider silk protein, it accelerates polymer formation at a pH of 6.3 or lower when the ion composition allows polymerisation of the spider silk protein. The resulting polymers are preferably solid and macroscopic, and they are formed in the liquid medium having a pH of 6.3 or lower and an ion composition that allows polymerisation of the spider silk protein. In a preferred embodiment, the pH of the liquid medium of this step is 3 or higher, such as 4.2 or higher. The resulting pH range, e.g. 4.2-6.3 promotes rapid polymerisation, Preferred polymer shapes include a fiber, film, foam, net or mesh. It is preferred that the polymer is a fiber having a diameter of more than 0.1 µm, preferably more than 1 µm, and a length of more than 5 mm.

Ion compositions that allow polymerisation of the spider silk protein can readily be prepared by the skilled person utilizing the methods disclosed herein. A preferred ion composition that allows polymerisation of the spider silk protein has an ionic strength of less than 300 mM. Specific examples of ion compositions that allow polymerisation of the spider silk protein include 150 mM NaCl, 10 mM phosphate, 20 mM phosphate and combinations of these ions lacking preventive effect on the polymerisation of the spider silk protein, e.g. a combination of 10 mM phosphate or 20 mM phosphate and 150 mM NaCl. It is preferred that the ionic strength of this liquid medium is adjusted to the range of 1-250 mM.

Without desiring to be limited to any specific theory, it is envisaged that the NT fragments have oppositely charged poles, and that environmental changes in pH affects the charge balance on the surface of the protein followed by polymerisation, whereas salt inhibits the same event.

At neutral pH, the energetic cost of burying the excess negative charge of the acidic pole may be expected to prevent polymerisation. However, as the dimer approaches its isoelectric point at lower pH, attractive electrostatic forces will eventually become dominant, explaining the observed salt and pH-dependent polymerisation behaviour of NT and NT-containing minispidroins. We propose that pH-induced NT polymerisation, and increased efficiency of fiber assembly of NT-minispidroins, are due to surface electrostatic potential changes, and that clustering of acidic residues at one pole of NT shifts its charge balance such that the polymerisation transition occurs at pH values of 6.3 or lower.

In the fifth and final step, the resulting, preferably solid spider silk protein polymers are isolated from said liquid medium. Optionally, this step involves actively removing lipopolysaccharides and other pyrogens from the spidroin polymers.

Without desiring to be limited to any specific theory, it has been observed that formation of spidroin polymers progresses via formation of water-soluble spidroin dimers. The present invention thus also provides a method of producing dimers of an isolated spider silk protein, wherein the first two method steps are as described above. The spider silk protein are present as dimers in a liquid medium at a pH of 6.4 or higher and/or an ion composition that prevents polymerisation of said spider silk protein. The third step involves isolating the dimers obtained in the second step, and optionally removal of lipopolysaccharides and other pyrogens. In a preferred embodiment, the spider silk protein polymer of the invention consists of polymerised protein dimers. The present invention thus provides a novel use of a spider silk protein, preferably those disclosed herein, for producing dimers of the spider silk protein.

According to another aspect, the present invention provides a polymer of a spider silk protein as disclosed herein. In a preferred embodiment, the polymer of this protein is obtainable by any one of the methods therefor according to the invention. Thus, the present invention provides a novel use of a spider silk protein, preferably those disclosed herein, for producing polymers of the spider silk protein. According to one embodiment, the present invention provides a novel use of a dimer of a spider silk protein, preferably those disclosed herein, for producing polymers of the isolated spider silk protein. In these uses, it is preferred that the polymers are produced in a liquid medium having a pH of 6.3 or lower and an ion composition that allows polymerisation of said spider silk protein. In a preferred embodiment, the pH of the liquid medium is 3 or higher, such as 4.2 or higher. The resulting pH range, e.g. 4.2-6.3 promotes rapid polymerisation, Using the method(s) of the present invention, it is possible to control the polymerization process, and this allows for optimization of parameters for obtaining silk polymers with desirable properties and shapes.

It is preferable that the polymer of the spidroin protein according to the invention is a fiber with a macroscopic size, i.e. with a diameter above 0.1 µm, preferably above 1 µm, and a length above 5 mm. It is preferred that the fiber has a diameter in the range of 1-400 µm, preferably 60-120 µm, and a length in the range of 0.5-300 cm, preferably 1-100 cm. Other preferred ranges are 0.5-30 cm and 1-20 cm. It is also preferred that the polymer, such as a fiber, of the spidroin protein according to the invention has a tensile strength above 1 MPa, preferably above 2 MPa, more preferably 10 MPa or higher. It is preferred that the polymer, such as a fiber, of the spidroin protein according to the invention has a tensile strength above 100 MPa, more preferably 200 MPa or higher. The fiber has the capacity to remain intact during physical manipulation, i.e. can be used for spinning, weaving, twisting, crocheting and similar procedures.

In other preferred embodiments, the polymer of the spidroin protein according to the invention forms a foam, a net, a mesh or a film.

According to another aspect, the present invention provides an isolated polynucleic acid molecule comprising a nucleic acid sequence which encodes a spider silk protein according to the invention, or its complementary nucleic acid sequence, such as SEQ ID NO: 14-16. These polynucleic acid molecules as well as polynucleic acid molecules coding for the various proteins disclosed herein (SEQ ID NO: 1-7, 10-13) may also be useful in further developments of non-natural spidroin proteins or production systems therefor.

Polynucleic acid molecules according to the invention can be DNA molecules, including cDNA molecules, or RNA molecules. As the skilled person is well aware, a nucleic acid sequence may as well be described by its complementary nucleic acid sequence. Therefore, nucleic acid sequences that are complementary to the nucleic acid sequences according to the invention are also encompassed by the protective scope of the invention.

According to one aspect, the present invention provides a method of producing a spider silk protein according to the invention. In the first step, a polynucleic acid molecule which encodes a spider silk protein according to the invention is expressed in a suitable host. In the second step, the thus obtained soluble spider silk protein is isolated, e.g. using chromatography and/or filtration. Optionally, said second step of isolating the soluble spider silk protein involves removal of LPS and other pyrogens.

The spider silk protein according to the invention is typically recombinantly produced using a variety of suitable hosts, such as bacteria, yeast, mammalian cells, plants, insect cells, and transgenic animals. It is preferred that the spider silk protein according to the invention is produced in bacteria.

In order to obtain a protein with low pyrogenic content, which is an obligate for usage as a biomaterial in vivo, a purification protocol optimized for removal of lipopolysaccharides (LPS) has been developed. To avoid contamination by released LPS, the producing bacterial cells are subjected to washing steps with altering $CaCl_2$ and EDTA. After cell lysis, all subsequent purifications steps are performed in low conductivity buffers in order to minimize hydrophobic interactions between the target protein and LPS. The LPS content is further minimized by passage of the protein solution through an Endotrap column, which has a ligand that specifically adsorbs LPS. To assure constant low content of LPS and other pyrogens, all batches are analyzed using an in vitro pyrogen test (IPT) and/or a *Limulus amebocyte* lysate (LAL) kinetic assay. Although produced in a gram-negative bacterial host, the recombinant spidroin proteins can be purified so that residual levels of LPS and other pyrogens are below the limits required for animal tests, i.e. below 25 EU/implant. In certain embodiments according to the invention, the content of LPS and other pyrogens in the isolated spider silk protein is 1 EU/mg protein or lower. In certain embodiments according to the invention, the content of LPS and other pyrogens in the isolated spider silk protein is 1 EU/mg protein or lower, preferably 0.25 EU/mg protein or lower.

According to one aspect, the present invention provides a composition comprising an isolated spider silk protein, preferably those disclosed herein, dissolved in a liquid medium having a pH of 6.4 or higher and/or an ion composition that prevents polymerisation of said spider silk protein. The liquid medium can be any suitable medium, such as an aqueous medium, preferably a physiological medium, typically a buffered aqueous medium, such as a 10-50 mM Tris-HCl buffer or phosphate buffer. The liquid medium has a pH of 6.4 or higher and/or an ion composition that prevents polymerisation of the spider silk protein. That is, the liquid medium has either a pH of 6.4 or higher or an ion composition that prevents polymerisation of the spider silk protein, or both. A preferred ion composition that prevents polymerisation of the spider silk protein has an ionic strength of more than 300 mM. Specific examples of ion compositions that prevent polymerisation of the spider silk protein include above 300 mM NaCl, 100 mM phosphate and combinations of these ions having desired preventive effect on the polymerisation of the spider silk protein, e.g. a combination of 10 mM phosphate and 300 mM NaCl. It is preferred that the pH of the liquid medium is 6.7 or higher, such as 7.0 or higher, or even 8.0 or higher, such as up to 10.5, to achieve high solubility of the spider silk protein. It can also be advantageous that the pH of the liquid medium is in the range of 6.4-6.8, which provides sufficient solubility of the spider silk protein but facilitates subsequent pH adjustment to 6.3 or lower. It is preferred that the content of lipopolysaccharides and other pyrogens is 1 EU/mg of isolated protein or lower in the liquid medium.

The inventive insights that the N-terminal non-repetitive fragment of spider silk proteins is involved in polymerisation of these proteins and that the formation of polymers involving this fragment can be tightly controlled by varying certain parameters have also been developed into a novel method of reversibly assembling a polymer or oligomer of molecules carrying at least one fragment derived from N-terminal non-repetitive spidroin fragments. Although the examples by necessity relate to specific proteins, in this case containing N-terminal protein fragments derived from major spidroin 1 (MaSp1) from *Euprosthenops australis*, it is considered that the method disclosed herein is applicable to any similar protein for the purpose of producing polymers or oligomers.

According to this aspect, the present invention provides a method of reversibly assembling a polymer or oligomer of one type of molecule or several different types of molecules. The first method step involves providing said molecules. Each molecule is comprising (a) at least one first binding moiety and (b) a second moiety that is carrying a bioactivity to be studied or utilized. In a preferred embodiment, the molecule is comprising a single binding moiety (a). In other preferred embodiments, the molecule is comprising at least two, such as two, binding moities (a). Each molecule is typically containing a number of binding moities (a) selected from the ranges 1-2, 1-4, 1-6, 2-4 and 2-6. Each binding moiety (a) consists of from 100 to 160 amino acid residues, and it is derived from the N-terminal (NT) fragment of a spider silk protein. The NT fragment has a high degree of similarity to the N-terminal amino acid sequence of spider silk proteins. As shown in Table 1 and FIG. 1, this amino acid sequence is well conserved among various species and spider silk proteins, including MaSp1 and MaSp2.

It is observed that NT has a clear dipole moment as acidic and basic residues are localized in clusters at opposite poles. Without desiring to be limited thereto, it is contemplated that the observed polymerisation of NT may involve the formation of linear arrays of NT dimers, stacked pole-to-pole with the negative surface of one subunit facing the positive surface of the neighbouring subunit in the next dimer in the array.

It is not critical which specific NT fragment(s) is present in the molecule type(s) according to this aspect of the invention, as long as the NT fragment is not entirely missing. Thus, the NT fragment(s) according to this aspect of the invention can be selected from any of the amino acid sequences shown in Table 1 or FIG. 1 or sequences with a high degree of similarity. A wide variety of N-terminal sequences can be used in the molecule type(s) according to this aspect of the invention.

The sequence of the NT fragment according to the invention has at least 50% identity, preferably at least 60% identity, to the consensus amino acid sequence SEQ ID NO: 8, which is based on the amino acid sequences of FIG. 1. In a preferred embodiment, the sequence of the NT fragment according to the invention has at least 65% identity, preferably at least 70% identity, to the consensus amino acid sequence SEQ ID NO: 8. In preferred embodiments, the NT fragment according to the invention has furthermore 70%, preferably 80%, similarity to the consensus amino acid sequence SEQ ID NO: 8.

A representative NT fragment according to the invention is the *Euprosthenops australis* sequence SEQ ID NO 6: According to a preferred embodiment of the invention, the NT fragment has at least 80% identity to SEQ ID NO: 6 or any individual amino acid sequence in FIG. 1. In preferred embodiments of the invention, the NT fragment has at least 90%, such as at least 95% identity, to SEQ ID NO: 6 or any individual amino acid sequence in FIG. 1. In preferred embodiments of the invention, the NT fragment is identical to SEQ ID NO: 6 or any individual amino acid sequence in FIG. 1.

The NT fragment contains from 100 to 160 amino acid residues. It is preferred that the NT fragment contains at least 100, or more than 110, preferably more than 120, amino acid residues. It is also preferred that the NT fragment contains at most 160, or less than 140 amino acid residues. A typical NT fragment contains approximately 130-140 amino acid residues.

All molecules of a particular method typically have the binding moiety (a) in common, but it is also possible to have different molecule types where the difference resides in use of different moieties (a) as long as they maintain their capacity to bind to each other under the pH and ion strength conditions set out herein. In general, the second moiety (b) is carrying a bioactivity to be studied or utilized, and it is typically this second moiety (b) that differs when the method involves more than one molecule type. The second moiety (b) is individually selected from proteins, nucleic acids, carbohydrates and lipids. Preferably, the second moiety (b) is also a protein.

In a preferred embodiment, the molecules of the first step are identical, i.e. of a single type, and the resulting polymer (oligomer) is thus a homopolymer (homooligomer). In another preferred embodiment, the molecules of the first step are not identical, and the resulting polymer (oligomer) is thus a heteropolymer (heterooligomer). As discussed above, the molecule heterogeneity may reside in the binding moiety (a), the bioactivity moiety (b), or both.

In the second method step, a solution of the molecules in a liquid medium is provided. The liquid medium can be any suitable medium, such as an aqueous medium, preferably a physiological medium, typically a buffered aqueous medium, such as a 10-50 mM Tris-HCl buffer or phosphate buffer. The liquid medium has a pH of 6.4 or higher and/or an ion composition that prevents polymerisation or oligomerisation of the molecules via the binding moieties. That is, the liquid medium has either a pH of 6.4 or higher or an ion composition that prevents polymerisation or oligomerisation of the molecules via the binding moieties, or both.

Ion compositions that prevent polymerisation or oligomerisation of the molecules via the binding moieties can readily be prepared by the skilled person utilizing the methods disclosed herein. A preferred ion composition that prevents polymerisation of the molecules via the binding moieties has an ionic strength of more than 300 mM. Specific examples of ion compositions that prevent polymerisation of the molecules via the binding moieties include above 300 mM NaCl, 100 mM phosphate and combinations of these ions having desired preventive effect on the polymerisation of the molecules via the binding moieties, e.g. a combination of 10 mM phosphate and 300 mM NaCl.

It has been surprisingly been found that the presence of at least one NT fragment improves the stability of the solution and prevents polymer and oligomer formation under these conditions. This can be advantageous when immediate polymerisation or oligomerisation may be undesirable, e.g. during protein purification, in preparation of large batches, or when other conditions need to be optimized. It is preferred that the pH of the liquid medium is adjusted to 6.7 or higher, such as 7.0 or higher, or even 8.0 or higher, such as up to 10.5, to achieve high solubility of the molecules. It can also be advantageous that the pH of the liquid medium is adjusted to the range of 6.4-6.8, which provides sufficient solubility of the molecules but facilitates subsequent pH adjustment to 6.3 or lower.

In the third method step, the properties of said liquid medium are adjusted so as to allow polymerisation or oligomerisation of the molecules via the binding moieties. The properties of the liquid medium are therefore adjusted to a pH of 6.3 or lower and ion composition that allows polymerisation or oligomerisation. That is, if the liquid medium wherein the molecules is dissolved has a pH of 6.4 or higher, the pH is decreased to 6.3 or lower. The skilled person is well aware of various ways of achieving this, typically involving addition of a strong or weak acid. If the liquid medium wherein the molecules are dissolved has an ion composition that prevents polymerisation or oligomerisation, the ion composition is changed so as to allow polymerisation or oligomerisation of the molecules via the binding moieties. The skilled person is well aware of various ways of achieving this, e.g. dilution, dialysis or gel filtration. If required, this step involves both decreasing the pH of the liquid medium to 6.3 or lower and changing the ion composition so as to allow polymerisation or oligomerisation. It is preferred that the pH of the liquid medium is adjusted to 6.2 or lower, such as 6.0 or lower. In particular, it may be advantageous from a practical point of view to limit the pH drop from 6.4 or 6.4-6.8 in the preceding step to 6.3 or 6.0-6.3, e.g. 6.2 in this step. In a preferred embodiment, the pH of the liquid medium of this step is 3 or higher, such as 4.2 or higher. The resulting pH range, e.g. 4.2-6.3, promotes rapid polymerisation, In the fourth method step, the molecules are allowed to assemble into a polymer or oligomer via the binding moieties in the liquid medium. The liquid medium has a pH of 6.3 or lower and an ion composition that allows polymerisation or oligomerisation of the molecules via the binding moieties. It has surprisingly been found that although the presence of the binding moiety improves solubility of the molecules at a pH of 6.4 or higher and/or an ion composition that prevents polymerisation or oligomerisation of the molecules, it accelerates polymer and oligomer formation at a pH of 6.3 or lower when the ion composition allows polymerisation or oligomerisation of the molecules. In a preferred embodiment, the pH of the liquid medium of this step is 3 or higher, such as 4.2 or higher. The resulting pH range, e.g. 4.2-6.3 promotes rapid polymerisation, In a preferred embodiment of this method, the polymer or oligomer that is obtained in the fourth step remains soluble, i.e. it is dissolved in a liquid medium having a pH of 6.3 or lower and an ion composition that allows polymerisation or oligomerisation of the molecules.

Ion compositions that allow polymerisation or oligomerisation of the molecules via the binding moieties can readily be prepared by the skilled person utilizing the methods disclosed herein. A preferred ion composition that allows polymerisation of the molecules via the binding moieties has an ionic strength of less than 300 mM. Specific examples of ion compositions that allow polymerisation of the molecules via the binding moieties include 150 mM NaCl, 10 mM phosphate, 20 mM phosphate and combinations of these ions lacking preventive effect on the polymerisation of the molecules via the binding moieties, e.g. a combination of 10 mM phosphate or 20 mM phosphate and 150 mM NaCl. It is preferred that the ionic strength of this liquid medium is adjusted to the range of 1-250 mM.

In a preferred embodiment, the method according to this aspect of the invention can comprise a fifth step of reversing the polymer or oligomer assembly. This method step involves adjusting the properties of the liquid medium to a pH of 6.4 or higher and/or an ion composition that prevents polymerisation or oligomerisation of said molecules. This causes the polymer or oligomer that is present in the liquid medium to disassemble and dissolve in the liquid medium. The liquid medium of this fifth method step can have the same composition as discussed for the liquid medium of the second method step. For instance, it is preferred that the pH of the liquid medium of the fifth method step is 6.7 or higher, such as 7.0 or higher, or even 8.0 or higher, such as up to 10.5. Alternatively, the pH of the liquid medium of the fifth method step is in the range of 6.4-6.8.

The polymer or oligomer of step (iv) can advantageously be used in interaction studies, separation, inducing activity of enzyme complexes or FRET analysis. In certain applications, at least one molecule type of the first method step is immobilised to a solid support or to the matrix of an affinity medium as set out hereinbelow.

According to one aspect, the present invention also provides method of detecting binding interactions between a subset of molecules comprised in a set of molecules. In the first method step, a set of molecules is provided. Each molecule of this set is designed as detailed above, i.e. it is comprising (a) at least one first binding moiety and (b) a second moiety that is carrying a bioactivity to be studied or utilized. In a preferred embodiment, the molecule is comprising a single binding moiety (a). In other preferred embodiments, the molecule is comprising at least two, such as two, binding moities (a). Each molecule is typically containing a number of binding moieties (a) selected from the ranges 1-2, 1-4, 1-6, 2-4 and 2-6. Each binding moiety (a) consists of from 100 to 160 amino acid residues, and it is derived from the N-terminal (NT) fragment of a spider silk protein as set out above. Each bioactivity moiety (b) is individually selected from proteins, nucleic acids, carbohydrates and lipids, preferably proteins.

In the second method step, a solution of said set of molecules in a liquid medium is provided. As set out above, the liquid medium has at pH 6.4 or higher and/or an ion composition that prevents polymerisation or oligomerisation of said molecules. Preferred compositions of the liquid medium are evident from the previous disclosure.

In the third method step, the properties of the liquid medium are adjusted to allow polymerisation or oligomerisation of the molecules. As set out above, the liquid medium has a pH of 6.3 or lower and an ion composition that allows polymerisation or oligomerisation of the molecules. Preferred compositions of the liquid medium are evident from the previous disclosure.

In the fourth method step, the molecules of this set are allowed to assemble into a polymer or oligomer via said binding moieties in the liquid medium. As set out above, the liquid medium has a pH of 6.3 or lower and an ion composition that allows polymerisation or oligomerisation of the molecules. Preferred compositions of the liquid medium are evident from the previous disclosure.

In the fifth method step, the properties of the liquid medium are adjusted so as to disassemble the polymer or oligomer. As set out above, the liquid medium has at pH 6.4 or higher and/or an ion composition that prevents polymerisation or oligomerisation of said molecules. Preferred compositions of the liquid medium are evident from the previous disclosure. This causes disassembly of the polymer or oligomer by preventing association via the NT-derived binding moieties.

In the final and sixth method step, the presence of binding interactions which are not mediated via said binding moieties between two or more different molecules are determined. This identifies binding interactions between a subset of molecules that do not involve the pH/salt-regulated polymerisation or oligomerisation that is mediated via the NT-derived binding moieties.

A related aspect of the invention is based on the insight that the NT fragment will form large soluble assemblies when the pH is lowered from ca 7 to 6, or more specifically from above 6.4 to below 6.3. This assembly occurs most efficiently at a pH above 4.2, i.e. in the range of 4.2-6.3, such as 4.2-6. This property can be used for affinity purification, e.g. if NT is immobilized on a column. This approach allows release of bound proteins by a shift in pH within a physiologically relevant interval, since the assembly will resolve when pH is elevated from ca 6 to 7.

In a preferred embodiment of the methods according to the invention, the step of isolating the spider silk protein involves purification of the spider silk protein on an affinity medium, such as an affinity column, with an immobilized NT moiety. Purification of the spider silk protein on an affinity medium is preferably carried out with association to an affinity medium with an immobilized NT moiety at a pH of 6.3 or lower, preferably in the range of 4.2-6.3, followed by dissociation from the affinity medium with a desired dissociation medium at a pH of 6.4 or higher and/or having a high ionic strength. A dissociation medium having high ionic strength typically has an ionic strength of more than 300 mM, such as above 300 mM NaCl.

These affinity-based procedures utilize the inherent properties of the NT moiety according to the invention. Of particular interest is the strong tendency of spidroin NT protein fragments to associate at a pH below 6.3, in particular in the range of 4.2-6.3. This can advantageously be utilized as a powerful affinity purification tool, allowing one-step purification of spider silk proteins according to the invention from complex mixtures. Although chromatography is preferred, other affinity-based purification methods than chromatography can obviously be employed, such as magnetic beads with functionalized surfaces or filters with functionalized surfaces.

Thus, methods of producing a spider silk protein according to the invention may involve purification of the spider silk protein on an affinity medium with an immobilized NT moiety. Preferably, the purification of the fusion protein on an affinity medium is carried out with association to an affinity medium with an immobilized NT moiety at a pH of 6.3 or lower, followed by dissociation from the affinity medium with a desired dissociation medium at a pH of 6.4 or higher and/or having a high ionic strength. The purification occurs typically in a column, on magnetic beads with functionalized surfaces, or on filters with functionalized surfaces.

The present invention also provides an affinity medium comprising a matrix and a ligand for affinity interactions coupled to said matrix, optionally via a spacer arm. The ligand is comprising at least one fragment of from 100 to 160 amino acid residues which is derived from the N-terminal fragment of a spider silk protein as set out in this description of the invention. In a preferred embodiment, the ligand is comprising a single fragment. In other preferred embodiments, the ligand is comprising at least two, such as fragments. Each ligand is typically containing a number of fragments selected from the ranges 1-2, 1-4, 1-6, 2-4 and 2-6. The matrix is typically selected from the group consisting of particles, e.g. polysaccharide particles, and filters. Examples of particles include polysaccharide beads, e.g. agarose, Sepharose and Superose, and magnetic beads.

According to a related aspect, the present invention provides a novel use of one or more molecules. As set out above, each molecule is comprising (a) at least one first binding moiety of from 100 to 160 amino acid residues which is derived from the N-terminal fragment of a spider silk protein, and (b) a second moiety which is individually selected from proteins, nucleic acids, carbohydrates and lipids. In a preferred embodiment, the molecule is comprising a single binding moiety (a). In other preferred embodiments, the molecule is comprising at least two, such as two, binding moities (a). Each molecule is typically containing a number of binding moities (a) selected from the ranges 1-2, 1-4, 1-6, 2-4 and 2-6. The molecules are used for reversibly assembling a polymer or oligomer of the molecules via the binding moieties in a solution at a pH of 6.3 or lower and an ion composition that allows polymerisation or oligomerisation of said molecules. In a preferred embodiment, the pH of the solution is 3 or higher, such as 4.2 or higher. The resulting pH range, e.g. 4.2-6.3 promotes rapid polymerisation, Preferably, the resulting polymer or oligomer is used in interaction studies, separation, inducing activity of enzyme complexes or FRET analysis.

The results and conclusions disclosed herein provide new insights in spider silk assembly at the molecular level. Without desiring to be limited to any particular theory, the polar and unbalanced charge distribution of NT is ideally suited for generation of a polymerisable module that can be simply controlled by pH and salt concentration. This in turn allows NT to regulate silk assembly by preventing premature aggregation and triggering polymerisation as the pH is lowered, similar to what is perceived to occur along the spider's silk extrusion duct.

The present invention will in the following be further illustrated by the following non-limiting examples.

Materials and Methods
Protein Expression and Purification

Expression vectors were constructed to produce NT (SEQ ID NO: 6), NTΔHis6, NT5Rep (SEQ ID NO: 4), NT4Rep (SEQ ID NO: 3), and 4RepCT (SEQ ID NO: 2), respectively, as C-terminal fusions to His$_6$TrxHis$_6$, and NT4RepCT (SEQ ID NO: 5) as an N-terminal fusion to His$_6$. The different vectors were used to transform *Escherichia coli* BL21(DE3) cells (Merck Biosciences) that were grown at 30° C. in Luria-Bertani medium containing kanamycin to an OD600 of ~1, induced with isopropyl-β-D-thiogalactopyranoside, and further incubated for up to 4 hours at room temperature. Lysis, immobilised metal affinity purification and proteolytic removal of the His$_6$TrxHis$_6$-tag was performed as described in Hedhammar, M. et al. Biochemistry 47, 3407-3417, (2008).

Dynamic Light Scattering (DLS)

The effect of pH and ionic strength on the hydrodynamic diameter of NT and NTΔHis6 (to exclude that pH dependent effects are caused by His at position 6) was measured at 25±0.1° C. in a Zetasizer Nano S from Malvern Instruments (Worcestershire, UK) equipped with a 633 nm HeNe laser. The buffers were filtered through nylon filters prior to use. The sample volume was 50 µl and ZEN2112 low glass cuvettes were used. The attenuation and measurement positions from the cuvette wall (4.65 mm) were kept constant for all analyses. Six scans were performed for each sample. All samples were analyzed in triplicate. The hydrodynamic diameter (dH) was calculated using the General Purpose algorithm in the Malvern software for DLS analysis, which correlates the diffusion coefficient to the hydrodynamic diameter through the Stokes-Einstein equation:

$$d_H = \frac{k_B T}{3\pi \eta D}$$

where $k_B$ is the Boltzmann constant, T is the temperature, η is the viscosity and D is the translational diffusion coefficient. The viscosity and refractive index values of the solvent were obtained from the Malvern software. The Multiple Narrow Modes algorithm was used to verify the results obtained by the General Purpose method. NT and NTΔHis6 samples were analyzed at a concentration of 0.8 mg/ml.

Turbidimetry

Turbidity was estimated from the apparent absorbance at 340 nm of proteins (0.8 mg/ml) at different pH values at 25° C. in an SLM 4800S spectrofluorimeter equipped with OLIS electronics and software (OLIS Inc. Bogart, Ga.). NT, NT4Rep, and NTΔHis6 were analysed, with essentially the same results.

Fiber Formation and Scanning Electron Microscopy (SEM)

Conditions for fiber formation were essentially as described in Stark, M. et al. Biomacromolecules 8, 1695-1701, (2007). Approximately 25 µM of each protein was incubated in 20 mM Na phosphate buffer at pH 7 or 6, with or without 300 mM NaCl. At different time points, samples were applied on SEM stubs, where they were air-dried and vacuum-coated with gold and palladium. The samples were photographed with a LEO 1550 FEG microscope (Carl Zeiss, Oberkochen, Germany) using an acceleration voltage of 5 kV.

EXAMPLES

Example 1

Expression and Purification of NT and Minispidroins

Expression vectors (SEQ ID NO: 14-16 and others) were constructed to produce NT (SEQ ID NO: 6), NTΔHis6, NT5Rep (SEQ ID NO: 4), NT4Rep (SEQ ID NO: 3), and 4RepCT (SEQ ID NO: 2), respectively, as C-terminal fusions to His$_6$TrxHis$_6$, and NT4RepCT (SEQ ID NO: 5) as an N-terminal fusion to His$_6$. The different vectors were used to transform *Escherichia coli* BL21(DE3) cells (Merck Biosciences) that were grown at 30° C. in Luria-Bertani medium containing kanamycin to an OD600 of ~1, induced with isopropyl-β-D-thiogalactopyranoside, and further incubated for up to 4 hours at room temperature. Thereafter, cells were harvested and resuspended in 20 mM Tris-HCl (pH 8.0) supplemented with lysozyme and DNase I. After complete lysis, the 15000 g supernatants were loaded onto a column packed with Ni-NTA Sepharose (GE Healthcare, Uppsala, Sweden). The column was washed extensively before bound proteins were eluted with 300 mM imidazole. Fractions containing the target proteins were pooled and dialyzed against 20 mM Tris-HCl (pH 8.0). MaSp1 proteins were released from the tags by proteolytic cleavage using a thrombin:fusion protein ratio of 1:1000 (w/w) at room temperature for 1-2 h. To remove the released HisTrxHis tag, the cleavage mixture was loaded onto a second Ni-NTA Sepharose column and the flowthrough was collected. Protein samples were separated via SDS-PAGE and then stained with Coomassie Brilliant Blue R-250. The proteins were concentrated by ultrafiltration using a 5 kDa molecular mass cutoff cellulose filter (Millipore).

Example 2 pH-Dependent Polymerisation of NT and Minispidroins

Polymerisation of mini-spidroins with (NT4RepCT or NT4Rep) or without NT (4RepCT or 4Rep) was performed at pH 7 (FIG. 3, above time scale) or at pH 6 (FIG. 3, below time scale).

Miniature spidroins consisting of repeat regions, with or without the C-terminal fragment show no sensitivity towards environmental changes, such as pH fluctuations (4Rep and 4RepCT; FIG. 3). To test the hypothesis that it is the N-terminal fragment that is responsible for pH-dependent spidroin polymerisation, several constructs encompassing the N-terminal fragment of major ampullate spidroin (MaSp) 1 from *Euprosthenops australis* (NT, NT4Rep and NT4RepCT; FIG. 3) were used to obtain purified recombinant proteins (Example 1). Dynamic light scattering, turbidimetry, and scanning electron microscopy were used to probe the effect of pH and salt concentration on solubility and polymerisation of NT alone, as well as of the minispidroin constructs.

Figure 4:
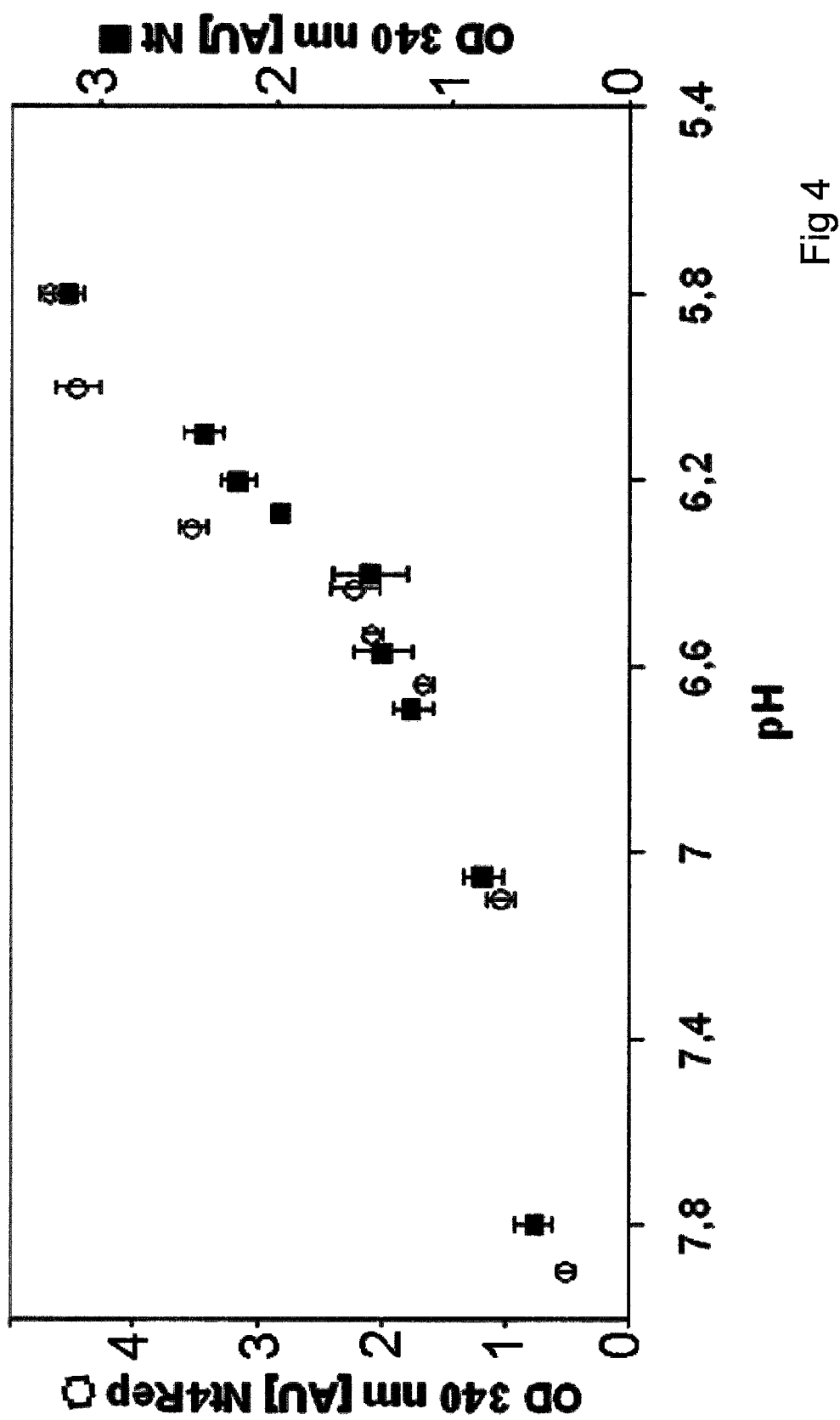
FIG. 4 shows turbidimetry of NT and NT4Rep at different pHs.

NT and NT4Rep were subjected to turbidimetry at different pH values. Mean values (±SD, n=3) of NT4Rep (circles) and NT (squares) are shown in FIG. 4. Similar results were obtained for NT5Rep.

Figure 5:
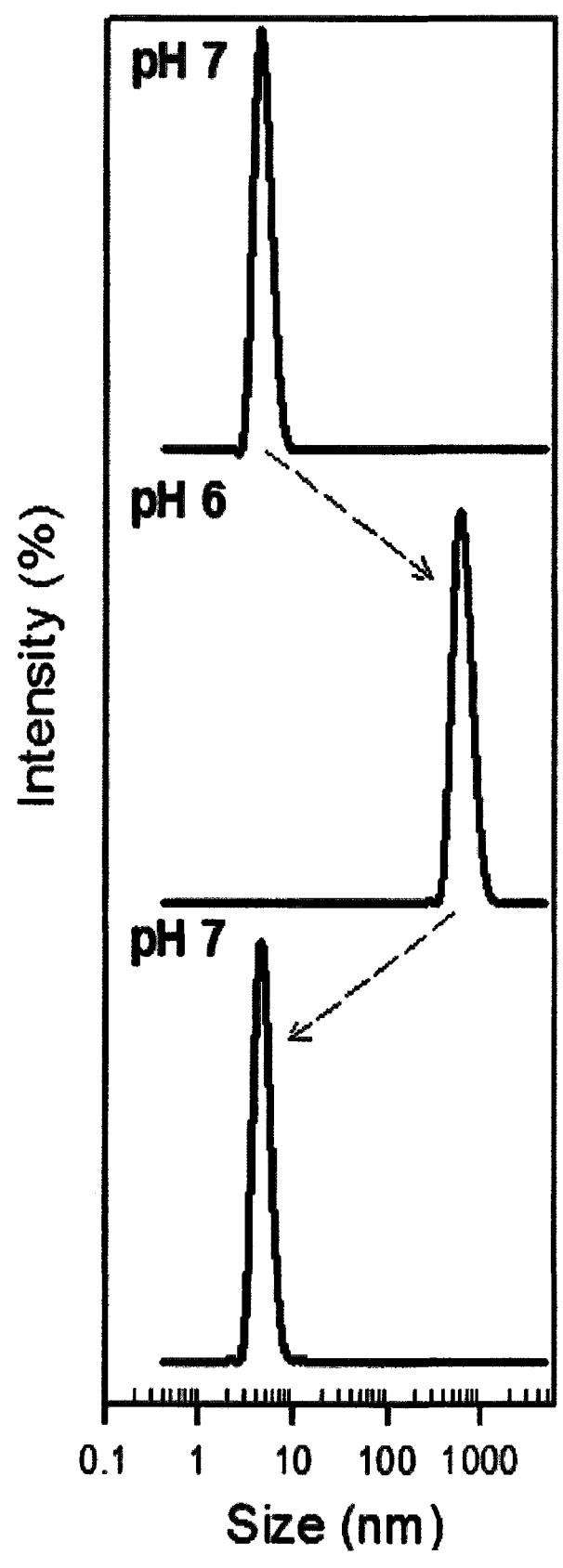
FIG. 5 shows dynamic light scattering of NT at pH 6 and 7.

NT was subjected to dynamic light scattering at pH 6-7 and 0-300 mM NaCl. Representative examples of three experiments is shown in FIG. 5. See also Table 3

TABLE 3

Size of the protein assemblies determined by dynamic light scattering

| Sample | Size (nm) | % assemblies |
| --- | --- | --- |
| 100 mM phosphate buffer, pH 7.2 | 4.2 ± 0.1 | 99.9% |
| 100 mM phosphate buffer, pH 6.2 | 4.2 ± 0.1 | 99.9% |
| 10 mM phosphate buffer + 150 mM NaCl, pH 7.2 | 4.1 ± 0.1 | 99.9% |
| 10 mM phosphate buffer + 150 mM NaCl, pH 6.1 | 710 ± 142 | 96.8% |
| 10 mM phosphate buffer, pH 7.2 | 4.5 ± 0.1 | 99.8% |
| 10 mM phosphate buffer, pH 6.0 | 687 ± 50 | 100% |
| 10 mM phosphate buffer + 300 mM NaCl, pH 7.2 | 4.3 ± 0.3 | 99.9% |
| 10 mM phosphate buffer + 300 mM NaCl, pH 6.2 | 4.4 ± 0.3 | 99.9% |

Figure 6:
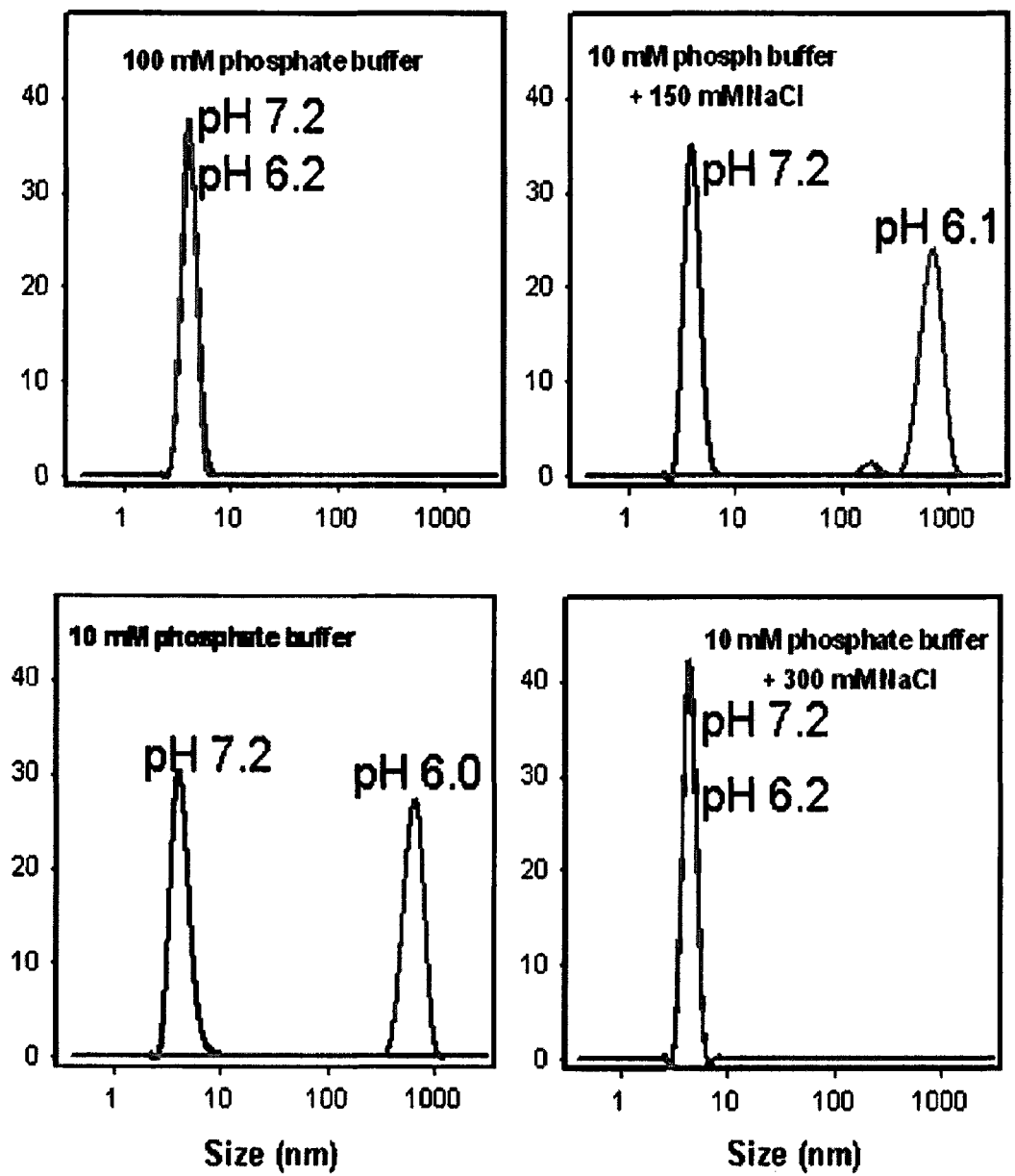
FIG. 6 shows dynamic light scattering of NT at pH 6.1-7.2 in various ion compositions.

Alone, NT forms a remarkably soluble (>210 mg/ml) dimer at pH 7.0, but instantly forms polymers with a hydrodynamic size of ~700 nm below pH 6.4 (FIGS. 4 and 5). NT polymerisation is easily reversed by an increase of pH and blocked by high levels of salt (FIGS. 5 and 6). These properties are maintained in NTΔHis6 (turbidimetry) and are propagated into minispidroins that include the NT fragment (NT4RepCT, NT4Rep, NTTNT4RepCT and NT5Rep), which thereby gain solubility at pH 7 but quickly polymerise at pH 6 (FIG. 3).

The arrows in FIG. 3 indicate when macroscopic formations first were detected, showing that at pH 7 the presence of NT delays polymerisation, while at pH 6 it accelerates polymerisation. This is independent of whether the C-terminal fragment (filled circle) is present or not (indicated by the striped circle). Moreover, the presence of NT results in more ordered polymerisation, exemplified by the scanning electron micrographs in FIG. 3, which are representative early polymers for all constructs at pH 7 (above time scale) or for NT4RepCT at pH 6 (below time scale). The observed effects of pH and salt suggest that spidroin polymerisation depends on electrostatic interactions involving NT.

Example 3

NT as a Mediator of pH-Dependent and Reversible Interactions

Figure 7:
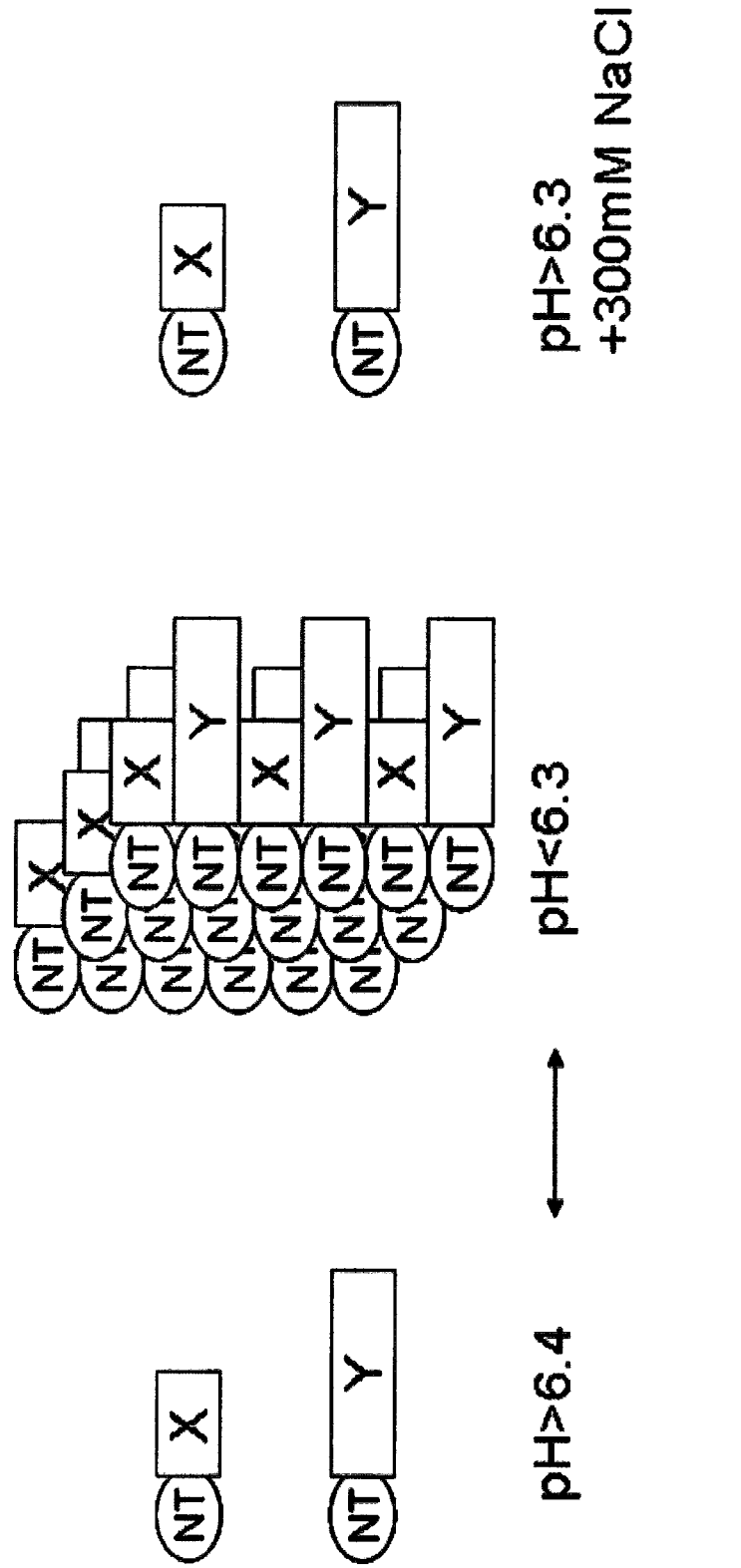
FIG. 7 schematically shows pH dependent assembly of NT-fusion proteins.

The N-terminal fragment (NT) of major ampullate spidroin 1 from the dragline of *Euprosthenops australis* is highly soluble (>210 mg/ml) at pH 7 but polymerises via charge interactions into ~700 nm polymers at pH values below 6.4 (shown by dynamic light scattering and turbidimetry). The NT polymerisation is easily reversed by an increase of pH and blocked by high levels of salt. These polymerisation properties are propagated into fusion proteins that include the NT fragment (e.g. NT-X and NT-Y), which thereby gain solubility at pH 7 but quickly polymerise at pH 6 (FIG. 7). This reversible way of assembling two different proteins can be used in studies of interactions between proteins, nucleic acids, carbohydrates or lipids, for example analyses of protein-protein interactions employing fluorescence resonance energy transfer, or in induction of activities, for example enzyme activities, or for localization or immobilization of proteins, nucleic acids, carbohydrates or lipids, or in analysis or separation of proteins, nucleic acids, carbohydrates or lipids, for example using array techniques.

Example 4

Production of an MetSP-C33Leu Fusion Protein

An expression vector was constructed comprising a gene encoding NT-MetSP-C33Leu as a fusion to $His_6$ (SEQ ID NOS: 26-27). The vector was used to transform *Escherichia coli* BL21(DE3) cells (Merck Biosciences) that were grown at 30° C. in Luria-Bertani medium containing kanamycin to an $OD_{600}$ of 0.9-1, induced with isopropyl-β-D-thiogalactopyranoside (IPTG), and further incubated for 3 hours at 25° C. The cells were harvested by centrifugation and resuspended in 20 mM Tris-HCl, pH 8.

Lysozyme was added, and the cells were incubated for 30 min on ice. Tween was added to a final concentration of 0.7%. The cells were disrupted by sonication on ice for 5 min, alternating 2 seconds on and 2 seconds off. The cell lysate was centrifuged at 20 000×g for 30 min. The supernatant was loaded on a Ni-NTA sepharose column, equilibrated with 20 mM Tris-HCl, pH 8 buffer containing 0.7% Tween. The column was washed with 20 mM Tris-HCl, pH 8 buffer containing 0.7% Tween, and the bound protein was eluted with 20 mM Tris-HCl pH 8, 300 mM imidazole buffer containing 0.7% Tween.

Figure 8:
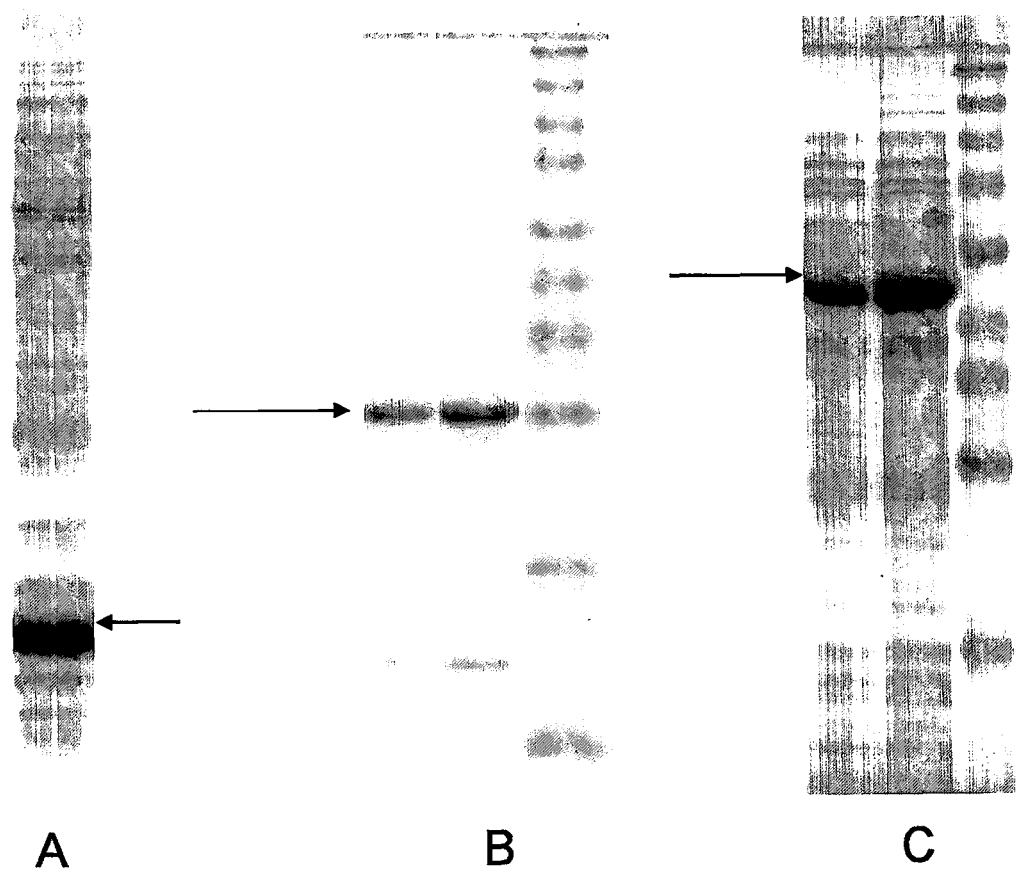
FIG. 8 shows electrophoresis gels of fusion proteins.

The eluate was subjected to SDS-PAGE on a 12% Tris-Glycine gel under reducing conditions. A major band corresponding to the fusion protein is indicated by the arrow in FIG. 8A. The yield was determined by mg purified protein from 1 litre shake flask culture grown to an $OD_{600}$ of 1. The yield was 64 mg/l. It is concluded that a fusion protein containing a single NT moiety results in surprisingly high yield in the presence of detergent in the cell lysate.

Example 5

Production of an MetSP-C33Leu Fusion Protein

An expression vector was constructed comprising a gene encoding $NT_2$-MetSP-C33Leu (i.e. NTNT-MetSP-C33Leu) as a fusion to $His_6$ (SEQ ID NOS: 28-29). The vector was used to transform *Escherichia coli* BL21(DE3) cells (Merck Biosciences) that were grown at 30° C. in Luria-Bertani medium containing kanamycin to an OD$_{600}$ of 0.9-1, induced with isopropyl-β-D-thiogalactopyranoside (IPTG), and further incubated for 3 hours at 25° C. The cells were harvested by centrifugation and resuspended in 20 mM Tris-HCl, pH 8.

Lysozyme was added, and the cells were incubated for 30 min on ice. Tween was either not added or added to a final concentration of 0.7%. The cells were disrupted by sonication on ice for 5 min, alternating 2 seconds on and 2 seconds off. The cell lysate was centrifuged at 20 000×g for 30 min. The supernatants were loaded on a Ni-NTA sepharose column, equilibrated with 20 mM Tris-HCl, pH 8 buffer±0.7% Tween. The column was washed with 20 mM Tris-HCl, pH 8 buffer±0.7% Tween, and the bound protein was eluted with 20 mM Tris-HCl pH 8, 300 mM imidazole buffer±0.7% Tween.

The eluate was subjected to SDS-PAGE on a 12% Tris-Glycine gel under reducing conditions. A major band corresponding to the fusion protein in the two lanes to the left is indicated by the arrow in FIG. 8B. The yield was determined by mg purified protein from 1 litre shake flask culture grown to an OD$_{600}$ of 1. The yield was 40 mg/l in the absence of Tween, and 68 mg/l in the presence of 0.7% Tween. It is concluded that a fusion protein containing two consecutive NT moieties results in surprisingly high yield in the absence of detergent in the cell lysate, and an even further increased yield in the presence of detergent in the cell lysate.

Example 6

Preparation of NT-Sepharose

A CysHis$_6$NT construct was used to transform *Escherichia coli BL*21(DE3) cells (Merck Biosciences). The cells were grown at 30° C. in Luria-Bertani medium containing kanamycin to an OD600 of 0.8-1, induced with isopropyl-β-D-thiogalactopyranoside (IPTG), and further incubated for up to 4 hours at room temperature. Thereafter, cells were harvested and resuspended in 20 mM Tris-HCl, pH 8.0, supplemented with lysozyme and DNase I. After complete lysis, the 15000 g supernatants were loaded on a column packed with Ni sepharose (GE Healthcare). The column was washed extensively, and then bound proteins were eluted with 100-300 mM imidazole. Fractions containing the target proteins were pooled and dialyzed against 20 mM Tris-HCl, pH 8.0. Purified Cys-His6-NT protein is coupled to activated thiol Sepharose using standard protocol (GE Healthcare).

Example 7

Purification of Fusion Proteins Using NT Sepharose

Cell lysates from Examples 4 and 5 are loaded on a column packed with NT Sepharose, pre-equilibrated with 20 mM sodium phosphate, pH 6. The column is washed extensively with 20 mM sodium phosphate, pH 6 and then bound proteins are eluted with 20 mM sodium phosphate, pH 7. Fractions containing the target proteins are pooled. Protein samples are separated on SDS-PAGE gels and then stained with Coomassie Brilliant Blue R-250. Protein content is determined from absorbance at 280 nm.

Example 8

Production of NT-REP$_4$-CT

An expression vector was constructed to produce NT-REP$_4$-CT as an N-terminal fusion to His$_6$ (SEQ ID NOS 17-18). The vector was used to transform *Escherichia coli* BL21(DE3) cells (Merck Biosciences) that were grown at 30° C. in Luria-Bertani medium containing kanamycin to an OD$_{600}$ of ~1, induced with isopropyl-β-D-thiogalactopyranoside (IPTG), and further incubated for up to 4 hours at room temperature. Thereafter, cells were harvested and resuspended in 20 mM Tris-HCl (pH 8.0) supplemented with lysozyme and DNase I.

After complete lysis, the 15000 g supernatants were loaded onto a column packed with Sepharose (GE Healthcare, Uppsala, Sweden). The column was washed extensively before bound proteins were eluted with 300 mM imidazole. Fractions containing the target proteins were pooled and dialyzed against 20 mM Tris-HCl (pH 8.0).

Protein samples were separated via SDS-PAGE and then stained with Coomassie Brilliant Blue R-250. The resulting NT-REP$_4$-CT protein was concentrated by ultrafiltration using a 5 kDa molecular mass cutoff cellulose filter (Millipore).

Example 9

Production of NT-REP$_4$-CT

An expression vector was constructed to produce NT-REP$_4$-CT as a C-terminal fusion to Zbasic (SEQ ID NO 19). The vector was used to transform *Escherichia coli* BL21 (DE3) cells (Merck Biosciences) that were grown at 30° C. in Luria-Bertani medium containing kanamycin to an OD$_{600}$ of ~1, induced with isopropyl-β-D-thiogalactopyranoside (IPTG), and further incubated for up to 2-4 hours at room temperature. Thereafter, cells were harvested and resuspended in 50 mM Na phosphate (pH 7.5) supplemented with lysozyme and DNase I.

After complete lysis, the 15000 g supernatants were loaded onto cation exchanger (HiTrap S, GE Healthcare, Uppsala, Sweden). The column was washed extensively before bound proteins were eluted with a gradient against 500 mM NaCl. Fractions containing the target proteins were pooled and dialyzed against 50 mM Na phosphate (pH 7.5). The NT-REP$_4$-CT protein (SEQ ID NO 20) was released from the Zbasic tags by proteolytic cleavage using a protease 3C:fusion protein ratio of 1:50 (w/w) at 4° C. over night. To remove the released Zbasic tag, the cleavage mixture was loaded onto a second cation exchanger, and the flowthrough was collected.

Example 10

Production of NT-REP$_4$-CT

An expression vector was constructed to produce NT-REP$_4$-CT as an C-terminal fusion to HisTrxHis (SEQ ID NO 21). The vector was used to transform *Escherichia coli* BL21(DE3) cells (Merck Biosciences) that were grown at 30° C. in Luria-Bertani medium containing kanamycin to an OD$_{600}$ of ~1, induced with isopropyl-β-D-thiogalactopyranoside (IPTG), and further incubated for up to 2-4 hours at room temperature. Thereafter, cells were harvested and resuspended in 20 mM Tris-HCl (pH 8.0) supplemented with lysozyme and DNase I.

After complete lysis, the 15000 g supernatants were loaded onto column packed with Ni-Sepharose (GE Healthcare, Uppsala, Sweden). The column was washed extensively before bound proteins were eluted with a gradient against 500 mM NaCl. Fractions containing the target proteins were pooled and dialyzed against 20 mM Tris-HCl (pH 8.0). The NT-REP$_4$-CT protein (SEQ ID NO 22) was released from the HisTrxHis tags by proteolytic cleavage using a thrombin: fusion protein ratio of 1:1000 (w/w) at 4° C. over night. To remove the released HisTrxHis, the cleavage mixture was loaded onto a second Ni-Sepharose column, and the flowthrough was collected.

Example 11

Production of NT$_2$-REP$_4$-CT

An expression vector was constructed comprising a gene encoding NT$_2$-REP-CT (i.e. NTNT-REP-CT) as a fusion to His$_6$ (SEQ ID NOS: 23-24). The vector was used to transform *Escherichia coli* BL21(DE3) cells (Merck Biosciences) that were grown at 30° C. in Luria-Bertani medium containing kanamycin to an OD$_{600}$ of 0.9-1, induced with isopropyl-β-D-thiogalactopyranoside (IPTG), and further incubated for 3 hours at 25° C. The cells were harvested by centrifugation and resuspended in 20 mM Tris-HCl, pH 8.

Lysozyme and DNase were added, and the cells were incubated for 30 min on ice. The cell lysate was centrifuged at 20 000×g for 30 min. The supernatants were loaded on a Ni-NTA sepharose column, equilibrated with 20 mM Tris-HCl, pH 8 buffer. The column was washed with 20 mM Tris-HCl, pH 8 buffer, and the bound protein was eluted with 20 mM Tris-HCl pH 8, 300 mM imidazole buffer.

The eluate was subjected to SDS-PAGE on a 12% Tris-Glycine gel under reducing conditions. A major band corresponding to the fusion protein in the two lanes to the left is indicated by the arrow in FIG. 8C. The yield was determined by mg purified protein from 1 litre shake flask culture grown to an OD$_{600}$ of 1. The yield was 30 mg/l. It is concluded that spidroin miniature proteins can advantageously be expressed as fusions with two NT moieties.

Example 12

Production of NT-REP$_4$-CT, NT$_2$-REP$_4$-CT and NT-REP$_8$-CT

Expression vectors are constructed comprising a gene encoding NT-REP$_4$-CT (SEQ ID NOS 20 and 22), NT$_2$-REP$_4$-CT (SEQ ID NO 23), and NT-REP$_8$-CT (SEQ ID NO: 25), respectively. The vectors are used to transform *Escherichia coli* BL21(DE3) cells (Merck Biosciences) that are grown at 30° C. in Luria-Bertani medium containing kanamycin to an OD$_{600}$ of 0.9-1, induced with isopropyl-β-D-thiogalactopyranoside (IPTG), and further incubated for 3 hours at 25° C. The cells are harvested by centrifugation and resuspended in 20 mM Tris-HCl, pH 8.

Lysozyme is added, and the cells are incubated for 30 min on ice. Tween is either not added or added to a final concentration of 0.7%. The cell lysates are centrifuged at 20 000×g for 30 min. An NT affinity medium is prepared as described in Example 6. The supernatant is loaded on an NT affinity column in accordance with Example 7. Eluate from the NT affinity column is subjected to gel electrophoresis.

Example 13

Production of NTHisNT$_2$-REP$_8$-CT and NT$_2$-Brichos

A) NTHis

An expression vector was constructed to produce NT as an N-terminal fusion to His$_6$ (SEQ ID NO 30). The vector was used to transform *Escherichia coli* BL21(DE3) cells (Merck Biosciences) that were grown at 30° C. in Luria-Bertani medium containing kanamycin to an OD$_{600}$ of ~1, induced with isopropyl-β-D-thiogalactopyranoside (IPTG), and further incubated for up to 4 hours at room temperature. Thereafter, cells were harvested and resuspended in 20 mM Tris-HCl (pH 8.0) supplemented with lysozyme and DNase I.

After complete lysis, the 15000 g supernatants were loaded onto a column packed with Ni-Sepharose (GE Healthcare, Uppsala, Sweden). The column was washed extensively before bound proteins were eluted with 300 mM imidazole. Fractions containing the target proteins were pooled and dialyzed against 20 mM Tris-HCl (pH 8.0). Protein samples were separated via SDS-PAGE and then stained with Coomassie Brilliant Blue R-250. The resulting NT protein (SEQ ID NO 30) was concentrated by ultrafiltration using a 5 kDa molecular mass cutoff cellulose filter (Millipore). The yield was 112 mg/litre shake flask grown to an OD$_{600}$ of 1.

B) N$_2$-REP$_8$-CT

An expression vector was constructed to produce NT$_2$-REP$_8$-CT (NTNT8REPCT) as an N-terminal fusion to His$_6$ (SEQ ID NO 31). The vector were used to transform *Escherichia coli* BL21(DE3) cells (Merck Biosciences) that were grown at 30° C. in Luria-Bertani medium containing kanamycin to an OD$_{600}$ of ~1, induced with isopropyl-β-D-thiogalactopyranoside (IPTG), and further incubated for up to 4 hours at room temperature. Thereafter, cells were harvested and resuspended in 20 mM Tris-HCl (pH 8.0) supplemented with lysozyme and DNase I. Protein samples were separated via SDS-PAGE and then stained with Coomassie Brilliant Blue R-250 to confirm protein expression.

After complete lysis, the 15000 g supernatants are loaded onto a column packed with Ni-Sepharose (GE Healthcare, Uppsala, Sweden). The column is washed extensively before bound proteins are eluted with 300 mM imidazole. Fractions containing the target proteins are pooled and dialyzed against 20 mM Tris-HCl (pH 8.0). Protein samples are separated via SDS-PAGE and then stained with Coomassie Brilliant Blue R-250.

C) NT$_2$-Brichos

An expression vector was constructed to produce NT$_2$-Brichos (NT-NT-Brichos) as an N-terminal fusion to His$_6$ (SEQ ID NO 32). The vector was used to transform *Escherichia coli* BL21(DE3) cells (Merck Biosciences) that were grown at 30° C. in Luria-Bertani medium containing kanamycin to an OD$_{600}$ of ~1, induced with isopropyl-β-D-thiogalactopyranoside (IPTG), and further incubated for up to 4 hours at room temperature. Thereafter, cells were harvested and resuspended in 20 mM Tris-HCl (pH 8.0) supplemented with lysozyme and DNase I. The cells were further disrupted by sonication on ice for 5 minutes, 2 seconds on and 2 seconds off.

After complete lysis, the 15000 g supernatants were loaded onto a column packed with Ni-Sepharose (GE Healthcare, Uppsala, Sweden). The column was washed extensively before bound proteins were eluted with 300 mM imidazole. Fractions containing the target proteins were pooled and dialyzed against 20 mM Tris-HCl (pH 8.0). Protein samples were separated via SDS-PAGE and then stained with Coomassie Brilliant Blue R-250. The resulting NT$_2$-Brichos protein (SEQ ID NO 32) was concentrated by ultrafiltration using a 5 kDa molecular mass cutoff cellulose filter (Millipore). The yield was 20 mg/litre shake flask grown to an OD600 of 1.

Example 14

NT for pH-Dependent, Reversible Capture

Purpose: Use covalently immobilised NT (and NTNT) to reversibly capture NT fusion proteins.

Strategy: Investigate pH dependent assembly of NT (and NTNT) fusion proteins to fibers (and film) with covalently linked NT (and NTNT). Fibers and films without NT are used as control.

A) Fibers

Fibers (~0.5 cm long, ~50 ug) of NT-REP$_4$-CT (SEQ ID NO 20), NT$_2$-REP$_4$-CT (SEQ ID NO 23) and REP$_4$-CT (SEQ ID NO 2, control) were submerged in 100 µl solution of 5 mg/ml soluble NTHis (SEQ ID NO 30) or NT$_2$-Brichos (SEQ ID NO 32) at pH 8 for 10 minutes. The pH was decreased by addition of 400 ul sodium phosphate buffer (NaP) to pH 6 and incubated for 10 minutes to allow assembly of soluble NT to the fiber. The fibers were transferred to 500 µl of NaP at pH 6, and washed twice. Finally, the fibers were transferred to 500 µl of NaP at pH 7, and incubated 10 minutes to allow release of soluble NT. The same was done in the presence of 300 mM NaCl in all pH 6 NaP buffers. Samples from the different solutions were analysed on SDS-PAGE.

Using the $NT_2$-$REP_4$-CT and NT-$REP_4$-CT fibers, both NTHis and $NT_2$-Brichos were captured at pH 6. Upon pH raise to pH 7, both NTHis and $NT_2$-Brichos) were released again and could be detected on SDS-PAGE. The addition of 300 mM NaCl decreased capture at pH 6.

B) Film:

Films of NT-$REP_4$-CT (SEQ ID NO 20) and $REP_4$-CT (SEQ ID NO 2, control) were prepared by casting 50 µl of a protein solution of 3 mg/ml in a plastic well and left to dry over night. The next day, 100 µl solution of 5 mg/ml soluble NTHis (SEQ ID NO 30) at pH 8 was added to wells with film, and left for 10 minutes. The pH was then decreased to 6 by addition of 400 µl NaP and incubated for 10 minutes to allow assembly of soluble NT to the film. The films were then washed twice with 500 µl of NaP at pH 6. For release of soluble NTHis, 500 µl of NaP at pH 7 was added and incubated for 10 minutes. The same was done in presence of 300 mM NaCl in all pH 6 NaP buffers. Samples from the different solutions were analysed on SDS-PAGE.

Analysis on SDS-PAGE showed that a NT-$REP_4$-CT film allowed NTHis to be captured at pH 6 and released again upon raise of the pH to 7.

Example 15

NT for pH-Dependent, Reversible Assembly of Fusion Proteins

Purpose: Use NT as a reversible tag that allows analysis of interaction between protein moieties, e.g. analyse the interaction of Brichos with targets with beta sheet structures e.g. surfactant protein C(SP-C).

$NT_2$-Brichos (SEQ ID NO 32) is mixed with either $NT_2$-MetSP-C33Leu (SEQ ID NO 28) or NTHis (SEQ ID NO 30) to a total volume of 100 μl at pH 8. NaP buffer (400 ul) is added to give a final pH of 6, and the mixture is incubated for 20 minutes to allow NT assembly. The pH is then raised again to pH 7 to allow reversal of NT assembly. Samples from the different solutions are analysed on native gel and size exclusion chromatography (SEC).

The invention claimed is:

1. A method of producing polymers of an isolated spider silk protein, comprising the steps of:
   (i) providing a spider silk protein consisting of from 170 to 760 amino acid residues and comprising:
      an N-terminal (NT) fragment consisting of at least one fragment of from 100 to 160 amino acid residues derived from the N-terminal fragment of a spider silk protein; and
      a repetitive fragment of from 70 to 300 amino acid residues derived from the repetitive fragment of a spider silk protein; and optionally
      a C-terminal (CT) fragment of from 70 to 120 amino acid residues, which fragment is derived from the C-terminal fragment of a spider silk protein;
   (ii) providing a solution of said spider silk protein in a liquid medium at pH 6.4 or higher and/or an ion composition that prevents polymerisation of said spider silk protein, optionally involving removal of lipopolysaccharides and other pyrogens;
   (iii) adjusting the properties of said liquid medium to a pH of 6.3 or lower and an ion composition that allows polymerisation of said spider silk protein;
   (iv) allowing the spider silk protein to form polymers in the liquid medium, said liquid medium having a pH of 6.3 or lower and an ion composition that allows polymerisation of said spider silk protein; and
   (v) isolating the spider silk protein polymers from said liquid medium.

2. A method according to claim 1, wherein the pH of the liquid medium of steps (iii) and (iv) is 6.2 or lower, and/or wherein the pH of the liquid medium of steps (iii) and (iv) is 3 or higher.

3. A method according to claim 1, wherein the ionic strength of the liquid medium of steps (iii) and (iv) is in the range of 1-250 mM.

4. A method according to claim 1, wherein the pH of the liquid medium of step (ii) is 6.7 or higher.

5. A method according to claim 1, wherein the pH of the liquid medium of step (ii) is in the range of 6.4-6.8.

6. A method according to claim 1, wherein said polymer is a fiber, film, foam, net or mesh.

7. A method according to claim 6, wherein said polymer is a fiber having a diameter of more than 0.1 µm and a length of more than 5 mm.

8. A method according to claim 1, wherein step (i) of providing said spider silk protein comprises the sub-steps of:
   (a) expressing a polynucleic acid molecule which encodes said spider silk protein in a suitable host; and
   (b) isolating the protein obtained in sub-step (a), optionally involving removal of lipopolysaccharides and other pyrogens.

9. A method according to claim 1, wherein the spider silk protein provided in step (i) is consisting of from 170 to 600 amino acid residues and comprising a single N-terminal fragment of from 100 to 160 amino acid residues derived from the N-terminal fragment of a spider silk protein.

10. A method according to claim 1, wherein the N-terminal fragment of the spider silk protein provided in step (i) is comprising at least two fragments of from 100 to 160 amino acid residues derived from the N terminal fragment of a spider silk protein.

11. A method according to claim 1, wherein said protein is selected from the group of proteins defined by the formulas $NT_2$-REP-CT, NT-REP-CT, $NT_2$-REP and NT-REP, wherein
   NT is a protein fragment having from 100 to 160 amino acid residues, which fragment is a N-terminal fragment derived from a spider silk protein;
   REP is a protein fragment having from 70 to 300 amino acid residues, wherein said fragment is selected from the group of $L(AG)_nL$, $L(AG)_nAL$, $L(GA)_nL$, $L(GA)_nGL$, wherein
      n is an integer from 2 to 10;
      each individual A segment is an amino acid sequence of from 8 to 18 amino acid residues, wherein from zero to 3 of the amino acid residues are not Ala, and the remaining amino acid residues are Ala;
      each individual G segment is an amino acid sequence of from 12 to 30 amino acid residues, wherein at least 40% of the amino acid residues are Gly; and
      each individual L segment is a linker amino acid sequence of from 0 to 20 amino acid residues; and
   CT is a protein fragment having from 70 to 120 amino acid residues, which fragment is a C-terminal fragment derived from a spider silk protein.

12. A method according to claim 1, wherein the NT fragment has at least 50% identity to SEQ ID NO: 8 and/or at least 80% identity to SEQ ID NO: 6 or SEQ ID NOs: 33-46.

13. A method according to claim 1, wherein the CT fragment has least 50% identity to SEQ ID NO: 9; and/or at least 80% identity to SEQ ID NO: 7 or SEQ ID NOs: 51-81.

14. A method according to claim 1, wherein the spider silk protein consisting of from 170 to 760 amino acid residues comprises the CT fragment of from 70 to 120 amino acid residues, which fragment is derived from the CT fragment of a spider silk protein.

15. A method according to claim 11, wherein the spider silk protein consisting of from 170 to 760 amino acid residues comprises the CT fragment of from 70 to 120 amino acid residues, which fragment is derived from the CT fragment of a spider silk protein.

16. A method according to claim 2, wherein the pH of the liquid medium of steps (iii) and (iv) is 6.0 or lower.

17. A method according to claim 4, wherein the pH of the liquid medium of step (ii) is 7.0 or higher.

18. A method according to claim 2, wherein the pH of the liquid medium of steps (iii) and (iv) is 4.2 or higher.

* * * * *

SEQUENCE LISTING

```
<160> NUMBER OF SEQ ID NOS: 81

<210> SEQ ID NO 1
<211> LENGTH: 149
<212> TYPE: PRT
<213> ORGANISM: Euprosthenops australis

<400> SEQUENCE: 1

Gly Ser Gly Asn Ser Gly Ile Gln Gly Gln Gly Gly Tyr Gly Gly Leu
1               5                   10                  15

Gly Gln Gly Gly Tyr Gly Gln Gly Ala Gly Ser Ser Ala Ala Ala Ala
            20                  25                  30

Ala Ala Ala Ala Ala Ala Ala Ala Gly Gly Gln Gly Gly Gln Gly Gln
        35                  40                  45

Gly Gly Tyr Gly Gln Gly Ser Gly Gly Ser Ala Ala Ala Ala Ala Ala
    50                  55                  60

Ala Ala Ala Ala Ala Ala Ala Ala Ala Gly Arg Gly Gln Gly Gly Tyr
65                  70                  75                  80

Gly Gln Gly Ser Gly Gly Asn Ala Ala Ala Ala Ala Ala Ala Ala Ala
                85                  90                  95

Ala Ala Ala Ala Ala Gly Gln Gly Gly Gln Gly Gly Tyr Gly Arg Gln
            100                 105                 110

Ser Gln Gly Ala Gly Ser Ala Ala Ala Ala Ala Ala Ala Ala Ala Ala
        115                 120                 125

Ala Ala Ala Ala Gly Ser Gly Gln Gly Gly Tyr Gly Gln Gly Gln Gly
    130                 135                 140

Gly Tyr Gly Gln Ser
145

<210> SEQ ID NO 2
<211> LENGTH: 265
<212> TYPE: PRT
<213> ORGANISM: Euprosthenops australis
```

```
<220> FEATURE:
<221> NAME/KEY: DOMAIN
<222> LOCATION: (1)..(167)
<223> OTHER INFORMATION: REP fragment
<220> FEATURE:
<221> NAME/KEY: DOMAIN
<222> LOCATION: (168)..(265)
<223> OTHER INFORMATION: CT fragment

<400> SEQUENCE: 2

Gly Ser Gly Asn Ser Gly Ile Gln Gly Gln Gly Gly Tyr Gly Gly Leu
1               5                   10                  15

Gly Gln Gly Gly Tyr Gly Gln Gly Ala Gly Ser Ser Ala Ala Ala Ala
            20                  25                  30

Ala Ala Ala Ala Ala Ala Ala Ala Gly Gly Gln Gly Gly Gln Gly Gln
        35                  40                  45

Gly Tyr Gly Gln Gly Ser Gly Gly Ser Ala Ala Ala Ala Ala Ala Ala
50                  55                  60

Ala Ala Ala Ala Ala Ala Ala Ala Gly Arg Gly Gln Gly Gly Tyr
65                  70                  75                  80

Gly Gln Gly Ser Gly Gly Asn Ala Ala Ala Ala Ala Ala Ala Ala Ala
                85                  90                  95

Ala Ala Ala Ala Ala Gly Gln Gly Gly Gln Gly Gly Tyr Gly Arg Gln
            100                 105                 110

Ser Gln Gly Ala Gly Ser Ala Ala Ala Ala Ala Ala Ala Ala Ala Ala
            115                 120                 125

Ala Ala Ala Ala Gly Ser Gly Gln Gly Gly Tyr Gly Gln Gly Gln Gly
        130                 135                 140

Gly Tyr Gly Gln Ser Ser Ala Ser Ala Ser Ala Ala Ala Ser Ala Ala
145                 150                 155                 160

Ser Thr Val Ala Asn Ser Val Ser Arg Leu Ser Ser Pro Ser Ala Val
                165                 170                 175

Ser Arg Val Ser Ser Ala Val Ser Ser Leu Val Ser Asn Gly Gln Val
            180                 185                 190

Asn Met Ala Ala Leu Pro Asn Ile Ile Ser Asn Ile Ser Ser Ser Val
        195                 200                 205

Ser Ala Ser Ala Pro Gly Ala Ser Gly Cys Glu Val Ile Val Gln Ala
    210                 215                 220

Leu Leu Glu Val Ile Thr Ala Leu Val Gln Ile Val Ser Ser Ser Ser
225                 230                 235                 240

Val Gly Tyr Ile Asn Pro Ser Ala Val Asn Gln Ile Thr Asn Val Val
                245                 250                 255

Ala Asn Ala Met Ala Gln Val Met Gly
            260                 265

<210> SEQ ID NO 3
<211> LENGTH: 296
<212> TYPE: PRT
<213> ORGANISM: Euprosthenops australis
<220> FEATURE:
<221> NAME/KEY: DOMAIN
<222> LOCATION: (1)..(137)
<223> OTHER INFORMATION: NT fragment
<220> FEATURE:
<221> NAME/KEY: DOMAIN
<222> LOCATION: (138)..(296)
<223> OTHER INFORMATION: REP fragment
```

-continued

```
<400> SEQUENCE: 3

Gly Ser Gly Asn Ser His Thr Thr Pro Trp Thr Asn Pro Gly Leu Ala
1               5                   10                  15

Glu Asn Phe Met Asn Ser Phe Met Gln Gly Leu Ser Ser Met Pro Gly
            20                  25                  30

Phe Thr Ala Ser Gln Leu Asp Asp Met Ser Thr Ile Ala Gln Ser Met
        35                  40                  45

Val Gln Ser Ile Gln Ser Leu Ala Ala Gln Gly Arg Thr Ser Pro Asn
50                  55                  60

Lys Leu Gln Ala Leu Asn Met Ala Phe Ala Ser Ser Met Ala Glu Ile
65                  70                  75                  80

Ala Ala Ser Glu Glu Gly Gly Gly Ser Leu Ser Thr Lys Thr Ser Ser
                85                  90                  95

Ile Ala Ser Ala Met Ser Asn Ala Phe Leu Gln Thr Thr Gly Val Val
            100                 105                 110

Asn Gln Pro Phe Ile Asn Glu Ile Thr Gln Leu Val Ser Met Phe Ala
        115                 120                 125

Gln Ala Gly Met Asn Asp Val Ser Ala Ser Ala Ser Ala Gly Ala Ser
    130                 135                 140

Ala Ala Ala Ser Ala Gly Ala Ala Ser Gly Gln Gly Tyr Gly Gly
145                 150                 155                 160

Leu Gly Gln Gly Gly Tyr Gly Gln Gly Ala Gly Ser Ser Ala Ala Ala
                165                 170                 175

Ala Ala Ala Ala Ala Ala Ala Ala Gly Gln Gly Gly Gln Gly
            180                 185                 190

Gln Gly Gly Tyr Gly Gln Gly Ser Gly Gly Ser Ala Ala Ala Ala
        195                 200                 205

Ala Ala Ala Ala Ala Ala Ala Ala Gly Arg Gly Gln Gly Gly
    210                 215                 220

Tyr Gly Gln Gly Ser Gly Gly Asn Ala Ala Ala Ala Ala Ala Ala Ala
225                 230                 235                 240

Ala Ala Ala Ala Ala Ala Gly Gln Gly Gly Gln Gly Gly Tyr Gly
                245                 250                 255

Arg Gln Ser Gln Gly Ala Gly Ser Ala Ala Ala Ala Ala Ala Ala Ala
            260                 265                 270

Ala Ala Ala Ala Ala Gly Ser Gly Gln Gly Gly Tyr Gly Gly Gln
        275                 280                 285

Gly Gln Gly Gly Tyr Gly Gln Ser
    290                 295

<210> SEQ ID NO 4
<211> LENGTH: 340
<212> TYPE: PRT
<213> ORGANISM: Euprosthenops australis
<220> FEATURE:
<221> NAME/KEY: DOMAIN
<222> LOCATION: (1)..(137)
<223> OTHER INFORMATION: NT fragment
<220> FEATURE:
<221> NAME/KEY: DOMAIN
<222> LOCATION: (138)..(340)
<223> OTHER INFORMATION: REP fragment

<400> SEQUENCE: 4

Gly Ser Gly Asn Ser His Thr Thr Pro Trp Thr Asn Pro Gly Leu Ala
1               5                   10                  15

Glu Asn Phe Met Asn Ser Phe Met Gln Gly Leu Ser Ser Met Pro Gly
            20                  25                  30
```

```
Phe Thr Ala Ser Gln Leu Asp Asp Met Ser Thr Ile Ala Gln Ser Met
         35                  40                  45

Val Gln Ser Ile Gln Ser Leu Ala Ala Gln Gly Arg Thr Ser Pro Asn
 50                  55                  60

Lys Leu Gln Ala Leu Asn Met Ala Phe Ala Ser Ser Met Ala Glu Ile
 65                  70                  75                  80

Ala Ala Ser Glu Glu Gly Gly Ser Leu Ser Thr Lys Thr Ser Ser
                 85                  90                  95

Ile Ala Ser Ala Met Ser Asn Ala Phe Leu Gln Thr Thr Gly Val Val
                100                 105                 110

Asn Gln Pro Phe Ile Asn Glu Ile Thr Gln Leu Val Ser Met Phe Ala
                115                 120                 125

Gln Ala Gly Met Asn Asp Val Ser Ala Ser Ala Ser Ala Gly Ala Ser
            130                 135                 140

Ala Ala Ala Ser Ala Gly Ala Pro Gly Tyr Ser Pro Ala Pro Ser Tyr
145                 150                 155                 160

Ser Ser Gly Gly Tyr Ala Ser Ser Ala Ala Ser Ala Ala Ala Ala Ala
                165                 170                 175

Gly Gln Gly Gly Pro Gly Gly Tyr Gly Pro Ala Pro Asn Gln Gly Ala
            180                 185                 190

Ser Ser Ala Ala Ala Ala Ala Gly Ser Gly Gln Gly Pro Ser Gly
        195                 200                 205

Pro Tyr Gly Thr Ser Tyr Gln Ile Ser Thr Gln Tyr Thr Gln Thr Thr
        210                 215                 220

Thr Ser Gln Gly Gln Gly Tyr Gly Ser Ser Ser Ala Gly Ala Ala Ala
225                 230                 235                 240

Ala Gly Ala Ala Ala Gly Gln Gly Tyr Gly Gln Gly Gln
            245                 250                 255

Gly Gly Tyr Gly Gln Gly Ala Gly Gly Ala Ala Ala Ala Ala Ala
            260                 265                 270

Ala Ala Ala Ala Ala Ala Ala Gly Gln Gly Gly Gln Gly Gly Gly
        275                 280                 285

Gly Tyr Gly Gln Gly Gly Gln Gly Gly Gln Gly Gly Gln Gly Gln Gly
        290                 295                 300

Gly Tyr Gly Gln Gly Ala Gly Ser Ser Ala Ala Ala Ala Ala Ala
305                 310                 315                 320

Ala Ala Ala Ala Ala Ala Gly Arg Gly Gln Gly Gly Tyr Gly Pro
            325                 330                 335

Gly Ser Gly Gly
        340

<210> SEQ ID NO 5
<211> LENGTH: 424
<212> TYPE: PRT
<213> ORGANISM: Euprosthenops australis
<220> FEATURE:
<221> NAME/KEY: DOMAIN
<222> LOCATION: (1)..(136)
<223> OTHER INFORMATION: NT fragment
<220> FEATURE:
<221> NAME/KEY: DOMAIN
<222> LOCATION: (137)..(313)
<223> OTHER INFORMATION: REP fragment
<220> FEATURE:
<221> NAME/KEY: DOMAIN
<222> LOCATION: (314)..(411)
<223> OTHER INFORMATION: CT fragment
```

<220> FEATURE:
<221> NAME/KEY: DOMAIN
<222> LOCATION: (412)..(424)
<223> OTHER INFORMATION: His tag

<400> SEQUENCE: 5

Met Lys Ala Ser His Thr Thr Pro Trp Thr Asn Pro Gly Leu Ala Glu
1               5                   10                  15

Asn Phe Met Asn Ser Phe Met Gln Gly Leu Ser Ser Met Pro Gly Phe
            20                  25                  30

Thr Ala Ser Gln Leu Asp Asp Met Ser Thr Ile Ala Gln Ser Met Val
        35                  40                  45

Gln Ser Ile Gln Ser Leu Ala Ala Gln Gly Arg Thr Ser Pro Asn Lys
    50                  55                  60

Leu Gln Ala Leu Asn Met Ala Phe Ala Ser Ser Met Ala Glu Ile Ala
65                  70                  75                  80

Ala Ser Glu Glu Gly Gly Gly Ser Leu Ser Thr Lys Thr Ser Ser Ile
                85                  90                  95

Ala Ser Ala Met Ser Asn Ala Phe Leu Gln Thr Thr Gly Val Val Asn
            100                 105                 110

Gln Pro Phe Ile Asn Glu Ile Thr Gln Leu Val Ser Met Phe Ala Gln
        115                 120                 125

Ala Gly Met Asn Asp Val Ser Ala Ser Ala Ser Gly Ala Ser Ala
    130                 135                 140

Ala Ala Ser Ala Gly Ala Ala Ser Gly Gln Gly Gly Tyr Gly Gly Leu
145                 150                 155                 160

Gly Gln Gly Gly Tyr Gly Gln Gly Ala Gly Ser Ser Ala Ala Ala
                165                 170                 175

Ala Ala Ala Ala Ala Ala Ala Gly Gly Gln Gly Gly Gln Gly Gln
            180                 185                 190

Gly Gly Tyr Gly Gln Gly Ser Gly Gly Ser Ala Ala Ala Ala Ala
                195                 200                 205

Ala Ala Ala Ala Ala Ala Ala Ala Gly Arg Gly Gln Gly Gly Tyr
    210                 215                 220

Gly Gln Gly Ser Gly Gly Asn Ala Ala Ala Ala Ala Ala Ala Ala
225                 230                 235                 240

Ala Ala Ala Ala Ala Gly Gln Gly Gly Gln Gly Gly Tyr Gly Arg
                245                 250                 255

Gln Ser Gln Gly Ala Gly Ser Ala Ala Ala Ala Ala Ala Ala Ala
        260                 265                 270

Ala Ala Ala Ala Gly Ser Gly Gln Gly Gly Tyr Gly Gly Gln Gly
    275                 280                 285

Gln Gly Gly Tyr Gly Gln Ser Ser Ala Ser Ala Ser Ala Ala Ser
        290                 295                 300

Ala Ala Ser Thr Val Ala Asn Ser Val Ser Arg Leu Ser Ser Pro Ser
305                 310                 315                 320

Ala Val Ser Arg Val Ser Ser Ala Val Ser Ser Leu Val Ser Asn Gly
            325                 330                 335

Gln Val Asn Met Ala Ala Leu Pro Asn Ile Ile Ser Asn Ile Ser Ser
        340                 345                 350

Ser Val Ser Ala Ser Ala Pro Gly Ala Ser Gly Cys Glu Val Ile Val
            355                 360                 365

Gln Ala Leu Leu Glu Val Ile Thr Ala Leu Val Gln Ile Val Ser Ser
        370                 375                 380

Ser Ser Val Gly Tyr Ile Asn Pro Ser Ala Val Asn Gln Ile Thr Asn

```
                385                 390                 395                 400
Val Val Ala Asn Ala Met Ala Gln Val Met Gly Lys Leu Ala Ala Ala
                405                 410                 415

Leu Glu His His His His His His
        420

<210> SEQ ID NO 6
<211> LENGTH: 137
<212> TYPE: PRT
<213> ORGANISM: Euprosthenops australis
<220> FEATURE:
<221> NAME/KEY: VARIANT
<222> LOCATION: (6)..(6)
<223> OTHER INFORMATION: deletion (deltaHis)

<400> SEQUENCE: 6

Gly Ser Gly Asn Ser His Thr Thr Pro Trp Thr Asn Pro Gly Leu Ala
1               5                   10                  15

Glu Asn Phe Met Asn Ser Phe Met Gln Gly Leu Ser Ser Met Pro Gly
            20                  25                  30

Phe Thr Ala Ser Gln Leu Asp Asp Met Ser Thr Ile Ala Gln Ser Met
        35                  40                  45

Val Gln Ser Ile Gln Ser Leu Ala Ala Gln Gly Arg Thr Ser Pro Asn
    50                  55                  60

Lys Leu Gln Ala Leu Asn Met Ala Phe Ala Ser Ser Met Ala Glu Ile
65                  70                  75                  80

Ala Ala Ser Glu Glu Gly Gly Gly Ser Leu Ser Thr Lys Thr Ser Ser
                85                  90                  95

Ile Ala Ser Ala Met Ser Asn Ala Phe Leu Gln Thr Thr Gly Val Val
            100                 105                 110

Asn Gln Pro Phe Ile Asn Glu Ile Thr Gln Leu Val Ser Met Phe Ala
        115                 120                 125

Gln Ala Gly Met Asn Asp Val Ser Ala
    130                 135

<210> SEQ ID NO 7
<211> LENGTH: 98
<212> TYPE: PRT
<213> ORGANISM: Euprosthenops australis

<400> SEQUENCE: 7

Ser Arg Leu Ser Ser Pro Ser Ala Val Ser Arg Val Ser Ser Ala Val
1               5                   10                  15

Ser Ser Leu Val Ser Asn Gly Gln Val Asn Met Ala Ala Leu Pro Asn
            20                  25                  30

Ile Ile Ser Asn Ile Ser Ser Val Ser Ala Ser Ala Pro Gly Ala
        35                  40                  45

Ser Gly Cys Glu Val Ile Val Gln Ala Leu Leu Glu Val Ile Thr Ala
    50                  55                  60

Leu Val Gln Ile Val Ser Ser Ser Val Gly Tyr Ile Asn Pro Ser
65                  70                  75                  80

Ala Val Asn Gln Ile Thr Asn Val Val Ala Asn Ala Met Ala Gln Val
                85                  90                  95

Met Gly

<210> SEQ ID NO 8
<211> LENGTH: 131
<212> TYPE: PRT
<213> ORGANISM: Artificial Sequence
```

```
<220> FEATURE:
<223> OTHER INFORMATION: Consensus sequence derived from spidroin NT
      fragments
<220> FEATURE:
<221> NAME/KEY: VARIANT
<222> LOCATION: (20)..(20)
<223> OTHER INFORMATION: Leu
<220> FEATURE:
<221> NAME/KEY: VARIANT
<222> LOCATION: (42)..(42)
<223> OTHER INFORMATION: Asn
<220> FEATURE:
<221> NAME/KEY: VARIANT
<222> LOCATION: (42)..(42)
<223> OTHER INFORMATION: Gln
<220> FEATURE:
<221> NAME/KEY: VARIANT
<222> LOCATION: (50)..(50)
<223> OTHER INFORMATION: Ser
<220> FEATURE:
<221> NAME/KEY: VARIANT
<222> LOCATION: (50)..(50)
<223> OTHER INFORMATION: Lys
<220> FEATURE:
<221> NAME/KEY: VARIANT
<222> LOCATION: (56)..(56)
<223> OTHER INFORMATION: Arg
<220> FEATURE:
<221> NAME/KEY: VARIANT
<222> LOCATION: (84)..(84)
<223> OTHER INFORMATION: Leu
<220> FEATURE:
<221> NAME/KEY: VARIANT
<222> LOCATION: (114)..(114)
<223> OTHER INFORMATION: Ser
<220> FEATURE:
<221> NAME/KEY: VARIANT
<222> LOCATION: (121)..(121)
<223> OTHER INFORMATION: Asn
<220> FEATURE:
<221> NAME/KEY: VARIANT
<222> LOCATION: (123)..(123)
<223> OTHER INFORMATION: Leu
<220> FEATURE:
<221> NAME/KEY: VARIANT
<222> LOCATION: (124)..(124)
<223> OTHER INFORMATION: Ser

<400> SEQUENCE: 8

Gln Ala Asn Thr Pro Trp Ser Ser Pro Asn Leu Ala Asp Ala Phe Ile
1               5                   10                  15

Asn Ser Phe Met Ser Ala Ala Ser Ser Gly Ala Phe Ser Ala Asp
            20                  25                  30

Gln Leu Asp Asp Met Ser Thr Ile Gly Asp Thr Leu Met Ser Ala Met
        35                  40                  45

Asp Asn Met Gly Arg Ser Gly Lys Ser Thr Lys Ser Lys Leu Gln Ala
50                  55                  60

Leu Asn Met Ala Phe Ala Ser Ser Met Ala Glu Ile Ala Ala Ala Glu
65                  70                  75                  80

Ser Gly Gly Gly Ser Val Gly Val Lys Thr Asn Ala Ile Ser Asp Ala
                85                  90                  95

Leu Ser Ser Ala Phe Tyr Gln Thr Thr Gly Ser Val Asn Pro Gln Phe
            100                 105                 110

Val Asn Glu Ile Arg Ser Leu Ile Gly Met Phe Ala Gln Ala Ser Ala
        115                 120                 125

Asn Glu Val
        130

<210> SEQ ID NO 9
<211> LENGTH: 100
```

-continued

```
<212> TYPE: PRT
<213> ORGANISM: Artificial Sequence
<220> FEATURE:
<223> OTHER INFORMATION: Consensus sequence derived from known MaSp1
      and MaSp2 proteins
<220> FEATURE:
<221> NAME/KEY: MISC_FEATURE
<222> LOCATION: (1)..(71)
<223> OTHER INFORMATION: Sequence length present in known species
      variants
<220> FEATURE:
<221> NAME/KEY: VARIANT
<222> LOCATION: (7)..(7)
<223> OTHER INFORMATION: Glu

<400> SEQUENCE: 9

Ser Arg Leu Ser Ser Pro Gln Ala Ser Ser Arg Val Ser Ala Val
1               5                   10                  15

Ser Asn Leu Val Ser Ser Gly Pro Thr Asn Ser Ala Ala Leu Ser Asn
                20                  25                  30

Thr Ile Ser Asn Val Val Ser Gln Ile Ser Ala Ser Asn Pro Gly Leu
                35                  40                  45

Ser Gly Cys Asp Val Leu Val Gln Ala Leu Leu Glu Val Val Ser Ala
            50                  55                  60

Leu Val His Ile Leu Gly Ser Ser Ser Ile Gly Gln Val Asn Tyr Gly
65              70                  75                  80

Ser Ala Gly Gln Ala Thr Gln Ile Val Gly Gln Ser Val Ala Gln Ala
                85                  90                  95

Leu Gly Glu Phe
            100

<210> SEQ ID NO 10
<211> LENGTH: 1110
<212> TYPE: PRT
<213> ORGANISM: Euprosthenops australis
<220> FEATURE:
<221> NAME/KEY: REPEAT
<222> LOCATION: (7)..(19)
<220> FEATURE:
<221> NAME/KEY: REPEAT
<222> LOCATION: (20)..(42)
<220> FEATURE:
<221> NAME/KEY: REPEAT
<222> LOCATION: (43)..(56)
<220> FEATURE:
<221> NAME/KEY: REPEAT
<222> LOCATION: (57)..(70)
<220> FEATURE:
<221> NAME/KEY: REPEAT
<222> LOCATION: (71)..(83)
<220> FEATURE:
<221> NAME/KEY: REPEAT
<222> LOCATION: (84)..(106)
<220> FEATURE:
<221> NAME/KEY: REPEAT
<222> LOCATION: (107)..(120)
<220> FEATURE:
<221> NAME/KEY: REPEAT
<222> LOCATION: (121)..(134)
<220> FEATURE:
<221> NAME/KEY: REPEAT
<222> LOCATION: (135)..(147)
<220> FEATURE:
<221> NAME/KEY: REPEAT
<222> LOCATION: (148)..(170)
<220> FEATURE:
<221> NAME/KEY: REPEAT
<222> LOCATION: (171)..(183)
<220> FEATURE:
<221> NAME/KEY: REPEAT
<222> LOCATION: (184)..(197)
<220> FEATURE:
```

```
<221> NAME/KEY: REPEAT
<222> LOCATION: (198)..(211)
<220> FEATURE:
<221> NAME/KEY: REPEAT
<222> LOCATION: (212)..(234)
<220> FEATURE:
<221> NAME/KEY: REPEAT
<222> LOCATION: (235)..(248)
<220> FEATURE:
<221> NAME/KEY: REPEAT
<222> LOCATION: (249)..(265)
<220> FEATURE:
<221> NAME/KEY: REPEAT
<222> LOCATION: (266)..(279)
<220> FEATURE:
<221> NAME/KEY: REPEAT
<222> LOCATION: (280)..(293)
<220> FEATURE:
<221> NAME/KEY: REPEAT
<222> LOCATION: (294)..(306)
<220> FEATURE:
<221> NAME/KEY: REPEAT
<222> LOCATION: (307)..(329)
<220> FEATURE:
<221> NAME/KEY: REPEAT
<222> LOCATION: (330)..(342)
<220> FEATURE:
<221> NAME/KEY: REPEAT
<222> LOCATION: (343)..(356)
<220> FEATURE:
<221> NAME/KEY: REPEAT
<222> LOCATION: (357)..(370)
<220> FEATURE:
<221> NAME/KEY: REPEAT
<222> LOCATION: (371)..(393)
<220> FEATURE:
<221> NAME/KEY: REPEAT
<222> LOCATION: (394)..(406)
<220> FEATURE:
<221> NAME/KEY: REPEAT
<222> LOCATION: (407)..(420)
<220> FEATURE:
<221> NAME/KEY: REPEAT
<222> LOCATION: (421)..(434)
<220> FEATURE:
<221> NAME/KEY: REPEAT
<222> LOCATION: (435)..(457)
<220> FEATURE:
<221> NAME/KEY: REPEAT
<222> LOCATION: (458)..(470)
<220> FEATURE:
<221> NAME/KEY: REPEAT
<222> LOCATION: (471)..(488)
<220> FEATURE:
<221> NAME/KEY: REPEAT
<222> LOCATION: (489)..(502)
<220> FEATURE:
<221> NAME/KEY: REPEAT
<222> LOCATION: (503)..(516)
<220> FEATURE:
<221> NAME/KEY: REPEAT
<222> LOCATION: (517)..(529)
<220> FEATURE:
<221> NAME/KEY: REPEAT
<222> LOCATION: (530)..(552)
<220> FEATURE:
<221> NAME/KEY: REPEAT
<222> LOCATION: (553)..(566)
<220> FEATURE:
<221> NAME/KEY: REPEAT
<222> LOCATION: (567)..(580)
<220> FEATURE:
<221> NAME/KEY: REPEAT
<222> LOCATION: (581)..(594)
<220> FEATURE:
<221> NAME/KEY: REPEAT
<222> LOCATION: (595)..(617)
<220> FEATURE:
<221> NAME/KEY: REPEAT
<222> LOCATION: (618)..(630)
```

```
<220> FEATURE:
<221> NAME/KEY: REPEAT
<222> LOCATION: (631)..(647)
<220> FEATURE:
<221> NAME/KEY: REPEAT
<222> LOCATION: (648)..(661)
<220> FEATURE:
<221> NAME/KEY: REPEAT
<222> LOCATION: (662)..(675)
<220> FEATURE:
<221> NAME/KEY: REPEAT
<222> LOCATION: (676)..(688)
<220> FEATURE:
<221> NAME/KEY: REPEAT
<222> LOCATION: (689)..(711)
<220> FEATURE:
<221> NAME/KEY: REPEAT
<222> LOCATION: (712)..(725)
<220> FEATURE:
<221> NAME/KEY: REPEAT
<222> LOCATION: (726)..(739)
<220> FEATURE:
<221> NAME/KEY: REPEAT
<222> LOCATION: (740)..(752)
<220> FEATURE:
<221> NAME/KEY: REPEAT
<222> LOCATION: (753)..(775)
<220> FEATURE:
<221> NAME/KEY: REPEAT
<222> LOCATION: (776)..(789)
<220> FEATURE:
<221> NAME/KEY: REPEAT
<222> LOCATION: (790)..(803)
<220> FEATURE:
<221> NAME/KEY: REPEAT
<222> LOCATION: (804)..(816)
<220> FEATURE:
<221> NAME/KEY: REPEAT
<222> LOCATION: (817)..(839)
<220> FEATURE:
<221> NAME/KEY: REPEAT
<222> LOCATION: (840)..(853)
<220> FEATURE:
<221> NAME/KEY: REPEAT
<222> LOCATION: (854)..(867)
<220> FEATURE:
<221> NAME/KEY: REPEAT
<222> LOCATION: (868)..(880)
<220> FEATURE:
<221> NAME/KEY: REPEAT
<222> LOCATION: (881)..(903)
<220> FEATURE:
<221> NAME/KEY: REPEAT
<222> LOCATION: (904)..(917)
<220> FEATURE:
<221> NAME/KEY: REPEAT
<222> LOCATION: (918)..(931)
<220> FEATURE:
<221> NAME/KEY: REPEAT
<222> LOCATION: (932)..(945)
<220> FEATURE:
<221> NAME/KEY: REPEAT
<222> LOCATION: (946)..(968)
<220> FEATURE:
<221> NAME/KEY: REPEAT
<222> LOCATION: (969)..(981)
<220> FEATURE:
<221> NAME/KEY: REPEAT
<222> LOCATION: (982)..(998)
<220> FEATURE:
<221> NAME/KEY: REPEAT
<222> LOCATION: (999)..(1013)
<220> FEATURE:
<221> NAME/KEY: REPEAT
<222> LOCATION: (1014)..(1027)
<220> FEATURE:
<221> NAME/KEY: REPEAT
<222> LOCATION: (1028)..(1042)
<220> FEATURE:
<221> NAME/KEY: REPEAT
```

<222> LOCATION: (1043)..(1059)
<220> FEATURE:
<221> NAME/KEY: REPEAT
<222> LOCATION: (1060)..(1073)
<220> FEATURE:
<221> NAME/KEY: REPEAT
<222> LOCATION: (1074)..(1092)

<400> SEQUENCE: 10

Gln Gly Ala Gly Gly Asn Ala Ala Ala Ala Ala Ala Ala Ala Ala
1               5                   10                  15

Ala Ala Ala Gly Gln Gly Gly Gln Gly Gly Tyr Gly Gly Leu Gly Gln
            20                  25                  30

Gly Gly Tyr Gly Gln Gly Ala Gly Ser Ser Ala Ala Ala Ala Ala
            35                  40                  45

Ala Ala Ala Ala Ala Ala Ala Gly Arg Gly Gln Gly Gly Tyr Gly
    50                  55                  60

Gln Gly Ser Gly Gly Asn Ala Ala Ala Ala Ala Ala Ala Ala Ala
65                  70                  75                  80

Ala Ala Ser Gly Gln Gly Gly Gln Gly Gly Gln Gly Gly Gln
            85                  90                  95

Gly Gly Tyr Gly Gln Gly Ala Gly Ser Ser Ala Ala Ala Ala Ala
            100                 105                 110

Ala Ala Ala Ala Ala Ala Ala Gly Gln Gly Gln Gly Arg Tyr Gly
            115                 120                 125

Gln Gly Ala Gly Gly Asn Ala Ala Ala Ala Ala Ala Ala Ala Ala
130                 135                 140

Ala Ala Ala Gly Gln Gly Gly Gln Gly Gly Gln Gly Gly Leu Gly Gln
145                 150                 155                 160

Gly Gly Tyr Gly Gln Gly Ala Gly Ser Ser Ala Ala Ala Ala Ala
            165                 170                 175

Ser Ala Ala Ala Ala Ala Ala Gly Arg Gly Gln Gly Gly Tyr Gly Gln
            180                 185                 190

Gly Ala Gly Gly Asn Ala Ala Ala Ala Ala Ala Ala Ala Ala
            195                 200                 205

Ala Ala Ala Gly Gln Gly Gly Gln Gly Gly Tyr Gly Gly Leu Gly Gln
            210                 215                 220

Gly Gly Tyr Gly Gln Gly Ala Gly Ser Ser Ala Ala Ala Ala Ala
225                 230                 235                 240

Ala Ala Ala Ala Ala Ala Gly Gly Gln Gly Gly Gln Gly Gln Gly
            245                 250                 255

Arg Tyr Gly Gln Gly Ala Gly Ser Ser Ala Ala Ala Ala Ala Ala
            260                 265                 270

Ala Ala Ala Ala Ala Ala Gly Gln Gly Gln Gly Gly Tyr Gly Gln
            275                 280                 285

Gly Ala Gly Gly Asn Ala Ala Ala Ala Ala Ala Ala Ala Ala Ala
            290                 295                 300

Ala Ala Gly Gln Gly Gly Gln Gly Gly Gln Gly Gly Leu Gly Gln Gly
305                 310                 315                 320

Gly Tyr Gly Gln Gly Ala Gly Ser Ser Ala Ala Ala Ala Ala Ala
            325                 330                 335

Ala Ala Ala Ala Ala Ala Gly Arg Gly Gln Gly Gly Tyr Gly Gln Gly
            340                 345                 350

Ala Gly Gly Asn Ala Ala Ala Ala Ala Ala Ala Ala Glu Ala Ala
            355                 360                 365

Ala Ala Gly Gln Gly Gly Gln Gly Gly Tyr Gly Gly Leu Gly Gln Gly

-continued

```
            370                 375                 380
Gly Tyr Gly Gln Gly Ala Gly Ser Ser Ala Ala Ala Ala Ala Ala
385                 390                 395                 400
Ala Ala Ala Ala Ala Ala Gly Arg Gly Gln Gly Gly Tyr Gly Gln Gly
                405                 410                 415
Ala Gly Gly Asn Ala Ala Ala Ala Ala Ala Ala Ala Ala Ala
                420                 425                 430
Ala Ala Gly Gln Gly Gly Gln Gly Gly Tyr Gly Gly Leu Gly Gln Gly
                435                 440                 445
Gly Tyr Gly Gln Gly Ala Gly Ser Ser Ala Ala Ala Ala Ala Ala
        450                 455                 460
Ala Ala Ala Ala Ala Gly Gly Gln Gly Gly Gln Gly Gln Gly Arg
465                 470                 475                 480
Tyr Gly Gln Gly Ala Gly Ser Ser Ala Ala Ala Ala Ala Ala
                485                 490                 495
Ala Ala Ala Ala Ala Ala Gly Arg Gly Gln Gly Gly Tyr Gly Gln Gly
                500                 505                 510
Ser Gly Gly Asn Ala Ala Ala Ala Ala Ala Ala Ala Ala Ala Ala
        515                 520                 525
Ser Gly Gln Gly Ser Gln Gly Gly Gln Gly Gly Gln Gly Gly Gly
        530                 535                 540
Tyr Gly Gln Gly Ala Gly Ser Ser Ala Ala Ala Ala Ala Ala Ala
545                 550                 555                 560
Ala Ala Ala Ala Ala Ser Gly Arg Gly Gln Gly Gly Tyr Gly Gln Gly
                565                 570                 575
Ala Gly Gly Asn Ala Ala Ala Ala Ala Ala Ala Ala Ala Ala
                580                 585                 590
Ala Ala Gly Gln Gly Gly Gln Gly Gly Tyr Gly Gly Leu Gly Gln Gly
                595                 600                 605
Gly Tyr Gly Gln Gly Ala Gly Ser Ser Ala Ala Ala Ala Ala Ala
        610                 615                 620
Ala Ala Ala Ala Ala Gly Gly Gln Gly Gly Gln Gly Gln Gly Gly Tyr
625                 630                 635                 640
Gly Gln Gly Ala Gly Ser Ser Ala Ala Ala Ala Ala Ala Ala Ala
                645                 650                 655
Ala Ala Ala Ala Ala Gly Arg Gly Gln Gly Gly Tyr Gly Gln Gly Ser
                660                 665                 670
Gly Gly Asn Ala Ala Ala Ala Ala Ala Ala Ala Ala Ala Ala Ser
        675                 680                 685
Gly Gln Gly Gly Gln Gly Gly Gln Gly Gly Gln Gly Gly Gly Tyr
        690                 695                 700
Gly Gln Gly Ala Gly Ser Ser Ala Ala Ala Ala Ala Ala Ala Ala
705                 710                 715                 720
Ala Ala Ala Ala Ala Gly Gln Gly Gln Gly Gly Tyr Gly Gln Gly Ala
                725                 730                 735
Gly Gly Asn Ala Ala Ala Ala Ala Ala Ala Ala Ala Ala Ala
                740                 745                 750
Gly Gln Gly Gly Gln Gly Gly Gln Gly Gly Leu Gly Gln Gly Gly Tyr
                755                 760                 765
Gly Gln Gly Ala Gly Ser Ser Ala Ala Ala Ala Ala Ala Ala Ala
        770                 775                 780
Ala Ala Ala Ala Ala Gly Arg Gly Gln Gly Gly Tyr Gly Gln Gly Val
785                 790                 795                 800
```

```
Gly Gly Asn Ala Ala Ala Ala Ala Ala Ala Ala Ala Ala
            805                 810                 815

Gly Gln Gly Gly Gln Gly Gly Gln Gly Gly Leu Gly Gln Gly Gly Tyr
        820                 825                 830

Gly Gln Gly Ala Gly Ser Ser Ala Ala Ala Ala Ala Ala Ala
        835                 840                 845

Ala Ala Ala Ala Ala Gly Arg Gly Gln Gly Gly Tyr Gly Gln Gly Ser
850                 855                 860

Gly Gly Asn Ala Ala Ala Ala Ala Ala Ala Ala Ala Ala Ser
865                 870                 875                 880

Gly Gln Gly Ser Gln Gly Gly Gly Gln Gly Gly Gly Tyr
        885                 890                 895

Gly Gln Gly Ala Gly Ser Ser Ala Ala Ala Ala Ala Ala Ala
        900                 905                 910

Ala Ala Ala Ala Ser Gly Arg Gly Gln Gly Gly Tyr Gly Gln Gly Ala
        915                 920                 925

Gly Gly Asn Ala Ala Ala Ala Ala Ala Ala Ala Ala Ala Ala
        930                 935                 940

Ala Gly Gln Gly Gly Gln Gly Gly Tyr Gly Gly Leu Gly Gln Gly Gly
945                 950                 955                 960

Tyr Gly Gln Gly Ala Gly Ser Ser Ala Ala Ala Ala Ala Ala Ala
                965                 970                 975

Ala Ala Ala Ala Gly Gly Gln Gly Gly Gln Gly Gly Gly Tyr Gly
        980                 985                 990

Gln Gly Ser Gly Gly Ser Ala Ala Ala Ala Ala Ala Ala Ala Ala
        995                 1000                1005

Ala Ala Ala Ala Ala Gly Arg Gly Gln Gly Gly Tyr Gly Gln Gly
        1010                1015                1020

Ser Gly Gly Asn Ala Ala Ala Ala Ala Ala Ala Ala Ala Ala
1025                1030                1035

Ala Ala Ala Ala Gly Gln Gly Gly Gln Gly Gly Tyr Gly Arg Gln
        1040                1045                1050

Ser Gln Gly Ala Gly Ser Ala Ala Ala Ala Ala Ala Ala Ala
    1055                1060                1065

Ala Ala Ala Ala Ala Gly Ser Gly Gln Gly Gly Tyr Gly Gly Gln
        1070                1075                1080

Gly Gln Gly Gly Tyr Gly Gln Ser Ser Ala Ser Ala Ser Ala Ala
        1085                1090                1095

Ala Ser Ala Ala Ser Thr Val Ala Asn Ser Val Ser
    1100                1105                1110

<210> SEQ ID NO 11
<211> LENGTH: 23
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (4)..(4)
<223> OTHER INFORMATION: Ser
<220> FEATURE:
<221> NAME/KEY: VARIANT
<222> LOCATION: (8)..(8)
<223> OTHER INFORMATION: Tyr
<220> FEATURE:
<221> NAME/KEY: VARIANT
<222> LOCATION: (11)..(11)
<223> OTHER INFORMATION: Gln
```

-continued

<400> SEQUENCE: 11

Gly Gln Gly Gly Gln Gly Gly Gln Gly Gly Leu Gly Gln Gly Gly Tyr
1               5                   10                  15

Gly Gln Gly Ala Gly Ser Ser
            20

<210> SEQ ID NO 12
<211> LENGTH: 17
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (9)..(9)
<223> OTHER INFORMATION: Arg
<220> FEATURE:
<221> NAME/KEY: VARIANT
<222> LOCATION: (14)..(14)
<223> OTHER INFORMATION: Ser
<220> FEATURE:
<221> NAME/KEY: VARIANT
<222> LOCATION: (16)..(16)
<223> OTHER INFORMATION: Gly

<400> SEQUENCE: 12

Gly Gln Gly Gly Gln Gly Gln Gly Gly Tyr Gly Gln Gly Ala Gly Ser
1               5                   10                  15

Ser

<210> SEQ ID NO 13
<211> LENGTH: 14
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (2)..(2)
<223> OTHER INFORMATION: Gln
<220> FEATURE:
<221> NAME/KEY: VARIANT
<222> LOCATION: (6)..(6)
<223> OTHER INFORMATION: Arg
<220> FEATURE:
<221> NAME/KEY: VARIANT
<222> LOCATION: (11)..(11)
<223> OTHER INFORMATION: Ser
<220> FEATURE:
<221> NAME/KEY: VARIANT
<222> LOCATION: (11)..(11)
<223> OTHER INFORMATION: Val

<400> SEQUENCE: 13

Gly Arg Gly Gln Gly Gly Tyr Gly Gln Gly Ala Gly Gly Asn
1               5                   10

<210> SEQ ID NO 14
<211> LENGTH: 888
<212> TYPE: DNA
<213> ORGANISM: Euprosthenops australis

<400> SEQUENCE: 14
ggttctggga attcacacac tacaccatgg acaaacccag gactcgcaga aaacttcatg      60
aacagtttca tgcaaggcct gagctcgatg ccaggtttca cggcaagcca attggatgat    120
atgtcaacca tcgcacaatc catggtacag tcaatacaat ccttggcggc acaaggcagg    180

```
acatcaccga ataagctgca ggcccttaac atggcttttg catcttcgat ggcagaaatc    240
gcggcatccg aagaaggagg gggaagcctt tccaccaaaa ctagctctat agccagtgca    300
atgtccaacg cgtttctgca aacaactgga gtggtaaacc aaccgttcat aaatgaaata    360
actcagctcg ttagcatgtt tgctcaagca ggtatgaatg atgtcagtgc ttccgcatca    420
gcaggagcat ccgcagcagc atccgcagga gcggctagcg gtcaaggtgg atatggtgga    480
ctaggtcaag gaggatatgg acaaggtgca ggaagttctg cagccgctgc cgccgccgca    540
gcagccgccg cagcaggtgg acaaggtgga caaggtcaag gaggatatgg acaaggttca    600
ggaggttctg cagccgccgc cgccgccgca gcagcagcag cagctgcagc agctggacga    660
ggtcaaggag gatatggtca aggttctgga ggtaatgctg ctgccgcagc cgctgccgcc    720
gccgccgccg ctgcagcagc cggacaggga ggtcaaggtg gatatggtag acaaagccaa    780
ggtgctggtt ccgctgctgc tgctgctgct gctgctgccg ctgctgctgc tgcaggatct    840
ggacaaggtg gatacggtgg acaaggtcaa ggaggttatg gtcagagt              888
```

<210> SEQ ID NO 15
<211> LENGTH: 1272
<212> TYPE: DNA
<213> ORGANISM: Euprosthenops australis

<400> SEQUENCE: 15

```
atgaaagcat cacacactac accatggaca aacccaggac tcgcagaaaa cttcatgaac      60
agtttcatgc aaggcctgag ctcgatgcca ggtttcacgg caagccaatt ggatgatatg    120
tcaaccatcg cacaatccat ggtacagtca atacaatcct tggcggcaca aggcaggaca    180
tcaccgaata agctgcaggc ccttaacatg gcttttgcat cttcgatggc agaaatcgcg    240
gcatccgaag aaggagggg aagccttttcc accaaaacta gctctatagc cagtgcaatg    300
tccaacgcgt ttctgcaaac aactggagtg gtaaaccaac cgttcataaa tgaataact    360 cagctcgtta gcatgtttgc tcaagcaggt atgaatgatg tcagtgcttc cgcatcagca    420
ggagcatccg cagcagcatc cgcaggagcg gctagcggtc aaggtggata tggtggacta    480
ggtcaaggag gatatggaca aggtgcagga agttctgcag ccgctgccgc cgccgcagca    540
gccgccgcag caggtggaca aggtggacaa ggtcaaggag gatatggaca aggttcagga    600
ggttctgcag ccgccgccgc cgccgcagca gcagcagcag ctgcagcagc tggacgaggt    660
caaggaggat atggtcaagg ttctggaggt aatgctgctg ccgcagccgc tgccgccgcc    720
gccgccgctg cagcagccgg acaggaggt caaggtggat atggtagaca aagccaaggt    780
gctggttccg ctgctgctgc tgctgctgct gctgccgctg ctgctgctgc aggatctgga    840
caaggtggat acggtggaca aggtcaagga ggttatggtc agagtagtgc ttctgcttca    900
gctgctgcgt cagctgctag tactgtagct aattcggtga gtcgcctctc atcgccttcc    960
gcagtatctc gagtttcttc agcagtttct agcttggttt caaatggtca agtgaatatg   1020
gcagcgttac ctaatatcat ttccaacatt tcttcttctg tcagtgcatc tgctcctggt   1080
gcttctggat gtgaggtcat agtgcaagct ctactcgaag tcatcactgc tcttgttcaa   1140
atcgttagtt cttctagtgt tggatatatt aatccatctg ctgtgaacca aattactaat   1200
gttgttgcta atgccatggc tcaagtaatg ggcaagcttg cggccgcact cgagcaccac   1260
caccaccacc ac                                                       1272
```

<210> SEQ ID NO 16
<211> LENGTH: 1020

<212> TYPE: DNA
<213> ORGANISM: Euprosthenops australis

<400> SEQUENCE: 16

```
ggttctggga attcacacac tacaccatgg acaaacccag gactcgcaga aaacttcatg    60
aacagtttca tgcaaggcct gagctcgatg ccaggtttca cggcaagcca attggatgat   120
atgtcaacca tcgcacaatc catggtacag tcaatacaat ccttggcggc acaaggcagg   180
acatcaccga ataagctgca ggcccttaac atggcttttg catcttcgat ggcagaaatc   240
gcggcatccg aagaaggagg gggaagcctt tccaccaaaa ctagctctat agccagtgca   300
atgtccaacg cgtttctgca aacaactgga gtggtaaacc aaccgttcat aaatgaaata   360
actcagctcg ttagcatgtt tgctcaagca ggtatgaatg atgtcagtgc ttccgcatca   420
gcaggagcat ccgcagcagc atccgcagga gcgccaggtt acagtcctgc accaagctac   480
agttcgggag ttatgcttc aagtgctgcc tcagcagccg ctgcagcagg acaaggagga   540
cctgggggat acggtccagc acctaaccaa ggagcttcat ctgccgctgc tgcagccgca   600
ggatcaggac aaggaccatc aggaccgtac ggtacatctt accagataag tacacaatat   660
actcaaacaa cgacttcaca gggacaagga tatgggtcaa gtagcgctgg agccgcagct   720
gcaggcgctg caggtgctgg acaaggggc tacggaggtc aaggtcaagg aggatatggt   780
caaggagccg gaggtgctgc cgcagcagcc gccgctgccg cagccgctgc cgccgcagcc   840
ggacaaggtg gacaaggtgg aggaggatat ggacaaggag gacaaggagg acaaggagga   900
caaggtcaag gaggatatgg acaaggtgca ggaagttctg cagccgccgc cgccgcagca   960
gcagcagccg ccgcagcagc aggacgaggt caaggaggat atggtccagg ttctggaggt  1020
```

<210> SEQ ID NO 17
<211> LENGTH: 422
<212> TYPE: PRT
<213> ORGANISM: Euprosthenops australis

<400> SEQUENCE: 17

```
Met Lys Ala Ser His Thr Thr Pro Trp Thr Asn Pro Gly Leu Ala Glu
1               5                   10                  15

Asn Phe Met Asn Ser Phe Met Gln Gly Leu Ser Ser Met Pro Gly Phe
            20                  25                  30

Thr Ala Ser Gln Leu Asp Asp Met Ser Thr Ile Ala Gln Ser Met Val
        35                  40                  45

Gln Ser Ile Gln Ser Leu Ala Ala Gln Gly Arg Thr Ser Pro Asn Lys
    50                  55                  60

Leu Gln Ala Leu Asn Met Ala Phe Ala Ser Ser Met Ala Glu Ile Ala
65                  70                  75                  80

Ala Ser Glu Glu Gly Gly Gly Ser Leu Ser Thr Lys Thr Ser Ser Ile
                85                  90                  95

Ala Ser Ala Met Ser Asn Ala Phe Leu Gln Thr Thr Gly Val Val Asn
            100                 105                 110

Gln Pro Phe Ile Asn Glu Ile Thr Gln Leu Val Ser Met Phe Ala Gln
        115                 120                 125

Ala Gly Met Asn Asp Val Ser Ala Ser Ala Ser Ala Gly Ala Ser Ala
    130                 135                 140

Ala Ala Ser Ala Gly Ala Ala Ser Gly Gln Gly Gly Tyr Gly Gly Leu
145                 150                 155                 160

Gly Gln Gly Gly Tyr Gly Gln Gly Ala Gly Ser Ser Ala Ala Ala Ala
                165                 170                 175
```

```
Ala Ala Ala Ala Ala Ala Ala Gly Gly Gln Gly Gly Gln Gly Gln
                180                 185                 190
Gly Gly Tyr Gly Gln Gly Ser Gly Gly Ser Ala Ala Ala Ala Ala
            195                 200                 205
Ala Ala Ala Ala Ala Ala Ala Gly Arg Gly Gln Gly Gly Tyr
210                 215                 220
Gly Gln Gly Ser Gly Gly Asn Ala Ala Ala Ala Ala Ala Ala Ala
225                 230                 235                 240
Ala Ala Ala Ala Ala Gly Gln Gly Gln Gly Tyr Gly Arg
                245                 250                 255
Gln Ser Gln Gly Ala Gly Ser Ala Ala Ala Ala Ala Ala Ala Ala
            260                 265                 270
Ala Ala Ala Ala Ala Gly Ser Gly Gln Gly Gly Tyr Gly Gln Gly
            275                 280                 285
Gln Gly Gly Tyr Gly Gln Ser Ser Ala Ser Ala Ser Ala Ala Ser
            290                 295                 300
Ala Ala Ser Thr Val Ala Asn Ser Val Ser Arg Leu Ser Ser Pro Ser
305                 310                 315                 320
Ala Val Ser Arg Val Ser Ser Ala Val Ser Ser Leu Val Ser Asn Gly
            325                 330                 335
Gln Val Asn Met Ala Ala Leu Pro Asn Ile Ile Ser Asn Ile Ser Ser
            340                 345                 350
Ser Val Ser Ala Ser Pro Gly Ala Ser Gly Cys Glu Val Ile Val
            355                 360                 365
Gln Ala Leu Leu Glu Val Ile Thr Ala Leu Val Gln Ile Val Ser Ser
            370                 375                 380
Ser Ser Val Gly Tyr Ile Asn Pro Ser Ala Val Asn Gln Ile Thr Asn
385                 390                 395                 400
Val Val Ala Asn Ala Met Ala Gln Val Met Gly Ala Ala Ala Leu Glu
                405                 410                 415
His His His His His His
            420

<210> SEQ ID NO 18
<211> LENGTH: 1266
<212> TYPE: DNA
<213> ORGANISM: Euprosthenops australis

<400> SEQUENCE: 18
atgaaagcat cacacactac accatggaca aacccaggac tcgcagaaaa cttcatgaac      60
agtttcatgc aaggcctgag ctcgatgcca ggtttcacgg caagccaatt ggatgatatg     120
tcaaccatcg cacaatccat ggtacagtca atacaatcct ggcggcacaa aggcaggaca     180
tcaccgaata agctgcaggc ccttaacatg gcttttgcat cttcgatggc agaaatcgcg     240
gcatccgaag aaggaggggg aagcctttcc accaaaacta gctctatagc cagtgcaatg     300
tccaacgcgt ttctgcaaac aactggagtg gtaaaccaac cgttcataaa tgaaataact     360
cagctcgtta gcatgtttgc tcaagcaggt atgaatgatg tcagtgcttc cgcatcagca     420
ggagcatccg cagcagcatc cgcaggagcg gctagcggtc aaggtggata tggtggacta     480
ggtcaaggag gatatggaca aggtgcagga agttctgcag ccgctgccgc cgccgcagca     540
gccgccgcag caggtggaca aggtggacaa ggtcaaggag gatatggaca aggttcagga     600
ggttctgcag ccgccgccgc cgccgcagca gcagcagcag ctgcagcagc tggacgaggt     660
caaggaggat atggtcaagg ttctggaggt aatgctgctg ccgcagccgc tgccgccgcc     720
```

-continued

| | |
|---|---:|
| gccgccgctg cagcagccgg acagggaggt caaggtggat atggtagaca aagccaaggt | 780 |
| gctggttccg ctgctgctgc tgctgctgct gctgccgctg ctgctgctgc aggatctgga | 840 |
| caaggtggat acgtggaca aggtcaagga ggttatggtc agagtagtgc ttctgcttca | 900 |
| gctgctgcgt cagctgctag tactgtagct aattcggtga gtcgcctctc atcgccttcc | 960 |
| gcagtatctc gagtttcttc agcagtttct agcttggttt caaatggtca agtgaatatg | 1020 |
| gcagcgttac ctaatatcat ttccaacatt tcttcttctg tcagtgcatc tgctcctggt | 1080 |
| gcttctggat gtgaggtcat agtgcaagct ctactcgaag tcatcactgc tcttgttcaa | 1140 |
| atcgttagtt cttctagtgt tggatatatt aatccatctg ctgtgaacca aattactaat | 1200 |
| gttgttgcta atgccatggc tcaagtaatg ggcgcggccg cactcgagca ccaccaccac | 1260 |
| caccac | 1266 |

<210> SEQ ID NO 19
<211> LENGTH: 491
<212> TYPE: PRT
<213> ORGANISM: Euprosthenops australis

<400> SEQUENCE: 19

```
Met Ala Ser Met Thr Gly Gly Gln Gln Met Gly Arg Gly Ser Val Asp
1               5                   10                  15

Asn Lys Phe Asn Lys Glu Arg Arg Ala Arg Arg Glu Ile Arg His
            20                  25                  30

Leu Pro Asn Leu Asn Arg Glu Gln Arg Arg Ala Phe Ile Arg Ser Leu
        35                  40                  45

Arg Asp Asp Pro Ser Gln Ser Ala Asn Leu Leu Ala Glu Ala Lys Lys
    50                  55                  60

Leu Asn Asp Ala Gln Ala Pro Lys Pro Asn Leu Glu Ala Leu Phe Gln
65                  70                  75                  80

Gly Pro Asn Ser His Thr Thr Pro Trp Thr Asn Pro Gly Leu Ala Glu
                85                  90                  95

Asn Phe Met Asn Ser Phe Met Gln Gly Leu Ser Ser Met Pro Gly Phe
            100                 105                 110

Thr Ala Ser Gln Leu Asp Asp Met Ser Thr Ile Ala Gln Ser Met Val
        115                 120                 125

Gln Ser Ile Gln Ser Leu Ala Ala Gln Gly Arg Thr Ser Pro Asn Lys
    130                 135                 140

Leu Gln Ala Leu Asn Met Ala Phe Ala Ser Ser Met Ala Glu Ile Ala
145                 150                 155                 160

Ala Ser Glu Glu Gly Gly Ser Leu Ser Thr Lys Thr Ser Ser Ile
                165                 170                 175

Ala Ser Ala Met Ser Asn Ala Phe Leu Gln Thr Thr Gly Val Val Asn
            180                 185                 190

Gln Pro Phe Ile Asn Glu Ile Thr Gln Leu Val Ser Met Phe Ala Gln
        195                 200                 205

Ala Gly Met Asn Asp Val Ser Ala Ser Ala Ser Ala Gly Ala Ser Ala
    210                 215                 220

Ala Ala Ser Ala Gly Ala Ala Ser Gly Gln Gly Gly Tyr Gly Gly Leu
225                 230                 235                 240

Gly Gln Gly Gly Tyr Gly Gln Gly Ala Gly Ser Ser Ala Ala Ala
                245                 250                 255

Ala Ala Ala Ala Ala Ala Ala Gly Gly Gln Gly Gly Gln
            260                 265                 270

Gly Gly Tyr Gly Gln Gly Ser Gly Gly Ser Ala Ala Ala Ala Ala
```

```
                        275                 280                 285
Ala Ala Ala Ala Ala Ala Ala Gly Arg Gly Gln Gly Gly Tyr
290                 295                 300

Gly Gln Gly Ser Gly Gly Asn Ala Ala Ala Ala Ala Ala Ala
305                 310                 315                 320

Ala Ala Ala Ala Ala Ala Gly Gln Gly Gln Gly Tyr Gly Arg
                325                 330                 335

Gln Ser Gln Gly Ala Gly Ser Ala Ala Ala Ala Ala Ala Ala
                340                 345                 350

Ala Ala Ala Ala Ala Gly Ser Gly Gln Gly Gly Tyr Gly Gln Gly
        355                 360                 365

Gln Gly Gly Tyr Gly Gln Ser Ser Ala Ser Ala Ala Ala Ser
370                 375                 380

Ala Ala Ser Thr Val Ala Asn Ser Val Ser Arg Leu Ser Ser Pro Ser
385                 390                 395                 400

Ala Val Ser Arg Val Ser Ser Ala Val Ser Ser Leu Val Ser Asn Gly
                405                 410                 415

Gln Val Asn Met Ala Ala Leu Pro Asn Ile Ile Ser Asn Ile Ser Ser
                420                 425                 430

Ser Val Ser Ala Ser Ala Pro Gly Ala Ser Gly Cys Glu Val Ile Val
        435                 440                 445

Gln Ala Leu Leu Glu Val Ile Thr Ala Leu Val Gln Ile Val Ser Ser
450                 455                 460

Ser Ser Val Gly Tyr Ile Asn Pro Ser Ala Val Asn Gln Ile Thr Asn
465                 470                 475                 480

Val Val Ala Asn Ala Met Ala Gln Val Met Gly
                485                 490

<210> SEQ ID NO 20
<211> LENGTH: 411
<212> TYPE: PRT
<213> ORGANISM: Euprosthenops australis

<400> SEQUENCE: 20

Gly Pro Asn Ser His Thr Thr Pro Trp Thr Asn Pro Gly Leu Ala Glu
1               5                   10                  15

Asn Phe Met Asn Ser Phe Met Gln Gly Leu Ser Ser Met Pro Gly Phe
                20                  25                  30

Thr Ala Ser Gln Leu Asp Asp Met Ser Thr Ile Ala Gln Ser Met Val
        35                  40                  45

Gln Ser Ile Gln Ser Leu Ala Ala Gln Gly Arg Thr Ser Pro Asn Lys
50                  55                  60

Leu Gln Ala Leu Asn Met Ala Phe Ala Ser Ser Met Ala Glu Ile Ala
65                  70                  75                  80

Ala Ser Glu Glu Gly Gly Gly Ser Leu Ser Thr Lys Thr Ser Ser Ile
                85                  90                  95

Ala Ser Ala Met Ser Asn Ala Phe Leu Gln Thr Thr Gly Val Val Asn
            100                 105                 110

Gln Pro Phe Ile Asn Glu Ile Thr Gln Leu Val Ser Met Phe Ala Gln
        115                 120                 125

Ala Gly Met Asn Asp Val Ser Ala Ser Ala Ser Gly Ala Ser Ala
    130                 135                 140

Ala Ala Ser Ala Gly Ala Ala Ser Gly Gln Gly Gly Tyr Gly Gly Leu
145                 150                 155                 160

Gly Gln Gly Gly Tyr Gly Gln Gly Ala Gly Ser Ser Ala Ala Ala Ala
```

```
                            165                 170                 175
Ala Ala Ala Ala Ala Ala Ala Gly Gly Gln Gly Gly Gln Gly Gln
                180                 185                 190

Gly Gly Tyr Gly Gln Gly Ser Gly Ser Ala Ala Ala Ala Ala
        195                 200                 205

Ala Ala Ala Ala Ala Ala Ala Gly Arg Gly Gln Gly Gly Tyr
    210                 215                 220

Gly Gln Gly Ser Gly Gly Asn Ala Ala Ala Ala Ala Ala Ala
225                 230                 235                 240

Ala Ala Ala Ala Ala Gly Gln Gly Gly Gln Gly Gly Tyr Gly Arg
                245                 250                 255

Gln Ser Gln Gly Ala Gly Ser Ala Ala Ala Ala Ala Ala Ala
        260                 265                 270

Ala Ala Ala Ala Gly Ser Gly Gln Gly Gly Tyr Gly Gln Gly
    275                 280                 285

Gln Gly Gly Tyr Gly Gln Ser Ser Ala Ser Ala Ser Ala Ala Ser
                290                 295                 300

Ala Ala Ser Thr Val Ala Asn Ser Val Ser Arg Leu Ser Ser Pro Ser
305                 310                 315                 320

Ala Val Ser Arg Val Ser Ser Ala Val Ser Ser Leu Val Ser Asn Gly
                325                 330                 335

Gln Val Asn Met Ala Ala Leu Pro Asn Ile Ile Ser Asn Ile Ser Ser
                340                 345                 350

Ser Val Ser Ala Ser Ala Pro Gly Ala Ser Gly Cys Glu Val Ile Val
                355                 360                 365

Gln Ala Leu Leu Glu Val Ile Thr Ala Leu Val Gln Ile Val Ser Ser
    370                 375                 380

Ser Ser Val Gly Tyr Ile Asn Pro Ser Ala Val Asn Gln Ile Thr Asn
385                 390                 395                 400

Val Val Ala Asn Ala Met Ala Gln Val Met Gly
                405                 410

<210> SEQ ID NO 21
<211> LENGTH: 551
<212> TYPE: PRT
<213> ORGANISM: Euprosthenops australis

<400> SEQUENCE: 21

Met Gly His His His His His His Met Ala Ser Ser Asp Lys Ile Ile
1               5                   10                  15

His Leu Thr Asp Asp Ser Phe Asp Thr Asp Val Leu Lys Ala Asp Gly
            20                  25                  30

Ala Ile Leu Val Asp Phe Trp Ala Glu Trp Cys Gly Pro Cys Lys Met
        35                  40                  45

Ile Ala Pro Ile Leu Asp Glu Ile Ala Asp Glu Tyr Gln Gly Lys Leu
    50                  55                  60

Thr Val Ala Lys Leu Asn Ile Asp Gln Asn Pro Gly Thr Ala Pro Lys
65                  70                  75                  80

Tyr Gly Ile Arg Gly Ile Pro Thr Leu Leu Leu Phe Lys Asn Gly Glu
                85                  90                  95

Val Ala Ala Thr Lys Val Gly Ala Leu Ser Lys Gly Gln Leu Lys Glu
            100                 105                 110

Phe Leu Asp Ala Asn Leu Ala Gly Ser Gly Ser Gly His Met His His
        115                 120                 125

His His His His Ser Ser Gly Leu Val Pro Arg Gly Ser Gly Asn Ser
```

```
            130                 135                 140
His Thr Thr Pro Trp Thr Asn Pro Gly Leu Ala Glu Asn Phe Met Asn
145                 150                 155                 160

Ser Phe Met Gln Gly Leu Ser Ser Met Pro Gly Phe Thr Ala Ser Gln
                165                 170                 175

Leu Asp Asp Met Ser Thr Ile Ala Gln Ser Met Val Gln Ser Ile Gln
            180                 185                 190

Ser Leu Ala Ala Gln Gly Arg Thr Ser Pro Asn Lys Leu Gln Ala Leu
                195                 200                 205

Asn Met Ala Phe Ala Ser Ser Met Ala Glu Ile Ala Ala Ser Glu Glu
        210                 215                 220

Gly Gly Gly Ser Leu Ser Thr Lys Thr Ser Ser Ile Ala Ser Ala Met
225                 230                 235                 240

Ser Asn Ala Phe Leu Gln Thr Thr Gly Val Val Asn Gln Pro Phe Ile
                245                 250                 255

Asn Glu Ile Thr Gln Leu Val Ser Met Phe Ala Gln Ala Gly Met Asn
                260                 265                 270

Asp Val Ser Ala Ser Ala Ser Ala Gly Ala Ser Ala Ala Ala Ser Ala
            275                 280                 285

Gly Ala Ala Ser Gly Gln Gly Gly Tyr Gly Gly Leu Gly Gln Gly Gly
        290                 295                 300

Tyr Gly Gln Gly Ala Gly Ser Ser Ala Ala Ala Ala Ala Ala Ala Ala
305                 310                 315                 320

Ala Ala Ala Ala Gly Gly Gln Gly Gly Gln Gly Gln Gly Gly Tyr Gly
                325                 330                 335

Gln Gly Ser Gly Gly Ser Ala Ala Ala Ala Ala Ala Ala Ala Ala Ala
            340                 345                 350

Ala Ala Ala Ala Ala Gly Arg Gly Gln Gly Gly Tyr Gly Gln Gly Ser
        355                 360                 365

Gly Gly Asn Ala Ala Ala Ala Ala Ala Ala Ala Ala Ala Ala Ala Ala
370                 375                 380

Ala Ala Gly Gln Gly Gly Gln Gly Gly Tyr Gly Arg Gln Ser Gln Gly
385                 390                 395                 400

Ala Gly Ser Ala Ala Ala Ala Ala Ala Ala Ala Ala Ala Ala Ala Ala
                405                 410                 415

Ala Gly Ser Gly Gln Gly Gly Tyr Gly Gly Gln Gly Gln Gly Gly Tyr
                420                 425                 430

Gly Gln Ser Ser Ala Ser Ala Ser Ala Ala Ser Ala Ala Ser Thr
            435                 440                 445

Val Ala Asn Ser Val Ser Arg Leu Ser Ser Pro Ser Ala Val Ser Arg
450                 455                 460

Val Ser Ser Ala Val Ser Ser Leu Val Ser Asn Gly Gln Val Asn Met
465                 470                 475                 480

Ala Ala Leu Pro Asn Ile Ile Ser Asn Ile Ser Ser Val Ser Ala
                485                 490                 495

Ser Ala Pro Gly Ala Ser Gly Cys Glu Val Ile Val Gln Ala Leu Leu
            500                 505                 510

Glu Val Ile Thr Ala Leu Val Gln Ile Val Ser Ser Ser Val Gly
            515                 520                 525

Tyr Ile Asn Pro Ser Ala Val Asn Gln Ile Thr Asn Val Val Ala Asn
            530                 535                 540

Ala Met Ala Gln Val Met Gly
545                 550
```

```
<210> SEQ ID NO 22
<211> LENGTH: 412
<212> TYPE: PRT
<213> ORGANISM: Euprosthenops australis

<400> SEQUENCE: 22

Gly Ser Gly Asn Ser His Thr Thr Pro Trp Thr Asn Pro Gly Leu Ala
 1               5                  10                  15

Glu Asn Phe Met Asn Ser Phe Met Gln Gly Leu Ser Ser Met Pro Gly
            20                  25                  30

Phe Thr Ala Ser Gln Leu Asp Asp Met Ser Thr Ile Ala Gln Ser Met
        35                  40                  45

Val Gln Ser Ile Gln Ser Leu Ala Ala Gln Gly Arg Thr Ser Pro Asn
    50                  55                  60

Lys Leu Gln Ala Leu Asn Met Ala Phe Ala Ser Ser Met Ala Glu Ile
 65                  70                  75                  80

Ala Ala Ser Glu Glu Gly Gly Gly Ser Leu Ser Thr Lys Thr Ser Ser
                85                  90                  95

Ile Ala Ser Ala Met Ser Asn Ala Phe Leu Gln Thr Thr Gly Val Val
            100                 105                 110

Asn Gln Pro Phe Ile Asn Glu Ile Thr Gln Leu Val Ser Met Phe Ala
        115                 120                 125

Gln Ala Gly Met Asn Asp Val Ser Ala Ser Ala Ser Ala Gly Ala Ser
    130                 135                 140

Ala Ala Ala Ser Ala Gly Ala Ala Ser Gly Gln Gly Gly Tyr Gly Gly
145                 150                 155                 160

Leu Gly Gln Gly Gly Tyr Gly Gln Gly Ala Gly Ser Ser Ala Ala Ala
                165                 170                 175

Ala Ala Ala Ala Ala Ala Ala Ala Gly Gly Gln Gly Gly Gln Gly Gly
            180                 185                 190

Gln Gly Gly Tyr Gly Gln Gly Ser Gly Gly Ser Ala Ala Ala Ala Ala
        195                 200                 205

Ala Ala Ala Ala Ala Ala Ala Ala Ala Gly Arg Gly Gln Gly Gly
    210                 215                 220

Tyr Gly Gln Gly Ser Gly Gly Asn Ala Ala Ala Ala Ala Ala Ala Ala
225                 230                 235                 240

Ala Ala Ala Ala Ala Ala Gly Gln Gly Gly Gln Gly Gly Tyr Gly
                245                 250                 255

Arg Gln Ser Gln Gly Ala Gly Ser Ala Ala Ala Ala Ala Ala Ala Ala
            260                 265                 270

Ala Ala Ala Ala Ala Ala Gly Ser Gly Gln Gly Gly Tyr Gly Gly Gln
        275                 280                 285

Gly Gln Gly Gly Tyr Gly Gln Ser Ala Ser Ala Ser Ala Ala Ala
    290                 295                 300

Ser Ala Ala Ser Thr Val Ala Asn Ser Val Ser Arg Leu Ser Ser Pro
305                 310                 315                 320

Ser Ala Val Ser Arg Val Ser Ser Ala Val Ser Ser Leu Val Ser Asn
                325                 330                 335

Gly Gln Val Asn Met Ala Ala Leu Pro Asn Ile Ile Ser Asn Ile Ser
            340                 345                 350

Ser Ser Val Ser Ala Ser Ala Pro Gly Ala Ser Gly Cys Glu Val Ile
        355                 360                 365

Val Gln Ala Leu Leu Glu Val Ile Thr Ala Leu Val Gln Ile Val Ser
    370                 375                 380
```

-continued

Ser Ser Ser Val Gly Tyr Ile Asn Pro Ser Ala Val Asn Gln Ile Thr
385                 390                 395                 400

Asn Val Val Ala Asn Ala Met Ala Gln Val Met Gly
                405                 410

<210> SEQ ID NO 23
<211> LENGTH: 534
<212> TYPE: PRT
<213> ORGANISM: Euprosthenops australis

<400> SEQUENCE: 23

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
                20                  25                  30

Ser Ser Met Pro Gly Phe Thr Ala Ser Gln Leu Asp Asp Met Ser Thr
            35                  40                  45

Ile Ala Gln Ser Met Val Gln Ser Ile Gln Ser Leu Ala Ala Gln Gly
        50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Ser Leu Ser
                85                  90                  95

Thr Lys Thr Ser Ser Ile Ala Ser Ala Met Ser Asn Ala Phe Leu Gln
                100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Gly Gly Thr Pro
130                 135                 140

Trp Thr Asn Pro Gly Leu Ala Glu Asn Phe Met Asn Ser Phe Met Gln
145                 150                 155                 160

Gly Leu Ser Ser Met Pro Gly Phe Thr Ala Ser Gln Leu Asp Asp Met
                165                 170                 175

Ser Thr Ile Ala Gln Ser Met Val Gln Ser Ile Gln Ser Leu Ala Ala
            180                 185                 190

Gln Gly Arg Thr Ser Pro Asn Lys Leu Gln Ala Leu Asn Met Ala Phe
        195                 200                 205

Ala Ser Ser Met Ala Glu Ile Ala Ala Ser Glu Glu Gly Gly Ser
            210                 215                 220

Leu Ser Thr Lys Thr Ser Ser Ile Ala Ser Ala Met Ser Asn Ala Phe
225                 230                 235                 240

Leu Gln Thr Thr Gly Val Val Asn Gln Pro Phe Ile Asn Glu Ile Thr
                245                 250                 255

Gln Leu Val Ser Met Phe Ala Gln Ala Gly Met Asn Asp Val Ser Ala
            260                 265                 270

Gly Asn Ser Gly Gln Gly Gly Tyr Gly Gly Leu Gly Gln Gly Gly Tyr
        275                 280                 285

Gly Gln Gly Ala Gly Ser Ser Ala Ala Ala Ala Ala Ala Ala Ala
            290                 295                 300

Ala Ala Ala Gly Gly Gln Gly Gly Gln Gly Gly Tyr Gly Gln
305                 310                 315                 320

Gly Ser Gly Gly Ser Ala Ala Ala Ala Ala Ala Ala Ala Ala
            325                 330                 335

Ala Ala Ala Gly Arg Gly Gly Gly Tyr Gly Gly Ser Gly
        340                 345                 350

```
Gly Asn Ala Ala Ala Ala Ala Ala Ala Ala Ala Ala Ala Ala
        355                 360                 365

Ala Gly Gln Gly Gly Gln Gly Gly Tyr Gly Arg Gln Ser Gln Gly Ala
    370                 375                 380

Gly Ser Ala Ala Ala Ala Ala Ala Ala Ala Ala Ala Ala Ala Ala Ala
385                 390                 395                 400

Gly Ser Gly Gln Gly Gly Tyr Gly Gly Gln Gly Gln Gly Gly Tyr Gly
                405                 410                 415

Gln Ser Ser Ala Ser Ala Ser Ala Ala Ala Ser Ala Ala Ser Thr Val
            420                 425                 430

Ala Asn Ser Val Ser Arg Leu Ser Ser Pro Ser Ala Val Ser Arg Val
        435                 440                 445

Ser Ser Ala Val Ser Ser Leu Val Ser Asn Gly Gln Val Asn Met Ala
    450                 455                 460

Ala Leu Pro Asn Ile Ile Ser Asn Ile Ser Ser Val Ser Ala Ser
465                 470                 475                 480

Ala Pro Gly Ala Ser Gly Cys Glu Val Ile Val Gln Ala Leu Leu Glu
                485                 490                 495

Val Ile Thr Ala Leu Val Gln Ile Val Ser Ser Ser Ser Val Gly Tyr
            500                 505                 510

Ile Asn Pro Ser Ala Val Asn Gln Ile Thr Asn Val Val Ala Asn Ala
        515                 520                 525

Met Ala Gln Val Met Gly
    530

<210> SEQ ID NO 24
<211> LENGTH: 1602
<212> TYPE: DNA
<213> ORGANISM: Euprosthenops australis

<400> SEQUENCE: 24
atgggccatc atcatcatca tcatatgagc cataccaccc cgtggaccaa cccgggcctg    60
gcggaaaact ttatgaacag ctttatgcag ggcctgagca gcatgccggg ctttaccgcg    120
agccagctgg atgatatgag caccattgcg cagagcatgg tgcagagcat tcagagcctg    180
gcggcgcagg ccgtaccag cccgaacaaa ctgcaggcgc tgaacatggc gtttgcgagc    240
agcatggcgg aaattgcggc gagcgaagaa ggcggcggca gcctgagcac caaaaccagc    300
agcattgcga gcgcgatgag caacgcgttt ctgcagacca ccggcgtggt gaaccagccg    360
tttattaacg aaattaccca gctggtgagc atgtttgcgc aggccggtat gaatgacggc    420
ggcggcaccc cgtggaccaa cccgggcctg gcggaaaact ttatgaacag ctttatgcag    480
ggcctgagca gcatgccggg ctttaccgcg agccagctgg atgatatgag caccattgcg    540
cagagcatgg tgcagagcat tcagagcctg gcggcgcagg ccgtaccag cccgaacaaa    600 ctgcaggcgc tgaacatggc gtttgcgagc agcatggcgg aaattgcggc gagcgaagaa    660
ggcggcggca gcctgagcac caaaaccagc agcattgcga gcgcgatgag caacgcgttt    720
ctgcagacca ccggcgtggt gaaccagccg tttattaacg aaattaccca gctggtgagc    780
atgtttgcgc aggcgggcat gaacgatgtg agcgcgggga attcaggtca aggtggatat    840
ggtggactag gtcaaggagg atatggacaa ggtgcaggaa gttctgcagc cgctgccgcc    900
gccgcagcag ccgccgcagc aggtggacaa ggtggacaag gtcaaggagg atatggacaa    960
ggttcaggag gttctgcagc cgccgccgcc gccgcagcag cagcagcagc tgcagcagct   1020
ggacgaggtc aaggaggata tggtcaaggt tctggaggta atgctgctgc cgcagccgct   1080
```

-continued

```
gccgccgccg ccgccgctgc agcagccgga cagggaggtc aaggtggata tggtagacaa    1140
agccaaggtg ctggttccgc tgctgctgct gctgctgctg ctgccgctgc tgctgctgca    1200
ggatctggac aaggtggata cggtggacaa ggtcaaggag gttatggtca gagtagtgct    1260
tctgcttcag ctgctgcgtc agctgctagt actgtagcta attcggtgag tcgcctctca    1320
tcgccttccg cagtatctcg agtttcttca gcagtttcta gcttggtttc aaatggtcaa    1380
gtgaatatgg cagcgttacc taatatcatt ccaacatttt cttcttctgt cagtgcatct    1440
gctcctggtg cttctggatg tgaggtcata gtgcaagctc tactcgaagt catcactgct    1500
cttgttcaaa tcgttagttc ttctagtgtt ggatatatta atccatctgc tgtgaaccaa    1560
attactaatg ttgttgctaa tgccatggct caagtaatgg gc                       1602
```

<210> SEQ ID NO 25
<211> LENGTH: 514
<212> TYPE: PRT
<213> ORGANISM: Euprosthenops australis

<400> SEQUENCE: 25

```
Gly Ser Gly Asn Ser His Thr Thr Pro Trp Thr Asn Pro Gly Leu Ala
1               5                   10                  15

Glu Asn Phe Met Asn Ser Phe Met Gln Gly Leu Ser Ser Met Pro Gly
            20                  25                  30

Phe Thr Ala Ser Gln Leu Asp Asp Met Ser Thr Ile Ala Gln Ser Met
        35                  40                  45

Val Gln Ser Ile Gln Ser Leu Ala Ala Gln Gly Arg Thr Ser Pro Asn
    50                  55                  60

Lys Leu Gln Ala Leu Asn Met Ala Phe Ala Ser Ser Met Ala Glu Ile
65                  70                  75                  80

Ala Ala Ser Glu Glu Gly Gly Gly Ser Leu Ser Thr Lys Thr Ser Ser
                85                  90                  95

Ile Ala Ser Ala Met Ser Asn Ala Phe Leu Gln Thr Thr Gly Val Val
            100                 105                 110

Asn Gln Pro Phe Ile Asn Glu Ile Thr Gln Leu Val Ser Met Phe Ala
        115                 120                 125

Gln Ala Gly Met Asn Asp Val Ser Ala Gly Tyr Gly Gln Gly Ala Gly
    130                 135                 140

Ser Ser Ala Ala Ala Ala Ala Ala Ala Ala Ala Ala Ala Ala Ala Ala
145                 150                 155                 160

Gly Arg Gly Gln Gly Gly Tyr Gly Gln Gly Ser Gly Gly Asn Ala Ala
                165                 170                 175

Ala Ala Ala Ala Ala Ala Ala Ala Ala Ser Gly Gln Gly Ser Gln
            180                 185                 190

Gly Gly Gln Gly Gly Gln Gly Gln Gly Gly Tyr Gly Gln Gly Ala Gly
    195                 200                 205

Ser Ser Ala Ala Ala Ala Ala Ala Ala Ala Ala Ala Ala Ala Ser
        210                 215                 220

Gly Arg Gly Gln Gly Gly Tyr Gly Gln Gly Ala Gly Gly Asn Ala Ala
225                 230                 235                 240

Ala Ala Ala Ala Ala Ala Ala Ala Ala Ala Gly Gln Gly Gly
                245                 250                 255

Gln Gly Gly Tyr Gly Gly Leu Gly Gln Gly Gly Tyr Gly Gln Gly Ala
            260                 265                 270

Gly Ser Ser Ala Ala Ala Ala Ala Ala Ala Ala Ala Ala Ala Gly
        275                 280                 285
```

```
Gly Gln Gly Gly Gln Gly Gly Tyr Gly Gln Gly Ser Gly Gly
        290                 295                 300

Ser Ala Ala Ala Ala Ala Ala Ala Ala Ala Ala Ala Ala Ala
305                 310                 315                 320

Gly Arg Gly Gln Gly Gly Tyr Gly Gln Gly Ser Gly Asn Ala Ala
                    325                 330                 335

Ala Ala Ala Ala Ala Ala Ala Ala Ala Ala Ala Ala Gly Gln Gly
                340                 345                 350

Gly Gln Gly Gly Tyr Gly Arg Gln Ser Gln Gly Ala Gly Ser Ala Ala
        355                 360                 365

Ala Ala Ala Ala Ala Ala Ala Ala Ala Ala Gly Ser Gly Gln
        370                 375                 380

Gly Gly Tyr Gly Gly Gln Gly Gln Gly Gly Tyr Gly Gln Ser Ser Ala
385                 390                 395                 400

Ser Ala Ser Ala Ala Ser Ala Ala Ser Thr Val Ala Asn Ser Val
                405                 410                 415

Ser Arg Leu Ser Ser Pro Ser Ala Val Ser Arg Val Ser Ala Val
                420                 425                 430

Ser Ser Leu Val Ser Asn Gly Gln Val Asn Met Ala Ala Leu Pro Asn
        435                 440                 445

Ile Ile Ser Asn Ile Ser Ser Val Ser Ala Ser Ala Pro Gly Ala
450                 455                 460

Ser Gly Cys Glu Val Ile Val Gln Ala Leu Leu Glu Val Ile Thr Ala
465                 470                 475                 480

Leu Val Gln Ile Val Ser Ser Ser Val Gly Tyr Ile Asn Pro Ser
                485                 490                 495

Ala Val Asn Gln Ile Thr Asn Val Val Ala Asn Ala Met Ala Gln Val
                500                 505                 510

Met Gly

<210> SEQ ID NO 26
<211> LENGTH: 176
<212> TYPE: PRT
<213> ORGANISM: Artificial Sequence
<220> FEATURE:
<223> OTHER INFORMATION: Fusion protein

<400> SEQUENCE: 26

Met Gly His His His His His Met Ser His Thr Thr Pro Trp Thr
1               5                   10                  15

Asn Pro Gly Leu Ala Glu Asn Phe Met Asn Ser Phe Met Gln Gly Leu
                20                  25                  30

Ser Ser Met Pro Gly Phe Thr Ala Ser Gln Leu Asp Asp Met Ser Thr
            35                  40                  45

Ile Ala Gln Ser Met Val Gln Ser Ile Gln Ser Leu Ala Ala Gln Gly
    50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
        115                 120                 125

Val Ser Met Phe Ala Gln Ala Gly Met Asn Asp Val Ser Ala Met Ile
    130                 135                 140
```

```
Pro Ser Ser Pro Val His Leu Lys Arg Leu Lys Leu Leu Leu Leu
145                 150                 155                 160

Leu Leu Leu Ile Leu Leu Leu Ile Leu Gly Ala Leu Leu Gly Leu
                165                 170                 175

<210> SEQ ID NO 27
<211> LENGTH: 528
<212> TYPE: DNA
<213> ORGANISM: Artificial Sequence
<220> FEATURE:
<223> OTHER INFORMATION: Nucleotide sequence encoding a fusion protein

<400> SEQUENCE: 27
atgggccatc atcatcatca tcatatgagc cataccaccc cgtggaccaa cccgggcctg      60 gcggaaaaact ttatgaacag ctttatgcag ggcctgagca gcatgccggg ctttaccgcg    120
agccagctgg atgatatgag caccattgcg cagagcatgg tgcagagcat tcagagcctg    180
gcggcgcagg gccgtaccag cccgaacaaa ctgcaggcgc tgaacatggc gtttgcgagc    240
agcatggcgg aaattgcggc gagcgaagaa ggcggcggca gcctgagcac caaaaccagc    300
agcattgcga gcgcgatgag caacgcgttt ctgcagacca ccggcgtggt gaaccagccg    360
tttattaacg aaattaccca gctggtgagc atgtttgcgc aggcgggcat gaacgatgtg    420
agcgcgatga ttccgagcag cccggtgcat ctgaaacgcc tgaaactgct gctgctgctg    480
ctgctgctga ttctgctgct gattctgggc gcgctgctgc tgggcctg                 528

<210> SEQ ID NO 28
<211> LENGTH: 309
<212> TYPE: PRT
<213> ORGANISM: Artificial Sequence
<220> FEATURE:
<223> OTHER INFORMATION: Fusion protein

<400> SEQUENCE: 28

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
                20                  25                  30

Ser Ser Met Pro Gly Phe Thr Ala Ser Gln Leu Asp Asp Met Ser Thr
            35                  40                  45

Ile Ala Gln Ser Met Val Gln Ser Ile Gln Ser Leu Ala Ala Gln Gly
        50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
                100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Met Ile
        130                 135                 140

Pro Ser Ser Pro Val His Leu Lys Arg Leu Lys Leu Leu Leu Leu Leu
145                 150                 155                 160

Trp Thr Asn Pro Gly Leu Ala Glu Asn Phe Met Asn Ser Phe Met Gln
145                 150                 155                 160

Gly Leu Ser Ser Met Pro Gly Phe Thr Ala Ser Gln Leu Asp Asp Met
                165                 170                 175

Ser Thr Ile Ala Gln Ser Met Val Gln Ser Ile Gln Ser Leu Ala Ala
            180                 185                 190
```

-continued

Gln Gly Arg Thr Ser Pro Asn Lys Leu Gln Ala Leu Asn Met Ala Phe
         195                 200                 205

Ala Ser Ser Met Ala Glu Ile Ala Ala Ser Glu Gly Gly Gly Ser
    210                 215                 220

Leu Ser Thr Lys Thr Ser Ile Ala Ser Ala Met Ser Asn Ala Phe
225                 230                 235                 240

Leu Gln Thr Thr Gly Val Val Asn Gln Pro Phe Ile Asn Glu Ile Thr
                245                 250                 255

Gln Leu Val Ser Met Phe Ala Gln Ala Gly Met Asn Asp Val Ser Ala
            260                 265                 270

Gly Asn Ser Met Ile Pro Ser Ser Pro Val His Leu Lys Arg Leu Lys
        275                 280                 285

Leu Leu Leu Leu Leu Leu Leu Leu Ile Leu Leu Leu Ile Leu Gly Ala
        290                 295                 300

Leu Leu Leu Gly Leu
305

<210> SEQ ID NO 29
<211> LENGTH: 927
<212> TYPE: DNA
<213> ORGANISM: Artificial Sequence
<220> FEATURE:
<223> OTHER INFORMATION: Nucleotide sequence encoding a fusion protein

<400> SEQUENCE: 29
atgggccatc atcatcatca tcatatgagc cataccaccc cgtggaccaa cccgggcctg      60
gcggaaaact ttatgaacag ctttatgcag ggcctgagca gcatgccggg ctttaccgcg     120
agccagctgg atgatatgag caccattgcg cagagcatgg tgcagagcat tcagagcctg     180
gcggcgcagg gccgtaccag cccgaacaaa ctgcaggcgc tgaacatggc gtttgcgagc     240
agcatggcgg aaattgcggc gagcgaagaa ggcggcggca gcctgagcac caaaaccagc     300
agcattgcga gcgcgatgag caacgcgttt ctgcagacca ccggcgtggt gaaccagccg     360
tttattaacg aaattaccca gctggtgagc atgtttgcgc aggccggtat gaatgacggc     420
ggcggcaccc cgtggaccaa cccgggcctg gcggaaaact ttatgaacag ctttatgcag     480
ggcctgagca gcatgccggg ctttaccgcg agccagctgg atgatatgag caccattgcg     540
cagagcatgg tgcagagcat tcagagcctg gcggcgcagg gccgtaccag cccgaacaaa     600
ctgcaggcgc tgaacatggc gtttgcgagc agcatggcgg aaattgcggc gagcgaagaa     660
ggcggcggca gcctgagcac caaaaccagc agcattgcga gcgcgatgag caacgcgttt     720
ctgcagacca ccggcgtggt gaaccagccg tttattaacg aaattaccca gctggtgagc     780
atgtttgcgc aggcgggcat gaacgatgtg agcgcgggga attctatgat tccgagcagc     840
ccggtgcatc tgaaacgcct gaaactgctg ctgctgctgc tgctgctgat tctgctgctg     900
attctgggcg cgctgctgct gggcctg                                         927

<210> SEQ ID NO 30
<211> LENGTH: 158
<212> TYPE: PRT
<213> ORGANISM: Euprosthenops australis

<400> SEQUENCE: 30

Met Ser His Thr Thr Pro Trp Thr Asn Pro Gly Leu Ala Glu Asn Phe
1               5                   10                  15

Met Asn Ser Phe Met Gln Gly Leu Ser Ser Met Pro Gly Phe Thr Ala
            20                  25                  30

Ser Gln Leu Asp Asp Met Ser Thr Ile Ala Gln Ser Met Val Gln Ser
            35                  40                  45

Ile Gln Ser Leu Ala Ala Gln Gly Arg Thr Ser Pro Asn Lys Leu Gln
 50                  55                  60

Ala Leu Asn Met Ala Phe Ala Ser Ser Met Ala Glu Ile Ala Ala Ser
 65                  70                  75                  80

Glu Glu Gly Gly Gly Ser Leu Ser Thr Lys Thr Ser Ser Ile Ala Ser
                 85                  90                  95

Ala Met Ser Asn Ala Phe Leu Gln Thr Thr Gly Val Val Asn Gln Pro
                100                 105                 110

Phe Ile Asn Glu Ile Thr Gln Leu Val Ser Met Phe Ala Gln Ala Gly
                115                 120                 125

Met Asn Asp Val Ser Ala Ser Ala Ser Ala Gly Ala Ser Ala Ala Ala
            130                 135                 140

Ser Ala Gly Ala Ala Ala Leu Glu His His His His His His
145                 150                 155

<210> SEQ ID NO 31
<211> LENGTH: 646
<212> TYPE: PRT
<213> ORGANISM: Euprosthenops australis

<400> SEQUENCE: 31

His His His His His His Ser His Thr Thr Pro Trp Thr Asn Pro Gly
  1               5                  10                  15

Leu Ala Glu Asn Phe Met Asn Ser Phe Met Gln Gly Leu Ser Ser Met
                 20                  25                  30

Pro Gly Phe Thr Ala Ser Gln Leu Asp Asp Met Ser Thr Ile Ala Gln
            35                  40                  45

Ser Met Val Gln Ser Ile Gln Ser Leu Ala Ala Gln Gly Arg Thr Ser
 50                  55                  60

Pro Asn Lys Leu Gln Ala Leu Asn Met Ala Phe Ala Ser Ser Met Ala
 65                  70                  75                  80

Glu Ile Ala Ala Ser Glu Glu Gly Gly Gly Ser Leu Ser Thr Lys Thr
                 85                  90                  95

Ser Ser Ile Ala Ser Ala Met Ser Asn Ala Phe Leu Gln Thr Thr Gly
                100                 105                 110

Val Val Asn Gln Pro Phe Ile Asn Glu Ile Thr Gln Leu Val Ser Met
            115                 120                 125

Phe Ala Gln Ala Gly Met Asn Asp Gly Gly Thr Pro Trp Thr Asn
 130                 135                 140

Pro Gly Leu Ala Glu Asn Phe Met Asn Ser Phe Met Gln Gly Leu Ser
145                 150                 155                 160

Ser Met Pro Gly Phe Thr Ala Ser Gln Leu Asp Asp Met Ser Thr Ile
                165                 170                 175

Ala Gln Ser Met Val Gln Ser Ile Gln Ser Leu Ala Ala Gln Gly Arg
                180                 185                 190

Thr Ser Pro Asn Lys Leu Gln Ala Leu Asn Met Ala Phe Ala Ser Ser
            195                 200                 205

Met Ala Glu Ile Ala Ala Ser Glu Glu Gly Gly Gly Ser Leu Ser Thr
 210                 215                 220

Lys Thr Ser Ser Ile Ala Ser Ala Met Ser Asn Ala Phe Leu Gln Thr
225                 230                 235                 240

Thr Gly Val Val Asn Gln Pro Phe Ile Asn Glu Ile Thr Gln Leu Val
                245                 250                 255

Ser Met Phe Ala Gln Ala Gly Met Asn Asp Val Ser Ala Gly Tyr Gly
                260                 265                 270

Gln Gly Ala Gly Ser Ser Ala Ala Ala Ala Ala Ala Ala Ala Ala Ala
            275                 280                 285

Ala Ala Ala Ala Gly Arg Gly Gln Gly Gly Tyr Gly Gln Gly Ser Gly
        290                 295                 300

Gly Asn Ala Ala Ala Ala Ala Ala Ala Ala Ala Ala Ala Ala Ser Gly
305                 310                 315                 320

Gln Gly Ser Gln Gly Gln Gly Gly Gln Gln Gly Gly Tyr Gly
                325                 330                 335

Gln Gly Ala Gly Ser Ser Ala Ala Ala Ala Ala Ala Ala Ala Ala Ala
                340                 345                 350

Ala Ala Ala Ser Gly Arg Gly Gln Gly Gly Tyr Gly Gln Gly Ala Gly
            355                 360                 365

Gly Asn Ala Ala Ala Ala Ala Ala Ala Ala Ala Ala Ala Ala Ala Ala
        370                 375                 380

Gly Gln Gly Gly Gln Gly Gly Tyr Gly Gly Leu Gly Gln Gly Gly Tyr
385                 390                 395                 400

Gly Gln Gly Ala Gly Ser Ser Ala Ala Ala Ala Ala Ala Ala Ala Ala
                405                 410                 415

Ala Ala Ala Gly Gly Gln Gly Gly Gln Gly Gln Gly Tyr Gly Gln
            420                 425                 430

Gly Ser Gly Gly Ser Ala Ala Ala Ala Ala Ala Ala Ala Ala Ala
        435                 440                 445

Ala Ala Ala Gly Arg Gly Gln Gly Gly Tyr Gly Gln Gly Ser Gly
    450                 455                 460

Gly Asn Ala Ala Ala Ala Ala Ala Ala Ala Ala Ala Ala Ala Ala Ala
465                 470                 475                 480

Ala Gly Gln Gly Gly Gln Gly Gly Tyr Gly Arg Gln Ser Gln Gly Ala
                485                 490                 495

Gly Ser Ala Ala Ala Ala Ala Ala Ala Ala Ala Ala Ala Ala
            500                 505                 510

Gly Ser Gly Gln Gly Tyr Gly Gly Gln Gly Gln Gly Gly Tyr Gly
        515                 520                 525

Gln Ser Ser Ala Ser Ala Ser Ala Ala Ala Ser Ala Ala Ser Thr Val
    530                 535                 540

Ala Asn Ser Val Ser Arg Leu Ser Ser Pro Ser Ala Val Ser Arg Val
545                 550                 555                 560

Ser Ser Ala Val Ser Ser Leu Val Ser Asn Gly Gln Val Asn Met Ala
                565                 570                 575

Ala Leu Pro Asn Ile Ile Ser Asn Ile Ser Ser Val Ser Ala Ser
            580                 585                 590

Ala Pro Gly Ala Ser Gly Cys Glu Val Ile Val Gln Ala Leu Leu Glu
        595                 600                 605

Val Ile Thr Ala Leu Val Gln Ile Val Ser Ser Ser Val Gly Tyr
610                 615                 620

Ile Asn Pro Ser Ala Val Asn Gln Ile Thr Asn Val Val Ala Asn Ala
625                 630                 635                 640

Met Ala Gln Val Met Gly
                645

<210> SEQ ID NO 32
<211> LENGTH: 387
<212> TYPE: PRT

<213> ORGANISM: Artificial Sequence
<220> FEATURE:
<223> OTHER INFORMATION: Fusion protein

<400> SEQUENCE: 32

```
Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Asp Met Ser Thr
        35                  40                  45

Ile Ala Gln Ser Met Val Gln Ser Ile Gln Ser Leu Ala Ala Gln Gly
    50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Ser Leu Ser
                85                  90                  95

Thr Lys Thr Ser Ser Ile Ala Ser Ala Met Ser Asn Ala Phe Leu Gln
                100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Gly Gly Thr Pro
130                 135                 140

Trp Thr Asn Pro Gly Leu Ala Glu Asn Phe Met Asn Ser Phe Met Gln
145                 150                 155                 160

Gly Leu Ser Ser Met Pro Gly Phe Thr Ala Ser Gln Leu Asp Asp Met
                165                 170                 175

Ser Thr Ile Ala Gln Ser Met Val Gln Ser Ile Gln Ser Leu Ala Ala
            180                 185                 190

Gln Gly Arg Thr Ser Pro Asn Lys Leu Gln Ala Leu Asn Met Ala Phe
        195                 200                 205

Ala Ser Ser Met Ala Glu Ile Ala Ala Ser Glu Glu Gly Gly Ser
210                 215                 220

Leu Ser Thr Lys Thr Ser Ser Ile Ala Ser Ala Met Ser Asn Ala Phe
225                 230                 235                 240

Leu Gln Thr Thr Gly Val Val Asn Gln Pro Phe Ile Asn Glu Ile Thr
                245                 250                 255

Gln Leu Val Ser Met Phe Ala Gln Ala Gly Met Asn Asp Val Ser Ala
            260                 265                 270

Gly Asn Ser Glu His Leu Val Thr Thr Ala Thr Phe Ser Ile Gly Ser
        275                 280                 285

Thr Gly Leu Val Val Tyr Asp Tyr Gln Gln Leu Leu Ile Ala Tyr Lys
    290                 295                 300

Pro Ala Pro Gly Thr Cys Cys Tyr Ile Met Lys Ile Ala Pro Glu Ser
305                 310                 315                 320

Ile Pro Ser Leu Glu Ala Leu Thr Arg Lys Val His Asn Phe Gln Met
                325                 330                 335

Glu Cys Ser Leu Gln Ala Lys Pro Ala Val Pro Thr Ser Lys Leu Gly
            340                 345                 350

Gln Ala Glu Gly Arg Asp Ala Gly Ser Ala Pro Ser Gly Gly Asp Pro
        355                 360                 365

Ala Phe Leu Gly Met Ala Val Ser Thr Leu Cys Gly Glu Val Pro Leu
    370                 375                 380

Tyr Tyr Ile
385
```

<210> SEQ ID NO 33
<211> LENGTH: 131
<212> TYPE: PRT
<213> ORGANISM: Euprosthenops australis

<400> SEQUENCE: 33

```
Ser His Thr Thr Pro Trp Thr Asn Pro Gly Leu Ala Glu Asn Phe Met
1               5                   10                  15

Asn Ser Phe Met Gln Gly Leu Ser Ser Met Pro Gly Phe Thr Ala Ser
            20                  25                  30

Gln Leu Asp Asp Met Ser Thr Ile Ala Gln Ser Met Val Gln Ser Ile
        35                  40                  45

Gln Ser Leu Ala Ala Gln Gly Arg Thr Ser Pro Asn Lys Leu Gln Ala
    50                  55                  60

Leu Asn Met Ala Phe Ala Ser Ser Met Ala Glu Ile Ala Ala Ser Glu
65                  70                  75                  80

Glu Gly Gly Gly Ser Leu Ser Thr Lys Thr Ser Ser Ile Ala Ser Ala
                85                  90                  95

Met Ser Asn Ala Phe Leu Gln Thr Thr Gly Val Val Asn Gln Pro Phe
            100                 105                 110

Ile Asn Glu Ile Thr Gln Leu Val Ser Met Phe Ala Gln Ala Gly Met
        115                 120                 125

Asn Asp Val
        130
```

<210> SEQ ID NO 34
<211> LENGTH: 127
<212> TYPE: PRT
<213> ORGANISM: Latrodectus geometricus

<400> SEQUENCE: 34

```
Gln Ala Asn Thr Pro Trp Ser Ser Lys Gln Asn Ala Asp Ala Phe Ile
1               5                   10                  15

Ser Ala Phe Met Thr Ala Ala Ser Gln Ser Gly Ala Phe Ser Ser Asp
            20                  25                  30

Gln Ile Asp Asp Met Ser Val Ile Ser Asn Thr Leu Met Ala Ala Met
        35                  40                  45

Asp Asn Met Gly Gly Arg Ile Thr Pro Ser Lys Leu Gln Ala Leu Asp
    50                  55                  60

Met Ala Phe Ala Ser Ser Val Ala Glu Ile Ala Ala Val Glu Gly Gln
65                  70                  75                  80

Asn Ile Gly Val Thr Thr Asn Ala Ile Ser Asp Ala Leu Thr Ser Ala
                85                  90                  95

Phe Tyr Gln Thr Thr Gly Val Val Asn Asn Lys Phe Ile Ser Glu Ile
            100                 105                 110

Arg Ser Leu Ile Asn Met Phe Ala Gln Ala Ser Ala Asn Asp Val
        115                 120                 125
```

<210> SEQ ID NO 35
<211> LENGTH: 127
<212> TYPE: PRT
<213> ORGANISM: Latrodectus hesperus

<400> SEQUENCE: 35

```
Gln Ala Asn Thr Pro Trp Ser Ser Lys Ala Asn Ala Asp Ala Phe Ile
1               5                   10                  15

Asn Ser Phe Ile Ser Ala Ala Ser Asn Thr Gly Ser Phe Ser Gln Asp
```

-continued

```
                20                  25                  30
Gln Met Glu Asp Met Ser Leu Ile Gly Asn Thr Leu Met Ala Met
            35                  40                  45
Asp Asn Met Gly Gly Arg Ile Thr Pro Ser Lys Leu Gln Ala Leu Asp
        50                  55                  60
Met Ala Phe Ala Ser Ser Val Ala Glu Ile Ala Ala Ser Glu Gly Gly
65                  70                  75                  80
Asp Leu Gly Val Thr Thr Asn Ala Ile Ala Asp Ala Leu Thr Ser Ala
                85                  90                  95
Phe Tyr Gln Thr Thr Gly Val Val Asn Ser Arg Phe Ile Ser Glu Ile
            100                 105                 110
Arg Ser Leu Ile Gly Met Phe Ala Gln Ala Ser Ala Asn Asp Val
        115                 120                 125

<210> SEQ ID NO 36
<211> LENGTH: 130
<212> TYPE: PRT
<213> ORGANISM: Nephila clavipes

<400> SEQUENCE: 36

Gln Asn Thr Pro Trp Ser Ser Thr Glu Leu Ala Asp Ala Phe Ile Asn
1               5                   10                  15
Ala Phe Met Asn Glu Ala Gly Arg Thr Gly Ala Phe Thr Ala Asp Gln
                20                  25                  30
Leu Asp Asp Met Ser Thr Ile Gly Asp Thr Ile Lys Thr Ala Met Asp
            35                  40                  45
Lys Met Ala Arg Ser Asn Lys Ser Ser Lys Gly Lys Leu Gln Ala Leu
        50                  55                  60
Asn Met Ala Phe Ala Ser Ser Met Ala Glu Ile Ala Ala Val Glu Gln
65                  70                  75                  80
Gly Gly Leu Ser Val Asp Ala Lys Thr Asn Ala Ile Ala Asp Ser Leu
                85                  90                  95
Asn Ser Ala Phe Tyr Gln Thr Thr Gly Ala Ala Asn Pro Gln Phe Val
            100                 105                 110
Asn Glu Ile Arg Ser Leu Ile Asn Met Phe Ala Gln Ser Ser Ala Asn
        115                 120                 125
Glu Val
    130

<210> SEQ ID NO 37
<211> LENGTH: 131
<212> TYPE: PRT
<213> ORGANISM: Argiope trifasciata

<400> SEQUENCE: 37

Gln Gly Ala Thr Pro Trp Glu Asn Ser Gln Leu Ala Glu Ser Phe Ile
1               5                   10                  15
Ser Arg Phe Leu Arg Phe Ile Gly Gln Ser Gly Ala Phe Ser Pro Asn
                20                  25                  30
Gln Leu Asp Asp Met Ser Ile Gly Asp Thr Leu Lys Thr Ala Ile
            35                  40                  45
Glu Lys Met Ala Gln Ser Arg Lys Ser Ser Lys Ser Lys Leu Gln Ala
        50                  55                  60
Leu Asn Met Ala Phe Ala Ser Ser Met Ala Glu Ile Ala Val Ala Glu
65                  70                  75                  80
Gln Gly Gly Leu Ser Leu Glu Ala Lys Thr Asn Ala Ile Ala Ser Ala
                85                  90                  95
```

Leu Ser Ala Ala Phe Leu Glu Thr Thr Gly Tyr Val Asn Gln Gln Phe
            100                 105                 110

Val Asn Glu Ile Lys Thr Leu Ile Phe Met Ile Ala Gln Ala Ser Ser
        115                 120                 125

Asn Glu Ile
    130

<210> SEQ ID NO 38
<211> LENGTH: 124
<212> TYPE: PRT
<213> ORGANISM: Latrodectus geometricus

<400> SEQUENCE: 38

Leu Arg Trp Ser Ser Lys Asp Asn Ala Asp Arg Phe Ile Asn Ala Phe
1               5                   10                  15

Leu Gln Ala Ala Ser Asn Ser Gly Ala Phe Ser Ser Asp Gln Val Asp
            20                  25                  30

Asp Met Ser Val Ile Gly Asn Thr Leu Met Thr Ala Met Asp Asn Met
        35                  40                  45

Gly Gly Arg Ile Thr Pro Ser Lys Leu Gln Ala Leu Asp Met Ala Phe
50                  55                  60

Ala Ser Ser Val Ala Glu Ile Ala Val Ala Asp Gly Gln Asn Val Gly
65                  70                  75                  80

Gly Ala Thr Asn Ala Ile Ser Asn Ala Leu Arg Ser Ala Phe Tyr Gln
                85                  90                  95

Thr Thr Gly Val Val Asn Gln Phe Ile Ser Glu Ile Ser Asn Leu
            100                 105                 110

Ile Asn Met Phe Ala Gln Val Ser Ala Asn Glu Val
        115                 120

<210> SEQ ID NO 39
<211> LENGTH: 127
<212> TYPE: PRT
<213> ORGANISM: Latrodectus hesperus

<400> SEQUENCE: 39

Gln Ala Asn Thr Pro Trp Ser Ser Lys Glu Asn Ala Asp Ala Phe Ile
1               5                   10                  15

Gly Ala Phe Met Asn Ala Ala Ser Gln Ser Gly Ala Phe Ser Ser Asp
            20                  25                  30

Gln Ile Asp Asp Met Ser Val Ile Ser Asn Thr Leu Met Ala Ala Met
        35                  40                  45

Asp Asn Met Gly Gly Arg Ile Thr Gln Ser Lys Leu Gln Ala Leu Asp
50                  55                  60

Met Ala Phe Ala Ser Ser Val Ala Glu Ile Ala Val Ala Asp Gly Gln
65                  70                  75                  80

Asn Val Gly Ala Ala Thr Asn Ala Ile Ser Asp Ala Leu Arg Ser Ala
                85                  90                  95

Phe Tyr Gln Thr Thr Gly Val Val Asn Asn Gln Phe Ile Thr Gly Ile
            100                 105                 110

Ser Ser Leu Ile Gly Met Phe Ala Gln Val Ser Gly Asn Glu Val
        115                 120                 125

<210> SEQ ID NO 40
<211> LENGTH: 131
<212> TYPE: PRT
<213> ORGANISM: Nephila inaurata madagascariensis

```
<400> SEQUENCE: 40

Gln Ala Asn Thr Pro Trp Ser Asp Thr Ala Thr Ala Asp Ala Phe Ile
1               5                   10                  15

Gln Asn Phe Leu Gly Ala Val Ser Gly Ser Gly Ala Phe Thr Pro Asp
            20                  25                  30

Gln Leu Asp Asp Met Ser Thr Val Gly Asp Thr Ile Met Ser Ala Met
        35                  40                  45

Asp Lys Met Ala Arg Ser Asn Lys Ser Ser Lys Ser Lys Leu Gln Ala
    50                  55                  60

Leu Asn Met Ala Phe Ala Ser Ser Met Ala Glu Ile Ala Ala Val Glu
65                  70                  75                  80

Gln Gly Gly Gln Ser Met Asp Val Lys Thr Asn Ala Ile Ala Asn Ala
                85                  90                  95

Leu Asp Ser Ala Phe Tyr Met Thr Thr Gly Ser Thr Asn Gln Gln Phe
            100                 105                 110

Val Asn Glu Met Arg Ser Leu Ile Asn Met Leu Ser Ala Ala Ala Val
            115                 120                 125

Asn Glu Val
    130

<210> SEQ ID NO 41
<211> LENGTH: 131
<212> TYPE: PRT
<213> ORGANISM: Nephila clavipes

<400> SEQUENCE: 41

Gln Ala Arg Ser Pro Trp Ser Asp Thr Ala Thr Ala Asp Ala Phe Ile
1               5                   10                  15

Gln Asn Phe Leu Ala Ala Val Ser Gly Ser Gly Ala Phe Thr Ser Asp
            20                  25                  30

Gln Leu Asp Asp Met Ser Thr Ile Gly Asp Thr Ile Met Ser Ala Met
        35                  40                  45

Asp Lys Met Ala Arg Ser Asn Lys Ser Ser Gln His Lys Leu Gln Ala
    50                  55                  60

Leu Asn Met Ala Phe Ala Ser Ser Met Ala Glu Ile Ala Ala Val Glu
65                  70                  75                  80

Gln Gly Gly Met Ser Met Ala Val Lys Thr Asn Ala Ile Val Asp Gly
                85                  90                  95

Leu Asn Ser Ala Phe Tyr Met Thr Thr Gly Ala Ala Asn Pro Gln Phe
            100                 105                 110

Val Asn Glu Met Arg Ser Leu Ile Ser Met Ile Ser Ala Ala Ser Ala
            115                 120                 125

Asn Glu Val
    130

<210> SEQ ID NO 42
<211> LENGTH: 129
<212> TYPE: PRT
<213> ORGANISM: Argiope bruennichi

<400> SEQUENCE: 42

Ala Val Pro Ser Val Phe Ser Ser Pro Asn Leu Ala Ser Gly Phe Leu
1               5                   10                  15

Gln Cys Leu Thr Phe Gly Ile Gly Asn Ser Pro Ala Phe Pro Thr Gln
            20                  25                  30

Glu Gln Gln Asp Leu Asp Ala Ile Ala Gln Val Ile Leu Asn Ala Val
        35                  40                  45
```

```
Ser Ser Asn Thr Gly Ala Thr Ser Ala Arg Ala Gln Ala Leu Ser
         50                  55                  60

Thr Ala Leu Ala Ser Ser Leu Thr Asp Leu Leu Ile Ala Glu Ser Ala
 65                  70                  75                  80

Glu Ser Asn Tyr Ser Asn Gln Leu Ser Glu Leu Thr Gly Ile Leu Ser
                 85                  90                  95

Asp Cys Phe Ile Gln Thr Thr Gly Ser Asp Asn Pro Ala Phe Val Ser
            100                 105                 110

Arg Ile Gln Ser Leu Ile Ser Val Leu Ser Gln Asn Ala Asp Thr Asn
            115                 120                 125

Ile

<210> SEQ ID NO 43
<211> LENGTH: 129
<212> TYPE: PRT
<213> ORGANISM: Nephila clavata

<400> SEQUENCE: 43

Pro Val Pro Ser Val Phe Ser Ser Pro Ser Leu Ala Ser Gly Phe Leu
 1               5                  10                  15

Gly Cys Leu Thr Thr Gly Ile Gly Leu Ser Pro Ala Phe Pro Phe Gln
                 20                  25                  30

Glu Gln Gln Asp Leu Asp Asp Leu Ala Lys Val Ile Leu Ser Ala Val
             35                  40                  45

Thr Ser Asn Thr Asp Thr Ser Lys Ser Ala Arg Ala Gln Ala Leu Ser
         50                  55                  60

Thr Ala Leu Ala Ser Ser Leu Ala Asp Leu Leu Ile Ser Glu Ser Ser
 65                  70                  75                  80

Gly Ser Ser Tyr Gln Thr Gln Ile Ser Ala Leu Thr Asn Ile Leu Ser
                 85                  90                  95

Asp Cys Phe Val Thr Thr Thr Gly Ser Asn Asn Pro Ala Phe Val Ser
            100                 105                 110

Arg Val Gln Thr Leu Ile Gly Val Leu Ser Gln Ser Ser Ser Asn Ala
            115                 120                 125

Ile

<210> SEQ ID NO 44
<211> LENGTH: 128
<212> TYPE: PRT
<213> ORGANISM: Latrodectus hesperus

<400> SEQUENCE: 44

Ala Ser Val Asn Ile Phe Asn Ser Pro Asn Ala Thr Ser Phe Leu
 1               5                  10                  15

Asn Cys Leu Arg Ser Asn Ile Glu Ser Ser Pro Ala Phe Pro Phe Gln
                 20                  25                  30

Glu Gln Ala Asp Leu Asp Ser Ile Ala Glu Val Ile Leu Ser Asp Val
             35                  40                  45

Ser Ser Val Asn Thr Ala Ser Ala Thr Ser Leu Ala Leu Ser Thr
         50                  55                  60

Ala Leu Ala Ser Ser Leu Ala Glu Leu Leu Val Thr Glu Ser Ala Glu
 65                  70                  75                  80

Glu Asp Ile Asp Asn Gln Val Val Ala Leu Ser Thr Ile Leu Ser Gln
                 85                  90                  95

Cys Phe Val Glu Thr Thr Gly Ser Pro Asn Pro Ala Phe Val Ala Ser
            100                 105                 110
```

```
Val Lys Ser Leu Leu Gly Val Leu Ser Gln Ser Ala Ser Asn Tyr Glu
        115                 120                 125
```

<210> SEQ ID NO 45
<211> LENGTH: 130
<212> TYPE: PRT
<213> ORGANISM: Nephila clavipes

<400> SEQUENCE: 45

```
Ile Ala Asn Ser Pro Phe Ser Asn Pro Asn Thr Ala Glu Ala Phe Ala
1               5                   10                  15

Arg Ser Phe Val Ser Asn Ile Val Ser Ser Gly Glu Phe Gly Ala Gln
            20                  25                  30

Gly Ala Glu Asp Phe Asp Asp Ile Ile Gln Ser Leu Ile Gln Ala Gln
        35                  40                  45

Ser Met Gly Lys Gly Arg His Asp Thr Lys Ala Lys Ala Lys Ala Met
    50                  55                  60

Gln Val Ala Leu Ala Ser Ser Ile Ala Glu Leu Val Ile Ala Glu Ser
65                  70                  75                  80

Ser Gly Gly Asp Val Gln Arg Lys Thr Asn Val Ile Ser Asn Ala Leu
                85                  90                  95

Arg Asn Ala Leu Met Ser Thr Thr Gly Ser Pro Asn Glu Glu Phe Val
            100                 105                 110

His Glu Val Gln Asp Leu Ile Gln Met Leu Ser Gln Glu Gln Ile Asn
        115                 120                 125

Glu Val
    130
```

<210> SEQ ID NO 46
<211> LENGTH: 130
<212> TYPE: PRT
<213> ORGANISM: Nephila inaurata madagascariensis

<400> SEQUENCE: 46

```
Ile Val Asn Ser Pro Phe Ser Asn Pro Asn Thr Ala Glu Ala Phe Ala
1               5                   10                  15

Arg Ser Phe Val Ser Asn Val Val Ser Ser Gly Glu Phe Gly Ala Gln
            20                  25                  30

Gly Ala Glu Asp Phe Asp Asp Ile Ile Gln Ser Leu Ile Gln Ala Gln
        35                  40                  45

Ser Met Gly Lys Gly Arg His Asp Thr Lys Ala Lys Ala Lys Ala Met
    50                  55                  60

Gln Val Ala Leu Ala Ser Ser Ile Ala Glu Leu Val Ile Ala Glu Ser
65                  70                  75                  80

Ser Gly Gly Asp Val Gln Arg Lys Thr Asn Val Ile Ser Asn Ala Leu
                85                  90                  95

Arg Asn Ala Leu Met Ser Thr Thr Gly Ser Pro Asn Glu Glu Phe Val
            100                 105                 110

His Glu Val Gln Asp Leu Ile Gln Met Leu Ser Gln Glu Gln Ile Asn
        115                 120                 125

Glu Val
    130
```

<210> SEQ ID NO 47
<211> LENGTH: 18
<212> TYPE: PRT
<213> ORGANISM: Euprosthenops australis

```
<400> SEQUENCE: 47

Ala Ser Ala Ser Ala Ala Ala Ser Ala Ala Ser Thr Val Ala Asn Ser
1               5                   10                  15

Val Ser

<210> SEQ ID NO 48
<211> LENGTH: 8
<212> TYPE: PRT
<213> ORGANISM: Euprosthenops australis

<400> SEQUENCE: 48

Ala Ser Ala Ala Ser Ala Ala Ala
1               5

<210> SEQ ID NO 49
<211> LENGTH: 8
<212> TYPE: PRT
<213> ORGANISM: Euprosthenops australis

<400> SEQUENCE: 49

Gly Ser Ala Met Gly Gln Gly Ser
1               5

<210> SEQ ID NO 50
<211> LENGTH: 5
<212> TYPE: PRT
<213> ORGANISM: Euprosthenops australis

<400> SEQUENCE: 50

Ser Ala Ser Ala Gly
1               5

<210> SEQ ID NO 51
<211> LENGTH: 100
<212> TYPE: PRT
<213> ORGANISM: Euprosthenops sp

<400> SEQUENCE: 51

Ser Arg Leu Ser Ser Pro Glu Ala Ser Ser Arg Val Ser Ala Val
1               5                   10                  15

Ser Asn Leu Val Ser Ser Gly Pro Thr Asn Ser Ala Ala Leu Ser Ser
                20                  25                  30

Thr Ile Ser Asn Val Val Ser Gln Ile Gly Ala Ser Asn Pro Gly Leu
            35                  40                  45

Ser Gly Cys Asp Val Leu Val Gln Ala Leu Leu Glu Val Val Ser Ala
        50                  55                  60

Leu Ile His Ile Leu Gly Ser Ser Ile Gly Gln Val Asn Tyr Gly
65                  70                  75                  80

Ser Ala Gly Gln Ala Thr Gln Leu Val Gly Gln Ser Val Tyr Gln Ala
                85                  90                  95

Leu Gly Glu Phe
            100

<210> SEQ ID NO 52
<211> LENGTH: 98
<212> TYPE: PRT
<213> ORGANISM: Euprosthenops australis

<400> SEQUENCE: 52

Ser Arg Leu Ser Ser Pro Ser Ala Val Ser Arg Val Ser Ala Val
1               5                   10                  15
```

-continued

```
Ser Ser Leu Val Ser Asn Gly Gln Val Asn Met Ala Ala Leu Pro Asn
            20                  25                  30

Ile Ile Ser Asn Ile Ser Ser Val Ser Ala Ser Ala Pro Gly Ala
        35                  40                  45

Ser Gly Cys Glu Val Ile Val Gln Ala Leu Leu Glu Val Ile Thr Ala
 50                  55                  60

Leu Val Gln Ile Val Ser Ser Ser Val Gly Tyr Ile Asn Pro Ser
 65                  70                  75                  80

Ala Val Asn Gln Ile Thr Asn Val Val Ala Asn Ala Met Ala Gln Val
                85                  90                  95

Met Gly
```

<210> SEQ ID NO 53
<211> LENGTH: 99
<212> TYPE: PRT
<213> ORGANISM: Argiope trifasciata

<400> SEQUENCE: 53

```
Ser Arg Leu Ser Ser Pro Gly Ala Ala Ser Arg Val Ser Ser Ala Val
 1               5                  10                  15

Thr Ser Leu Val Ser Ser Gly Gly Pro Thr Asn Ser Ala Ala Leu Ser
            20                  25                  30

Asn Thr Ile Ser Asn Val Val Ser Gln Ile Ser Ser Asn Pro Gly
        35                  40                  45

Leu Ser Gly Cys Asp Val Leu Val Gln Ala Leu Leu Glu Ile Val Ser
 50                  55                  60

Ala Leu Val His Ile Leu Gly Ser Ala Asn Ile Gly Gln Val Asn Ser
 65                  70                  75                  80

Ser Gly Val Gly Arg Ser Ala Ser Ile Val Gly Gln Ser Ile Asn Gln
                85                  90                  95

Ala Phe Ser
```

<210> SEQ ID NO 54
<211> LENGTH: 89
<212> TYPE: PRT
<213> ORGANISM: Cyrtophora moluccensis

<400> SEQUENCE: 54

```
Ser His Leu Ser Ser Pro Glu Ala Ser Ser Arg Val Ser Ser Ala Val
 1               5                  10                  15

Ser Asn Leu Val Ser Ser Gly Ser Thr Asn Ser Ala Ala Leu Pro Asn
            20                  25                  30

Thr Ile Ser Asn Val Val Ser Gln Ile Ser Ser Asn Pro Gly Leu
        35                  40                  45

Ser Gly Cys Asp Val Leu Val Gln Ala Leu Leu Glu Val Val Ser Ala
 50                  55                  60

Leu Ile His Ile Leu Gly Ser Ser Ile Gly Gln Val Asn Tyr Gly
 65                  70                  75                  80

Ser Ala Gly Gln Ala Thr Gln Ile Val
                85
```

<210> SEQ ID NO 55
<211> LENGTH: 98
<212> TYPE: PRT
<213> ORGANISM: Latrodectus geometricus

<400> SEQUENCE: 55

```
Ser Ala Leu Ala Ala Pro Ala Thr Ser Ala Arg Ile Ser Ser His Ala
```

```
                    1               5                   10                  15
Ser Thr Leu Leu Ser Asn Gly Pro Thr Asn Pro Ala Ser Ile Ser Asn
                20                  25                  30

Val Ile Ser Asn Ala Val Ser Gln Ile Ser Ser Ser Asn Pro Gly Ala
            35                  40                  45

Ser Ser Cys Asp Val Leu Val Gln Ala Leu Leu Glu Leu Val Thr Ala
        50                  55                  60

Leu Leu Thr Ile Ile Gly Ser Asn Val Gly Asn Val Asn Tyr Asp
65                  70                  75                  80

Ser Ser Gly Gln Tyr Ala Gln Val Val Ser Gln Ser Val Gln Asn Ala
                85                  90                  95

Phe Val

<210> SEQ ID NO 56
<211> LENGTH: 98
<212> TYPE: PRT
<213> ORGANISM: Latrodectus hesperus

<400> SEQUENCE: 56

Ser Ala Leu Ser Ala Pro Ala Thr Ser Ala Arg Ile Ser Ser His Ala
1               5                   10                  15

Ser Ala Leu Leu Ser Ser Gly Pro Thr Asn Pro Ala Ser Ile Ser Asn
                20                  25                  30

Val Ile Ser Asn Ala Val Ser Gln Ile Ser Ser Ser Asn Pro Gly Ala
            35                  40                  45

Ser Ala Cys Asp Val Leu Val Gln Ala Leu Leu Glu Leu Val Thr Ala
        50                  55                  60

Leu Leu Thr Ile Ile Gly Ser Ser Asn Ile Gly Ser Val Asn Tyr Asp
65                  70                  75                  80

Ser Ser Gly Gln Tyr Ala Gln Val Val Thr Gln Ser Val Gln Asn Val
                85                  90                  95

Phe Gly

<210> SEQ ID NO 57
<211> LENGTH: 93
<212> TYPE: PRT
<213> ORGANISM: Macrothele holsti

<400> SEQUENCE: 57

Ser His Leu Ser Ser Pro Glu Ala Ser Ser Arg Val Ser Ser Ala Val
1               5                   10                  15

Ser Asn Leu Val Ser Gly Gly Ser Thr Asn Ser Ala Ala Leu Pro Asn
                20                  25                  30

Thr Ile Ser Asn Val Val Ser Gln Ile Ser Ser Ser Asn Pro Gly Leu
            35                  40                  45

Ser Gly Cys Asp Val Leu Val Gln Ala Leu Leu Glu Val Val Ser Ala
        50                  55                  60

Leu Ile His Ile Leu Gly Ser Ser Ser Ile Gly Gln Val Asp Tyr Gly
65                  70                  75                  80

Ser Ala Gly Gln Ala Thr Gln Ile Val Gly Gln Ser Ala
                85                  90

<210> SEQ ID NO 58
<211> LENGTH: 98
<212> TYPE: PRT
<213> ORGANISM: Nephila clavipes

<400> SEQUENCE: 58
```

-continued

```
Ser Arg Leu Ser Ser Pro Gln Ala Ser Ser Arg Val Ser Ser Ala Val
1               5                   10                  15

Ser Asn Leu Val Ala Ser Gly Pro Thr Asn Ser Ala Ala Leu Ser Ser
                20                  25                  30

Thr Ile Ser Asn Val Val Ser Gln Ile Gly Ala Ser Asn Pro Gly Leu
            35                  40                  45

Ser Gly Cys Asp Val Leu Ile Gln Ala Leu Leu Glu Val Val Ser Ala
        50                  55                  60

Leu Ile Gln Ile Leu Gly Ser Ser Ile Gly Gln Val Asn Tyr Gly
65                  70                  75                  80

Ser Ala Gly Gln Ala Thr Gln Ile Val Gly Gln Ser Val Tyr Gln Ala
                85                  90                  95

Leu Gly
```

<210> SEQ ID NO 59
<211> LENGTH: 89
<212> TYPE: PRT
<213> ORGANISM: Nephila pilipes

<400> SEQUENCE: 59

```
Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Ser Asn
                20                  25                  30

Thr Ile Ser Asn Val Val Ser Gln Ile Ser Ser Ser Asn Pro Gly Leu
            35                  40                  45

Ser Gly Cys Asp Val Leu Val Gln Ala Leu Leu Glu Val Val Ser Ala
        50                  55                  60

Leu Ile His Ile Leu Gly Ser Ser Ile Gly Gln Val Asn Tyr Gly
65                  70                  75                  80

Ser Ala Gly Gln Ala Thr Gln Ile Val
                85
```

<210> SEQ ID NO 60
<211> LENGTH: 87
<212> TYPE: PRT
<213> ORGANISM: Nephila madagascariensis

<400> SEQUENCE: 60

```
Ser Arg Leu Ser Ser Pro Gln Ala Ser Ser Arg Val Ser Ser Ala Val
1               5                   10                  15

Ser Asn Leu Val Ala Ser Gly Pro Thr Asn Ser Ala Ala Leu Ser Ser
                20                  25                  30

Thr Ile Ser Asn Ala Val Ser Gln Ile Gly Ala Ser Asn Pro Gly Leu
            35                  40                  45

Ser Gly Cys Asp Val Leu Ile Gln Ala Leu Leu Glu Val Val Ser Ala
        50                  55                  60

Leu Ile His Ile Leu Gly Ser Ser Ile Gly Gln Val Asn Tyr Gly
65                  70                  75                  80

Ser Ala Gly Gln Ala Thr Gln
                85
```

<210> SEQ ID NO 61
<211> LENGTH: 87
<212> TYPE: PRT
<213> ORGANISM: Nephila senegalensis

<400> SEQUENCE: 61

```
Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Ser Ser
                20                  25                  30

Thr Ile Ser Asn Val Val Ser Gln Ile Gly Ala Ser Asn Pro Gly Leu
            35                  40                  45

Ser Gly Cys Asp Val Leu Ile Gln Ala Leu Leu Glu Val Val Ser Ala
        50                  55                  60

Leu Val His Ile Leu Gly Ser Ser Ile Gly Gln Val Asn Tyr Gly
65                  70                  75                  80

Ser Ala Gly Gln Ala Thr Gln
                85
```

<210> SEQ ID NO 62
<211> LENGTH: 89
<212> TYPE: PRT
<213> ORGANISM: Octonoba varians

<400> SEQUENCE: 62

```
Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Ser Asn
                20                  25                  30

Thr Ile Ser Asn Val Val Ser Gln Ile Ser Ser Asn Pro Gly Leu
            35                  40                  45

Ser Gly Cys Asp Val Leu Val Gln Ala Leu Leu Glu Val Val Ser Ala
        50                  55                  60

Pro Ile His Ile Leu Gly Ser Ser Ile Gly Gln Val Asn Tyr Gly
65                  70                  75                  80

Ser Ala Gly Gln Ala Thr Gln Ile Val
                85
```

<210> SEQ ID NO 63
<211> LENGTH: 89
<212> TYPE: PRT
<213> ORGANISM: Psechrus sinensis

<400> SEQUENCE: 63

```
Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Pro Asn
                20                  25                  30

Thr Ile Ser Asn Val Val Ser Gln Ile Ser Ser Asn Pro Gly Leu
            35                  40                  45

Ser Gly Cys Asp Val Leu Val Gln Ala Leu Leu Glu Val Val Ser Ala
        50                  55                  60

Leu Ile His Ile Leu Gly Ser Ser Ile Gly Gln Val Asn Tyr Gly
65                  70                  75                  80

Ser Ala Gly Gln Ala Thr Gln Ile Val
                85
```

<210> SEQ ID NO 64
<211> LENGTH: 88
<212> TYPE: PRT
<213> ORGANISM: Tetragnatha kauaiensis

```
<400> SEQUENCE: 64

Ser Leu Leu Ser Ser Pro Ala Ser Asn Ala Arg Ile Ser Ala Val
1               5                   10                  15

Ser Ala Leu Ala Ser Gly Ala Ala Ser Gly Pro Gly Tyr Leu Ser Ser
            20                  25                  30

Val Ile Ser Asn Val Val Ser Gln Val Ser Ser Asn Ser Gly Gly Leu
        35                  40                  45

Val Gly Cys Asp Thr Leu Val Gln Ala Leu Leu Glu Ala Ala Ala Ala
    50                  55                  60

Leu Val His Val Leu Ala Ser Ser Gly Gly Gln Val Asn Leu Asn
65                  70                  75                  80

Thr Ala Gly Tyr Thr Ser Gln Leu
                85

<210> SEQ ID NO 65
<211> LENGTH: 88
<212> TYPE: PRT
<213> ORGANISM: Tetragnatha versicolor

<400> SEQUENCE: 65

Ser Arg Leu Ser Ser Pro Ala Ser Asn Ala Arg Ile Ser Ala Val
1               5                   10                  15

Ser Ala Leu Ala Ser Gly Gly Ala Ser Ser Pro Gly Tyr Leu Ser Ser
            20                  25                  30

Ile Ile Ser Asn Val Val Ser Gln Val Ser Ser Asn Asn Asp Gly Leu
        35                  40                  45

Ser Gly Cys Asp Thr Val Val Gln Ala Leu Leu Glu Val Ala Ala Ala
    50                  55                  60

Leu Val His Val Leu Ala Ser Ser Asn Ile Gly Gln Val Asn Leu Asn
65                  70                  75                  80

Thr Ala Gly Tyr Thr Ser Gln Leu
                85

<210> SEQ ID NO 66
<211> LENGTH: 89
<212> TYPE: PRT
<213> ORGANISM: Araneus bicentenarius

<400> SEQUENCE: 66

Ser Arg Leu Ser Ser Ala Ala Ser Ser Arg Val Ser Ala Val
1               5                   10                  15

Ser Ser Leu Val Ser Ser Gly Pro Thr Thr Pro Ala Ala Leu Ser Asn
            20                  25                  30

Thr Ile Ser Ser Ala Val Ser Gln Ile Ser Ala Ser Asn Pro Gly Leu
        35                  40                  45

Ser Gly Cys Asp Val Leu Val Gln Ala Leu Leu Glu Val Val Ser Ala
    50                  55                  60

Leu Val His Ile Leu Gly Ser Ser Ser Val Gly Gln Ile Asn Tyr Gly
65                  70                  75                  80

Ala Ser Ala Gln Tyr Ala Gln Met Val
                85

<210> SEQ ID NO 67
<211> LENGTH: 97
<212> TYPE: PRT
<213> ORGANISM: Argiope amoena
```

-continued

<400> SEQUENCE: 67

```
Arg Leu Ser Ser Pro Gln Ala Ser Ser Arg Val Ser Ser Ala Val Ser
1               5                   10                  15

Thr Leu Val Ser Ser Gly Pro Thr Asn Pro Ala Ser Leu Ser Asn Ala
            20                  25                  30

Ile Gly Ser Val Val Ser Gln Val Ser Ala Ser Asn Pro Gly Leu Pro
        35                  40                  45

Ser Cys Asp Val Leu Val Gln Ala Leu Leu Glu Ile Val Ser Ala Leu
50                  55                  60

Val His Ile Leu Gly Ser Ser Ile Gly Gln Ile Asn Tyr Ser Ala
65                  70                  75                  80

Ser Ser Gln Tyr Ala Arg Leu Val Gly Gln Ser Ile Ala Gln Ala Leu
            85                  90                  95

Gly
```

<210> SEQ ID NO 68
<211> LENGTH: 82
<212> TYPE: PRT
<213> ORGANISM: Argiope aurantia

<400> SEQUENCE: 68

```
Ser Arg Leu Ser Ser Pro Gln Ala Ser Ser Arg Val Ser Ser Ala Val
1               5                   10                  15

Ser Thr Leu Val Ser Ser Gly Pro Thr Asn Pro Ala Ala Leu Ser Asn
            20                  25                  30

Ala Ile Ser Ser Val Val Ser Gln Val Ser Ala Ser Asn Pro Gly Leu
        35                  40                  45

Ser Gly Cys Asp Val Leu Val Gln Ala Leu Leu Glu Leu Val Ser Ala
50                  55                  60

Leu Val His Ile Leu Gly Ser Ser Ser Ile Gly Gln Ile Asn Tyr Ala
65                  70                  75                  80

Ala Ser
```

<210> SEQ ID NO 69
<211> LENGTH: 98
<212> TYPE: PRT
<213> ORGANISM: Argiope trifasciata

<400> SEQUENCE: 69

```
Ser Arg Leu Ser Ser Pro Gln Ala Ser Ser Arg Val Ser Ser Ala Val
1               5                   10                  15

Ser Thr Leu Val Ser Ser Gly Pro Thr Asn Pro Ala Ser Leu Ser Asn
            20                  25                  30

Ala Ile Ser Ser Val Val Ser Gln Val Ser Ser Ser Asn Pro Gly Leu
        35                  40                  45

Ser Gly Cys Asp Val Leu Val Gln Ala Leu Leu Glu Ile Val Ser Ala
50                  55                  60

Leu Val His Ile Leu Gly Ser Ser Ser Ile Gly Gln Ile Asn Tyr Ala
65                  70                  75                  80

Ala Ser Ser Gln Tyr Ala Gln Leu Val Gly Gln Ser Leu Thr Gln Ala
            85                  90                  95

Leu Gly
```

<210> SEQ ID NO 70
<211> LENGTH: 89
<212> TYPE: PRT
<213> ORGANISM: Gasteracantha mammosa

```
<400> SEQUENCE: 70

Ser Arg Leu Ser Ser Pro Gln Ala Gly Ala Arg Val Ser Ser Ala Val
1               5                   10                  15

Ser Ala Leu Val Ala Ser Gly Pro Thr Ser Pro Ala Ala Val Ser Ser
            20                  25                  30

Ala Ile Ser Asn Val Ala Ser Gln Ile Ser Ala Ser Asn Pro Gly Leu
        35                  40                  45

Ser Gly Cys Asp Val Leu Val Gln Ala Leu Leu Glu Ile Val Ser Ala
    50                  55                  60

Leu Val Ser Ile Leu Ser Ser Ala Ser Ile Gly Gln Ile Asn Tyr Gly
65                  70                  75                  80

Ala Ser Gly Gln Tyr Ala Ala Met Ile
                85

<210> SEQ ID NO 71
<211> LENGTH: 90
<212> TYPE: PRT
<213> ORGANISM: Latrodectus geometricus

<400> SEQUENCE: 71

Ser Ala Leu Ser Ser Pro Thr Thr His Ala Arg Ile Ser Ser His Ala
1               5                   10                  15

Ser Thr Leu Leu Ser Ser Gly Pro Thr Asn Ser Ala Ala Ile Ser Asn
            20                  25                  30

Val Ile Ser Asn Ala Val Ser Gln Val Ser Ala Ser Asn Pro Gly Ser
        35                  40                  45

Ser Ser Cys Asp Val Leu Val Gln Ala Leu Leu Glu Leu Ile Thr Ala
    50                  55                  60

Leu Ile Ser Ile Val Asp Ser Asn Ile Gly Gln Val Asn Tyr Gly
65                  70                  75                  80

Ser Ser Gly Gln Tyr Ala Gln Met Val Gly
                85                  90

<210> SEQ ID NO 72
<211> LENGTH: 98
<212> TYPE: PRT
<213> ORGANISM: Latrodectus hesperus

<400> SEQUENCE: 72

Ser Ala Leu Ser Ser Pro Thr Thr His Ala Arg Ile Ser Ser His Ala
1               5                   10                  15

Ser Thr Leu Leu Ser Ser Gly Pro Thr Asn Ala Ala Leu Ser Asn
            20                  25                  30

Val Ile Ser Asn Ala Val Ser Gln Val Ser Ala Ser Asn Pro Gly Ser
        35                  40                  45

Ser Cys Asp Val Leu Val Gln Ala Leu Leu Glu Ile Ile Thr Ala
    50                  55                  60

Leu Ile Ser Ile Leu Asp Ser Ser Val Gly Gln Val Asn Tyr Gly
65                  70                  75                  80

Ser Ser Gly Gln Tyr Ala Gln Ile Val Gly Gln Ser Met Gln Ala
                85                  90                  95

Met Gly

<210> SEQ ID NO 73
<211> LENGTH: 97
<212> TYPE: PRT
<213> ORGANISM: Nephila clavipes
```

```
<400> SEQUENCE: 73

Ser Arg Leu Ala Ser Pro Asp Ser Gly Ala Arg Val Ala Ser Ala Val
1               5                   10                  15

Ser Asn Leu Val Ser Ser Gly Pro Thr Ser Ser Ala Ala Leu Ser Ser
            20                  25                  30

Val Ile Ser Asn Ala Val Ser Gln Ile Gly Ala Ser Asn Pro Gly Leu
        35                  40                  45

Ser Gly Cys Asp Val Leu Ile Gln Ala Leu Leu Glu Ile Val Ser Ala
    50                  55                  60

Cys Val Thr Ile Leu Ser Ser Ser Ile Gly Gln Val Asn Tyr Gly
65                  70                  75                  80

Ala Ala Ser Gln Phe Ala Gln Val Val Gly Gln Ser Val Leu Ser Ala
                85                  90                  95

Phe

<210> SEQ ID NO 74
<211> LENGTH: 82
<212> TYPE: PRT
<213> ORGANISM: Nephila madagascariensis

<400> SEQUENCE: 74

Ser Arg Leu Ala Ser Pro Asp Ser Gly Ala Arg Val Ala Ser Ala Val
1               5                   10                  15

Ser Asn Leu Val Ser Ser Gly Pro Thr Ser Ser Ala Ala Leu Ser Ser
            20                  25                  30

Val Ile Ser Asn Ala Val Ser Gln Ile Gly Ala Ser Asn Pro Gly Leu
        35                  40                  45

Ser Gly Cys Asp Val Leu Ile Gln Ala Leu Leu Glu Ile Val Ser Ala
    50                  55                  60

Cys Val Thr Ile Leu Ser Ser Ser Ile Gly Gln Val Asn Tyr Gly
65                  70                  75                  80

Ala Ala

<210> SEQ ID NO 75
<211> LENGTH: 82
<212> TYPE: PRT
<213> ORGANISM: Nephila senegalensis
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid

<400> SEQUENCE: 75

Ser Arg Leu Ala Ser Pro Asp Ser Gly Ala Arg Val Ala Ser Ala Val
1               5                   10                  15

Ser Asn Leu Val Ser Ser Gly Pro Thr Ser Ser Ala Ala Leu Ser Ser
            20                  25                  30

Val Ile Xaa Asn Ala Val Ser Gln Ile Gly Ala Ser Asn Pro Gly Leu
        35                  40                  45

Ser Gly Cys Asp Val Leu Ile Xaa Ala Leu Leu Glu Ile Val Ser Ala
    50                  55                  60

Cys Val Thr Ile Leu Ser Ser Ser Ile Gly Gln Val Asn Tyr Gly
65                  70                  75                  80

Ala Ala
```

```
<210> SEQ ID NO 76
<211> LENGTH: 71
<212> TYPE: PRT
<213> ORGANISM: Dolomedes tenebrosus

<400> SEQUENCE: 76

Ser Arg Leu Ser Ser Pro Glu Ala Ala Ser Arg Val Ser Ser Ala Val
1               5                   10                  15

Ser Ser Leu Val Ser Asn Gly Gln Val Asn Val Asp Ala Leu Pro Ser
            20                  25                  30

Ile Ile Ser Asn Leu Ser Ser Ser Ile Ser Ala Ser Ala Thr Thr Ala
        35                  40                  45

Ser Asp Cys Glu Val Leu Val Gln Val Leu Leu Glu Val Val Ser Ala
    50                  55                  60

Leu Val Gln Ile Val Cys Ser
65                  70

<210> SEQ ID NO 77
<211> LENGTH: 97
<212> TYPE: PRT
<213> ORGANISM: Dolomedes tenebrosus

<400> SEQUENCE: 77

Ser Arg Leu Ser Ser Pro Gln Ala Ala Ser Arg Val Ser Ser Ala Val
1               5                   10                  15

Ser Ser Leu Val Ser Asn Gly Gln Val Asn Val Ala Ala Leu Pro Ser
            20                  25                  30

Ile Ile Ser Ser Leu Ser Ser Ser Ile Ser Ala Ser Ser Thr Ala Ala
        35                  40                  45

Ser Asp Cys Glu Val Leu Val Gln Val Leu Leu Glu Ile Val Ser Ala
    50                  55                  60

Leu Val Gln Ile Val Ser Ser Ala Asn Val Gly Tyr Ile Asn Pro Glu
65                  70                  75                  80

Ala Ser Gly Ser Leu Asn Ala Val Gly Ser Ala Leu Ala Ala Ala Met
                85                  90                  95

Gly

<210> SEQ ID NO 78
<211> LENGTH: 93
<212> TYPE: PRT
<213> ORGANISM: Araneus diadematus

<400> SEQUENCE: 78

Asn Arg Leu Ser Ser Ala Gly Ala Ala Ser Arg Val Ser Ser Asn Val
1               5                   10                  15

Ala Ala Ile Ala Ser Ala Gly Ala Ala Leu Pro Asn Val Ile Ser
                20                  25                  30

Asn Ile Tyr Ser Gly Val Leu Ser Ser Gly Val Ser Ser Ser Glu Ala
            35                  40                  45

Leu Ile Gln Ala Leu Leu Glu Val Ile Ser Ala Leu Ile His Val Leu
    50                  55                  60

Gly Ser Ala Ser Ile Gly Asn Val Ser Ser Val Gly Val Asn Ser Ala
65                  70                  75                  80

Leu Asn Ala Val Gln Asn Ala Val Gly Ala Tyr Ala Gly
                85                  90
```

```
<210> SEQ ID NO 79
<211> LENGTH: 98
<212> TYPE: PRT
<213> ORGANISM: Araneus diadematus

<400> SEQUENCE: 79

Ser Arg Leu Ser Ser Pro Ser Ala Ala Ala Arg Val Ser Ser Ala Val
1               5                   10                  15

Ser Leu Val Ser Asn Gly Gly Pro Thr Ser Pro Ala Ala Leu Ser Ser
            20                  25                  30

Ser Ile Ser Asn Val Val Ser Gln Ile Ser Ala Ser Asn Pro Gly Leu
        35                  40                  45

Ser Gly Cys Asp Ile Leu Val Gln Ala Leu Leu Glu Ile Ile Ser Ala
    50                  55                  60

Leu Val His Ile Leu Gly Ser Ala Asn Ile Gly Pro Val Asn Ser Ser
65                  70                  75                  80

Ser Ala Gly Gln Ser Ala Ser Ile Val Gly Gln Ser Val Tyr Arg Ala
                85                  90                  95

Leu Ser

<210> SEQ ID NO 80
<211> LENGTH: 98
<212> TYPE: PRT
<213> ORGANISM: Araneus diadematus

<400> SEQUENCE: 80

Ser Arg Leu Ser Ser Pro Ala Ala Ser Ser Arg Val Ser Ser Ala Val
1               5                   10                  15

Ser Ser Leu Val Ser Ser Gly Pro Thr Lys His Ala Ala Leu Ser Asn
            20                  25                  30

Thr Ile Ser Ser Val Val Ser Gln Val Ser Ala Ser Asn Pro Gly Leu
        35                  40                  45

Ser Gly Cys Asp Val Leu Val Gln Ala Leu Leu Glu Val Val Ser Ala
    50                  55                  60

Leu Val Ser Ile Leu Gly Ser Ser Ser Ile Gly Gln Ile Asn Tyr Gly
65                  70                  75                  80

Ala Ser Ala Gln Tyr Thr Gln Met Val Gly Gln Ser Val Ala Gln Ala
                85                  90                  95

Leu Ala

<210> SEQ ID NO 81
<211> LENGTH: 94
<212> TYPE: PRT
<213> ORGANISM: Araneus diadematus

<400> SEQUENCE: 81

Ser Val Tyr Leu Arg Leu Gln Pro Arg Leu Glu Val Ser Ser Ala Val
1               5                   10                  15

Ser Ser Leu Val Ser Ser Gly Pro Thr Asn Gly Ala Ala Val Ser Gly
            20                  25                  30

Ala Leu Asn Ser Leu Val Ser Gln Ile Ser Ala Ser Asn Pro Gly Leu
        35                  40                  45

Ser Gly Cys Asp Ala Leu Val Gln Ala Leu Leu Glu Leu Val Ser Ala
    50                  55                  60
```

```
Leu Val Ala Ile Leu Ser Ser Ala Ser Ile Gly Gln Val Asn Val Ser
65              70              75                  80

Ser Val Ser Gln Ser Thr Gln Met Ile Ser Gln Ala Leu Ser
                85              90
```